United States Patent
Cresswell et al.

(10) Patent No.: US 10,688,091 B2
(45) Date of Patent: *Jun. 23, 2020

(54) ARIPIPRAZOLE PRODRUG COMPOSITION

(71) Applicant: ALKERMES PHARMA IRELAND LIMITED, Dublin (IE)

(72) Inventors: Philip Cresswell, Athlone (IE); Magali Hickey, Westwood, MA (US); Kristopher Perkin, Athlone (IE); Greg Smith, Norton, MA (US); Elaine Liversidge, Charlestown, MA (US); Brian Steinberg, Arlington, MA (US); David Manser, Keenagh (IE); Tarek Zeidan, Waltham, MA (US)

(73) Assignee: ALKERMES PHARMA IRELAND LIMITED, Dublin (IE)

( * ) Notice: Subject to any disclaimer, the term of this patent is extended or adjusted under 35 U.S.C. 154(b) by 0 days.

This patent is subject to a terminal disclaimer.

(21) Appl. No.: 16/416,818

(22) Filed: May 20, 2019

(65) Prior Publication Data

US 2019/0269676 A1  Sep. 5, 2019

Related U.S. Application Data

(60) Continuation of application No. 16/024,729, filed on Jun. 29, 2018, which is a division of application No. 14/828,229, filed on Aug. 17, 2015, now Pat. No. 10,016,415.

(60) Provisional application No. 62/038,665, filed on Aug. 18, 2014.

(51) Int. Cl.
*A61K 31/496* (2006.01)
*A61K 9/00* (2006.01)
*A61K 45/06* (2006.01)
*A61K 47/26* (2006.01)

(52) U.S. Cl.
CPC .......... *A61K 31/496* (2013.01); *A61K 9/0019* (2013.01); *A61K 45/06* (2013.01); *A61K 47/26* (2013.01)

(58) Field of Classification Search
CPC ...... A61K 31/496; A61K 47/26; A61K 45/06; A61K 9/0019
See application file for complete search history.

(56) References Cited

U.S. PATENT DOCUMENTS

| | | | |
|---|---|---|---|
| 5,145,684 A | 9/1992 | Liversidge et al. | |
| 5,470,583 A | 11/1995 | Na et al. | |
| 5,510,118 A | 4/1996 | Bosch et al. | |
| 5,518,187 A | 5/1996 | Bruno et al. | |
| 5,534,270 A | 7/1996 | De Castro | |
| 5,543,133 A | 8/1996 | Swanson et al. | |
| 5,560,932 A | 10/1996 | Bagchi et al. | |
| 5,662,883 A | 9/1997 | Bagchi et al. | |
| 5,665,331 A | 9/1997 | Bagchi et al. | |
| 5,718,388 A | 2/1998 | Czekai et al. | |
| 5,862,999 A | 1/1999 | Czekai et al. | |
| 6,406,718 B1 | 6/2002 | Cooper | |
| 8,431,576 B2 | 4/2013 | Remenar | |
| 2011/0003828 A1 | 1/2011 | Blumberg et al. | |
| 2012/0238552 A1 | 9/2012 | Perry et al. | |
| 2013/0267503 A1 | 10/2013 | Perry et al. | |
| 2013/0267504 A1 | 10/2013 | Perry et al. | |
| 2013/0267505 A1 | 10/2013 | Perry et al. | |
| 2014/0088115 A1 | 3/2014 | Perry et al. | |
| 2015/0265529 A1 | 9/2015 | Hickey et al. | |
| 2016/0045495 A1 | 2/2016 | Cresswell et al. | |
| 2016/0051546 A1 | 2/2016 | Morales et al. | |

FOREIGN PATENT DOCUMENTS

| | | |
|---|---|---|
| CN | 105 012 236 A | 11/2015 |
| WO | WO 97/14407 | 4/1997 |
| WO | WO 03/030872 A2 | 4/2003 |
| WO | WO 2005/041937 A2 | 5/2005 |
| WO | WO 2012/129156 A1 | 9/2012 |
| WO | WO 2016/026822 A1 | 2/2016 |

OTHER PUBLICATIONS

U.S. Appl. No. 13/423,606 / 2012/0238552 / U.S. Pat. No. 9,034,867, filed Mar. 19, 2012 / Sep. 20, 2012 / May 19, 2015, Jason M. Perry.
U.S. Appl. No. 14/714,621 / 2015/0258115 / U.S. Pat. No. 9,351,976, filed May 18, 2015 / Sep. 17, 2015 / May 31, 2016, Jason M. Perry.
U.S. Appl. No. 14/688,050 / 2016/0038508, filed Apr. 16, 2015 / Feb. 11, 2016, Jason M. Perry.
U.S. Appl. No. 15/154,562, filed May 13, 2016, Jason M. Perry.
U.S. Appl. No. 15/388,554 / 2017/0196856 / U.S. Pat. No. 10,226,458, filed Dec. 22, 2016 / Jul. 13, 2017 / Mar. 12, 2019, Jason M. Perry.
U.S. Appl. No. 16/248,259, filed Jan. 15, 2019, Jason M. Perry.
U.S. Appl. No. 13/801,025 / 2013/0267503 / U.S. Pat. No. 10,004,807, filed Mar. 13, 2013 / Oct. 10, 2013 / Jun. 26, 2018, Jason M. Perry.
U.S. Appl. No. 13/801,167 / 2013/0267504 / U.S. Pat. No. 9,993,556, filed Mar. 13, 2013 / Oct. 10, 2013 / Jun. 12, 2018, Jason M. Perry.

(Continued)

*Primary Examiner* — Matthew P Coughlin
*Assistant Examiner* — Thurman Wheeler
(74) *Attorney, Agent, or Firm* — Brian C. Trinque; Lathrop GPM, LLP

(57) ABSTRACT

Described is a composition comprising (a) a population of particles of an aripiprazole prodrug having a volume based particle size (Dv50) of less than 1000 nm and (b) at least one surface stabilizer comprising an adsorbed component which is adsorbed on the surface of the aripiprazole prodrug particles and a free component available for solubilisation of the aripiprazole prodrug. The surface stabilizer to prodrug ratio provides the optimal quantity of free surface stabilizer for the purposes of producing a lead-in formulation. Also described are methods of treatment using the aforementioned composition.

21 Claims, 30 Drawing Sheets

(56) References Cited

OTHER PUBLICATIONS

U.S. Appl. No. 13/801,344 / 2013/0267505 / U.S. Pat. No. 9,999,670, filed Mar. 13, 2013 / Oct. 10, 2013 / Jun. 19, 2018, Jason M. Perry.
U.S. Appl. No. 14/031,842 / 2014/0088115 / U.S. Pat. No. 9,193,685, filed Sep. 19, 2013 / Mar. 27, 2014 / Nov. 24, 2015, Jason M. Perry.
U.S. Appl. No. 14/882,069 / 2016/0136279 / U.S. Pat. No. 9,861,699, filed Oct. 13, 2015 / May 19, 2016 / Jan. 9, 2018, Jason M. Perry.
U.S. Appl. No. 15/705,237 / 2018/0000944, filed Sep. 14, 2017 / Jan. 4, 2018, Jason M. Perry.
U.S. Appl. No. 16/425,150, filed May 29, 2019, Jason M. Perry.
U.S. Appl. No. 14/633,042 / 2015/0265529 / U.S. Pat. No. 9,452,131, filed Mar. 19, 2015 / Sep. 24, 2015 / Sep. 27, 2016, Magali B. Hickey.
U.S. Appl. No. 15/164,473 / 2016/0263111 / U.S. Pat. No. 9,526,726, filed May 25, 2016 / Sep. 15, 2016 / Dec. 27, 2016, Magali B. Hickey.
U.S. Appl. No. 15/349,243 / 2017/0157117 / U.S. Pat. No. 10,085,980, filed Nov. 11, 2016 / Jun. 8, 2017 / Oct. 2, 2018, Magali B. Hickey.
U.S. Appl. No. 16/116,652 / 2018/0369239 / U.S. Pat. No. 10,238,651, filed Aug. 29, 2018 / Dec. 27, 2018 / Mar. 26, 2019, Magali B. Hickey.
U.S. Appl. No. 16/271,248, filed Feb. 8, 2019, Magali B. Hickey.
U.S. Appl. No. 14/833,638 / 2016/0051546 / U.S. Pat. No. 10,064,859, filed Aug. 24, 2015 / Feb. 25, 2016 / Sep. 4, 2018, Wilfredo Morales.
U.S. Appl. No. 16/043,721 / 2019/0015408, filed Jul. 24, 2018 Jan. 17, 2019, Wilfredo Morales.
U.S. Appl. No. 12/823,007 / 2011/0015156 / U.S. Pat. No. 8,431,576, filed Jun. 24, 2010 / Jan. 20, 2011 / Apr. 30, 2013, Julius F. Remenar.
U.S. Appl. No. 13/607,066 / 2013/0096089 / U.S. Pat. No. 8,796,276, filed Sep. 7, 2012 / Apr. 18, 2013 / Aug. 5, 2014, Julius F. Remenar.
U.S. Appl. No. 14/297,195 / 2014/0350254, filed Jun. 5, 2014 / Nov. 27, 2014, Julius F. Remenar.
U.S. Appl. No. 14/677,333 / 2015/0274670, filed Apr. 2, 2015 / Oct. 1, 2015, Julius F. Remenar.
U.S. Appl. No. 15/147,021 / 2016/0318869 / U.S. Pat. No. 10,023,537, filed May 5, 2016 / Nov. 3, 2016 / Jul. 17, 2018, Julius F. Remenar.
U.S. Appl. No. 15/875,478 / 2018/0162816 / U.S. Pat. No. 10,112,903, filed Jan. 19, 2018 / Jun. 14, 2018 / Oct. 30, 2018, Julius F. Remenar.
U.S. Appl. No. 16/131,773 / 2019/0084937, filed Sep. 14, 2018 / Mar. 21, 2019, Julius F. Remenar.
U.S. Appl. No. 16/425,119, filed May 29, 2019, Julius F. Remenar.
U.S. Appl. No. 12/823,102 / 2011/0003828 / U.S. Pat. No. 8,686,009, filed Jun. 24, 2010 / Jan. 6, 2011 / Apr. 1, 2014, Laura Cook Blumberg.
U.S. Appl. No. 14/172,391 / 2014/0221653 / U.S. Pat. No. 9,102,618, filed Feb. 4, 2014 / Aug. 7, 2014 / Aug. 11, 2015, Laura Cook Blumberg.
U.S. Appl. No. 14/755,412 / 2015/0376143, filed Jun. 30, 2015 / Dec. 31, 2015, Laura Cook Blumberg.
U.S. Appl. No. 15/227,117 / 2017/0015659 / U.S. Pat. No. 10,040,787, filed Aug. 3, 2016 / Jan. 19, 2017 / Aug. 7, 2018, Laura Cook Blumberg.
U.S. Appl. No. 16/023,887 / 2019/0031648, filed Jun. 29, 2018 / Jan. 31, 2019, Laura Cook Blumberg.
U.S. Appl. No. 14/828,229 / 2016/0045495 / U.S. Pat. No. 10,016,415, filed Aug. 17, 2015 / Feb. 18, 2016 / Jul. 10, 2018, Philip Cresswell.
U.S. Appl. No. 16/024,729 / 2018/0318293, filed Jun. 29, 2018 / Nov. 8, 2018, Philip Cresswell.
International Search Report and Written Opinion issued in related International Patent Application No. PCT/EP2015/068872, completed Oct. 8, 2015.
Aulton, "Pharmaceutics: The Science of Dosage form Design," pp. 569-580 (1988).
Haskell, Part II. Nanoparticle Characterization and Properties, "Physical Characterization of Nanoparticles," pp. 103-138 (2006).
European Search Report issued in related European Patent Application No. 16 15 6356, dated Jul. 20, 2016.
Turncliff et al., "Relative Bioavailability and Safety of Aripiprazole Lauroxil, a Novel once-monthly, long-acting injectable atypical antipsychotic, following deltoid and gluteal administration in adult subjects with schizophrenia," *Schizophrenia Research*, vol. 159, No. 2-3, (2014).
Examination Report corresponding to EP 15750750.0, dated Nov. 29, 2017, pp. 1-8.
Merisko-Liversidge et al., "Nanosizing: a Formulation Approach for Poorly-Water-Soluble Compounds", European Journal of Pharmaceutical Sciences, vol. 18, pp. 113-120, 2003.
Nagarwal et al., "Nanocrystal Technology in the Delivery of Poorly Soluble Drugs: An Overview", Current Drug Delivery, vol. 8, No. 4, pp. 398-406, 2011.
Remenar, "Making the Leap from Daily Oral Dosing to Long-Acting Injectables: Lessons from the Antipsychotics", Molecular Pharmaceutics, vol. 11, pp. 1739-1749, Mar. 28, 2014.
Notice of Opposition in corresponding EP Patent No. 3182958, filed Nov. 27, 2019.

ARIPIPRAZOLE PRODRUG COMPOSITION

CROSS-REFERENCE TO RELATED APPLICATIONS

This application is a continuation of Ser. No. 16/024,729 filed on Jun. 29, 2018, which is a Divisional of U.S. patent application Ser. No. 14/828,229, filed Aug. 17, 2015, now issued as U.S. Pat. No. 10,016,415, which application claims priority from U.S. Provisional Patent Application No. 62/038,665, filed Aug. 18, 2014. The contents of these applications are incorporated herein by reference in their entirety.

FIELD OF THE INVENTION

The present invention relates to compositions and methods of an aripiprazole prodrug. In particular, said compositions and methods comprise an aripiprazole prodrug having a particle size of less than about 1000 nm and a surface stabilizer, wherein the surface stabilizer to prodrug drug ratio is between about 0.1:1 and about 40:1, most preferably about 17:1. The surface stabilizer to prodrug ratio provides the optimal quantity of free surface stabilizer for the purpose of producing a lead in formulation.

BACKGROUND OF THE INVENTION

ABILIFY MAINTENA® (aripiprazole) extended-release injectable suspension, for intramuscular use, does not reach steady state plasma concentrations in humans immediately upon its administration. Initiation therapy of Abilify Maintena® requires 14 consecutive days of concurrent oral aripiprazole (10 mg to 20 mg) with the first depot dose to achieve therapeutic concentrations (Otsuka America Pharmaceutical, Inc., "Abilify Maintena Product Insert, 2013"). Patient compliance during this 14 day lead in period presents a challenge which the present invention addresses.

SUMMARY OF INVENTION

The present invention provides stabilized aripiprazole prodrug compositions that can be tailored to have a desired initial in-vivo release profile. In particular, the present invention provides compositions and methods that reduce the number of "lead in" days of oral aripiprazole required to achieve steady state plasma concentrations.

More specifically, the present invention provides a composition comprising: (a) a population of particles of an aripiprazole prodrug having an volume based particle size (Dv50) of less than 1000 nm as determined by light scattering techniques, (b) at least one surface stabilizer comprising an adsorbed component (i.e. quantity of surface stabilizer) which is adsorbed on the surface of the aripiprazole prodrug particles and a free component (i.e. second quantity of surface stabilizer) available for solubilisation of the aripiprazole prodrug (i.e. the free stabilizer component not adsorbed on the aripiprazole prodrug particles). The ratio of aripiprazole prodrug to surface stabilizer is between about 0.1:1 and about 40:1. The aripiprazole prodrug has the formula:

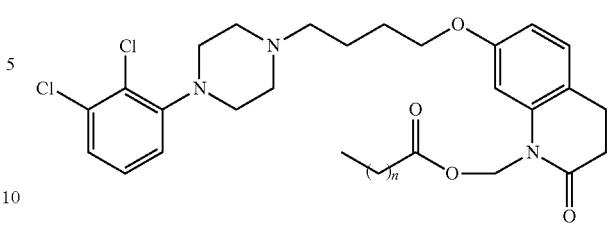

Formula 1 where n is zero or an integer less than 20. In a preferred embodiment, the aripiprazole prodrug has the formula described above where n=4 (aripiprazole cavoxil prodrug) or n=10 (aripiprazole lauroxil prodrug). In the above composition, the Dv90 of the composition may be less than about 1800 nm, preferably less than about 1500 nm and the Dv10 may be less than about 600 nm. Other exemplary particle sizes are described herein. It is preferred that the composition is size stable.

The at least one surface stabilizer may be selected from the group consisting of a polyoxyethylene sorbitan fatty acid ester (e.g. polysorbate 80, polysorbate 40, polysorbate 20), low molecular weight povidones, lecithin, d-alpha tocopheryl polyethylene glycol 1000 succinate, dioctyl sodium sulfosuccinate, or docusate sodium), methyl and propyl parabens, sorbitan monolaurate, carboxymethyl cellulose, hydroxypropylcellulose, sodium deoxycholate, akylsaccharides, difunctional block copolymers, d-alpha tocopheryl polyethylene glycol 1000 succinate, gelatin, albumin, lysozyme, cyclodextrins an example of which would be betahydroxcyclodextrin, and gel forming polymers. The aforementioned are considered preferable from a safety standpoint. Preferably, the at least one surface stabilizer is selected from the group consisting of carboxymethyl cellulose and polyoxyethylene sorbitan fatty acid esters. The aforementioned surface stabilizers have been demonstrated to be particularly effective in producing the stable composition of the present invention since the degree of particle size growth in compositions including the above surface stabilizers was found to be particularly low. More preferably, the surface stabilizer is a polyoxyethylene sorbitan fatty acid ester, for example polysorbate 20, since this is approved by the FDA for injectable use and was found to be particularly effective in producing stable compositions.

The composition of the present invention may comprise only one surface stabilizer, or may comprise a primary surface stabilizer and at least one secondary surface stabilizer. The use of one or more additional surface stabilizers may improve the stability of the resulting composition and/or alter the in-vivo release of the aripiprazole pro-drug described herein.

A composition comprising more than one surface stabilizer may for example comprise a primary surface stabilizer which is polysorbate 20 and a secondary surface stabilizer which is pluronic F108 and/or components thereof (the individual components being polyoxyethylene and polyoxypropylene glycol). In such a composition, the aripiprazole prodrug formula n is equal to 4 (i.e. aripiprazole cavoxil), and the volume based particle distribution size (Dv50) of the aripiprazole particles is between 200 and 600 nm, preferably between 500 nm and 600 nm. In such a composition the overall free component (made up from the primary and secondary surface stabilizer) constitutes between 0.5% and 10%, preferably 0.5% and 3% (w/w) of the composition.

The quantity of surface stabilizer to be added to the composition may be expressed in terms of a ratio with respect to the quantity of aripiprazole prodrug in the composition by calculating the percentage (w/w) (of the total composition weight including any excipients) of the aripiprazole prodrug and the total percentage (w/w) (of the total composition weight including any excipients) of the surface stabilizer. If multiple surface stabilizers are present, the ratio takes into account all of the surface stabilizers present in the composition. The ratio of aripiprazole prodrug to surface stabilizer is between about 0.1:1 and about 40:1. The ratio of aripiprazole prodrug to surface stabilizer present in the composition may more specifically be between about 0.5:1 and about 38:1, about 1:1 and about 36:1, about 2:1 and about 34:1, about 2:1 and about 25:1, about 2:1 and about 20:1, about 4:1 and about 32:1, about 6:1 and about 30:1, about 8:1 and about 28:1, about 10:1 and about 26:1, about 10:1 and about 25:1, about 10:1 and about 20:1, about 12:1 and about 24:1, about 13:1 and about 23:1, about 14:1 and about 22:1, about 15:1 and about 21:1, about 16:1 and about 20:1, or about 17:1 and about 19:1. In a preferred embodiment, the ratio of aripiprazole prodrug to surface stabilizer present in the composition may more specifically lie within the range from about 15:1 to about 20:1. It has been found that this range provides the optimal quantity of adsorbed and free component of surface stabilizer for the purposes of producing a lead-in formulation. Even more preferably the ratio of aripiprazole prodrug to surface stabilizer present in the composition is about 17:1.

In a composition having a volume based particle size (Dv50) of less than about 900 nm in size, the ratio of aripiprazole prodrug to surface stabilizer present in the composition may be between about 0.5:1 and about 38:1, about 1:1 and about 36:1, about 2:1 and about 34:1, about 2:1 and about 25:1, about 2:1 and about 20:1, about 4:1 and about 32:1, about 6:1 and about 30:1, about 8:1 and about 28:1, about 10:1 and about 26:1, about 10:1 and about 25:1, about 10:1 and about 20:1, about 12:1 and about 24:1, about 13:1 and about 23:1, about 14:1 and about 22:1, about 15:1 and about 21:1, about 16:1 and about 20:1 or between about 17:1 and about 19:1.

In a composition having a volume based particle size (Dv50) of less than about 800 nm in size, the ratio of aripiprazole prodrug to surface stabilizer present in the composition may be between about 0.5:1 and about 38:1, about 1:1 and about 36:1, about 2:1 and about 34:1, about 2:1 and about 25:1, about 2:1 and about 20:1, about 4:1 and about 32:1, about 6:1 and about 30:1, about 8:1 and about 28:1, about 10:1 and about 26:1, about 10:1 and about 25:1, about 10:1 and about 20:1, about 12:1 and about 24:1, about 13:1 and about 23:1, about 14:1 and about 22:1, about 15:1 and about 21:1, about 16:1 and about 20:1, or between about 17:1 and about 19:1.

In a composition having a volume based particle size (Dv50) of between about 50 and about 700 nm in size, the ratio of aripiprazole prodrug to surface stabilizer present in the composition may be between about 0.5:1 and about 38:1, about 1:1 and about 36:1, about 2:1 and about 34:1, about 2:1 and about 25:1, about 2:1 and about 20:1, about 4:1 and about 32:1, about 6:1 and about 30:1, about 8:1 and about 28:1, about 10:1 and about 26:1, about 10:1 and about 25:1, about 10:1 and about 20:1, about 12:1 and about 24:1, about 13:1 and about 23:1, about 14:1 and about 22:1, about 15:1 and about 21:1, about 16:1 and about 20:1, or between about 17:1 and about 19:1.

In a composition having a volume based particle size (Dv50) of less than about 700 nm in size, the ratio of aripiprazole prodrug to surface stabilizer present in the composition may be between about 0.5:1 and about 38:1, about 1:1 and about 36:1, about 2:1 and about 34:1, about 2:1 and about 25:1, about 2:1 and about 20:1, about 4:1 and about 32:1, about 6:1 and about 30:1, about 8:1 and about 28:1, about 10:1 and about 26:1, about 10:1 and about 25:1, about 10:1 and about 20:1, about 12:1 and about 24:1, about 13:1 and about 23:1, about 14:1 and about 22:1, about 15:1 and about 21:1, about 16:1 and about 20:1, or between about 17:1 and about 19:1.

In a composition having a volume based particle size (Dv50) of less than about 600 nm in size, the ratio of aripiprazole prodrug to surface stabilizer present in the composition may be between about 0.5:1 and about 38:1, about 1:1 and about 36:1, about 2:1 and about 34:1, about 2:1 and about 25:1, about 2:1 and about 20:1, about 4:1 and about 32:1, about 6:1 and about 30:1, about 8:1 and about 28:1, about 10:1 and about 26:1, about 10:1 and about 25:1, about 10:1 and about 20:1, about 12:1 and about 24:1, about 13:1 and about 23:1, about 14:1 and about 22:1, about 15:1 and about 21:1, about 16:1 and about 20:1, or between about 17:1 and about 19:1.

In a composition having a volume based particle size (Dv50) of less than about 500 nm in size, the ratio of aripiprazole prodrug to surface stabilizer present in the composition may be between about 0.5:1 and about 38:1, about 1:1 and about 36:1, about 2:1 and about 34:1, about 2:1 and about 25:1, about 2:1 and about 20:1, about 4:1 and about 32:1, about 6:1 and about 30:1, about 8:1 and about 28:1, about 10:1 and about 26:1, about 10:1 and about 25:1, about 10:1 and about 20:1, about 12:1 and about 24:1, about 13:1 and about 23:1, about 14:1 and about 22:1, about 15:1 and about 21:1, about 16:1 and about 20:1, or between about 17:1 and about 19:1.

In a composition having a volume based particle size (Dv50) of less than about 400 nm in size, the ratio of aripiprazole prodrug to surface stabilizer present in the composition may be between about 0.5:1 and about 38:1, about 1:1 and about 36:1, about 2:1 and about 34:1, about 2:1 and about 25:1, about 2:1 and about 20:1, about 4:1 and about 32:1, about 6:1 and about 30:1, about 8:1 and about 28:1, about 10:1 and about 26:1, about 10:1 and about 25:1, about 10:1 and about 20:1, about 12:1 and about 24:1, about 13:1 and about 23:1, about 14:1 and about 22:1, about 15:1 and about 21:1, about 16:1 and about 20:1, or between about 17:1 and about 19:1.

In a composition having a volume based particle size (Dv50) of between 175 and 350 nm in size, the ratio of aripiprazole prodrug to surface stabilizer present in the composition may be between about 0.5:1 and about 38:1, about 1:1 and about 36:1, about 2:1 and about 34:1, about 2:1 and about 25:1, about 2:1 and about 20:1, about 4:1 and about 32:1, about 6:1 and about 30:1, about 8:1 and about 28:1, about 10:1 and about 26:1, about 10:1 and about 25:1, about 10:1 and about 20:1, about 12:1 and about 24:1, about 13:1 and about 23:1, about 14:1 and about 22:1, about 15:1 and about 21:1, about 16:1 and about 20:1, or between about 17:1 and about 19:1.

In a composition having a volume based particle size (Dv50) of less than about 300 nm in size, the ratio of aripiprazole prodrug to surface stabilizer present in the composition may be between about 0.5:1 and about 38:1, about 1:1 and about 36:1, about 2:1 and about 34:1, about 2:1 and about 25:1, about 2:1 and about 20:1, about 4:1 and about 32:1, about 6:1 and about 30:1, about 8:1 and about 28:1, about 10:1 and about 26:1, about 10:1 and about 25:1, about 10:1 and about 20:1, about 12:1 and about 24:1, about 13:1 and about 23:1, about 14:1 and about 22:1, about 15:1 and about 21:1, about 16:1 and about 20:1, or between about 17:1 and about 19:1.

In a composition having a volume based particle size (Dv50) of less than about 200 nm in size, the ratio of aripiprazole prodrug to surface stabilizer present in the composition may be between about 0.5:1 and about 38:1, about 1:1 and about 36:1, about 2:1 and about 34:1, about 2:1 and about 25:1, about 2:1 and about 20:1, about 4:1 and about 32:1, about 6:1 and about 30:1, about 8:1 and about 28:1, about 10:1 and about 26:1, about 10:1 and about 25:1, about 10:1 and about 20:1, about 12:1 and about 24:1, about 13:1 and about 23:1, about 14:1 and about 22:1, about 15:1 and about 21:1, about 16:1 and about 20:1, or between about 17:1 and about 19:1.

In a composition having a volume based particle size (Dv50) of less than about 100 nm in size, the ratio of aripiprazole prodrug to surface stabilizer present in the composition may be between about 0.5:1 and about 38:1, about 1:1 and about 36:1, about 2:1 and about 34:1, about 2:1 and about 25:1, about 2:1 and about 20:1, about 4:1 and about 32:1, about 6:1 and about 30:1, about 8:1 and about 28:1, about 10:1 and about 26:1, about 10:1 and about 25:1, about 10:1 and about 20:1, about 12:1 and about 24:1, about 13:1 and about 23:1, about 14:1 and about 22:1, about 15:1 and about 21:1, about 16:1 and about 20:1, or between about 17:1 and about 19:1.

The abovementioned ratio of active to surface stabilizer is selected such that the appropriate level of free surface stabilizer is provided. The level of free surface stabilizer available should be sufficiently high enough to achieve the desired modulation in pharmacokinetic properties, particularly onset time. However, the overall level of surface stabilizer in the composition is preferably low enough as to avoid toxicity problems or injection site reactions in patients. It is preferred that the free component of the at least one surface stabilizer constitutes greater than 0% (w/w) and no more than about 3% (w/w) of the composition (i.e. the overall weight of the composition including the active, surface stabilizer and any other excipients added to the composition) as free surface stabilizer amounts in this range provide optimal reduction in onset time whilst also being at a level which is preferable from a toxicity perspective. The level of free surface stabilizer may for example lie within the range of about 0.1 to about 2.9%, about 0.1 to about 2.7%, about 0.1 to about 2.6%, about 0.1 to about 2.4%, about 0.1 to about 2.2%, about 0.1 to about 2%, about 0.1 to about 1.8%, about 0.1 to about 1.4%, about 0.1 to about 1.2%, about 0.1 to about 1%, about 0.1 to about 0.8%, about 0.1 to about 0.6%, about 0.1 to about 0.4%. More preferably, the quantity of free surface stabilizer is within the range about 0.1% to about 1.6%, as this particular range has been found to produce a significant reduction in the onset time whilst at the same time ensuring that the level of surface stabilizer present is well within tolerable levels.

In a composition having a volume based particle size (Dv50) of less than about 900 nm in size, the level of free surface stabilizer may for example lie within the range of about 0.1 to about 2.9%, about 0.1 to about 2.7%, about 0.1 to about 2.6%, about 0.1 to about 2.4%, about 0.1 to about 2.2%, about 0.1 to about 2%, about 0.1 to about 1.8%, about 0.1 to about 1.4%, about 0.1 to about 1.2%, about 0.1 to about 1%, about 0.1 to about 0.8%, about 0.1 to about 0.6%, and about 0.1 to about 0.4% (w/w) of the composition.

In a composition having a volume based particle size (Dv50) of less than about 800 nm in size, the level of free surface stabilizer may for example lie within the range of about 0.1 to about 2.9%, about 0.1 to about 2.7%, about 0.1 to about 2.6%, about 0.1 to about 2.4%, about 0.1 to about 2.2%, about 0.1 to about 2%, about 0.1 to about 1.8%, about 0.1 to about 1.4%, about 0.1 to about 1.2%, about 0.1 to about 1%, about 0.1 to about 0.8%, about 0.1 to about 0.6%, and about 0.1 to about 0.4% (w/w) of the composition.

In a composition having a volume based particle size (Dv50) of between 50 and 700 nm in size, the level of free surface stabilizer may for example lie within the range of about 0.1 to about 2.9%, about 0.1 to about 2.7%, about 0.1 to about 2.6%, about 0.1 to about 2.4%, about 0.1 to about 2.2%, about 0.1 to about 2%, about 0.1 to about 1.8%, about 0.1 to about 1.4%, about 0.1 to about 1.2%, about 0.1 to about 1%, about 0.1 to about 0.8%, about 0.1 to about 0.6%, and about 0.1 to about 0.4% (w/w) of the composition.

In a composition having a volume based particle size (Dv50) of less than about 700 nm in size, the level of free surface stabilizer may for example lie within the range of about 0.1 to about 2.9%, about 0.1 to about 2.7%, about 0.1 to about 2.6%, about 0.1 to about 2.4%, about 0.1 to about 2.2%, about 0.1 to about 2%, about 0.1 to about 1.8%, about 0.1 to about 1.4%, about 0.1 to about 1.2%, about 0.1 to about 1%, about 0.1 to about 0.8%, about 0.1 to about 0.6%, and about 0.1 to about 0.4% (w/w) of the composition.

In a composition having a volume based particle size (Dv50) of less than about 600 nm in size, the level of free surface stabilizer may for example lie within the range of about 0.1 to about 2.9%, about 0.1 to about 2.7%, about 0.1 to about 2.6%, about 0.1 to about 2.4%, about 0.1 to about 2.2%, about 0.1 to about 2%, about 0.1 to about 1.8%, about 0.1 to about 1.4%, about 0.1 to about 1.2%, about 0.1 to about 1%, about 0.1 to about 0.8%, about 0.1 to about 0.6%, and about 0.1 to about 0.4% (w/w) of the composition.

In a composition having a volume based particle size (Dv50) of less than about 500 nm in size, the level of free surface stabilizer may for example lie within the range of about 0.1 to about 2.9%, about 0.1 to about 2.7%, about 0.1 to about 2.6%, about 0.1 to about 2.4%, about 0.1 to about 2.2%, about 0.1 to about 2%, about 0.1 to about 1.8%, about 0.1 to about 1.4%, about 0.1 to about 1.2%, about 0.1 to about 1%, about 0.1 to about 0.8%, about 0.1 to about 0.6%, and about 0.1 to about 0.4% (w/w) of the composition.

In a composition having a volume based particle size (Dv50) of less than about 400 nm in size, the level of free surface stabilizer may for example lie within the range of about 0.1 to about 2.9%, about 0.1 to about 2.7%, about 0.1 to about 2.6%, about 0.1 to about 2.4%, about 0.1 to about 2.2%, about 0.1 to about 2%, about 0.1 to about 1.8%, about 0.1 to about 1.4%, about 0.1 to about 1.2%, about 0.1 to about 1%, about 0.1 to about 0.8%, about 0.1 to about 0.6%, and about 0.1 to about 0.4% (w/w) of the composition.

In a composition having a volume based particle size (Dv50) of between about 175 and about 350 nm in size, the level of free surface stabilizer may for example lie within the range of about 0.1 to about 2.9%, about 0.1 to about 2.7%, about 0.1 to about 2.6%, about 0.1 to about 2.4%, about 0.1 to about 2.2%, about 0.1 to about 2%, about 0.1 to about 1.8%, about 0.1 to about 1.4%, about 0.1 to about 1.2%, about 0.1 to about 1%, about 0.1 to about 0.8%, about 0.1 to about 0.6%, and about 0.1 to about 0.4% (w/w) of the composition.

In a composition having a volume based particle size (Dv50) of less than about 300 nm in size, the level of free surface stabilizer may for example lie within the range of about 0.1 to about 2.9%, about 0.1 to about 2.7%, about 0.1 to about 2.6%, about 0.1 to about 2.4%, about 0.1 to about 2.2%, about 0.1 to about 2%, about 0.1 to about 1.8%, about 0.1 to about 1.4%, about 0.1 to about 1.2%, about 0.1 to about 1%, about 0.1 to about 0.8%, about 0.1 to about 0.6%, and about 0.1 to about 0.4% (w/w) of the composition.

In a composition having a volume based particle size (Dv50) of less than about 200 nm in size, the level of free surface stabilizer may for example lie within the range of about 0.1 to about 2.9%, about 0.1 to about 2.7%, about 0.1 to about 2.6%, about 0.1 to about 2.4%, about 0.1 to about 2.2%, about 0.1 to about 2%, about 0.1 to about 1.8%, about 0.1 to about 1.4%, about 0.1 to about 1.2%, about 0.1 to about 1%, about 0.1 to about 0.8%, about 0.1 to about 0.6%, and about 0.1 to about 0.4% (w/w) of the composition.

In a composition having a volume based particle size (Dv50) of less than about 100 nm in size, the level of free surface stabilizer may for example lie within the range of about 0.1 to about 2.9%, about 0.1 to about 2.7%, about 0.1 to about 2.6%, about 0.1 to about 2.4%, about 0.1 to about 2.2%, about 0.1 to about 2%, about 0.1 to about 1.8%, about 0.1 to about 1.4%, about 0.1 to about 1.2%, about 0.1 to about 1%, about 0.1 to about 0.8%, about 0.1 to about 0.6%, and about 0.1 to about 0.4% (w/w) of the composition.

The volume based particle size (Dv50) may be less than about 1000 nm, less than about 950 nm, less than about 900 nm, less than about 850 nm, less than about 800 nm, less than about 750 nm, less than about 700 nm, less than about 650 nm, less than about 600 nm, less than about 550 nm, less than about 500 nm, less than about 450 nm, less than about 400 nm, less than about 350 nm, less than about 300 nm, less than about 250 nm, less than about 200 nm, less than about 150 nm, less than about 100 nm, or less than about 50 nm. In a preferred embodiment, the volume based particle size (Dv50) of the aripiprazole prodrug particles is between about 50 nm and 700 nm, more preferably between about 175 nm and about 350 nm In any of the compositions described above, where the Dv50 is less than about 900 nm, the Dv90 may be less than about 1700 nm, less than about 1600 nm, less than about 1500 nm, less than about 1400 nm, less than about 1300 nm, less than about 1200 nm, less than about 1100 nm and less than about 1000 nm. The Dv10 may be less than about 850 nm, less than about 800 nm, less than about 700 nm, less than about 600 nm, less than about 500 nm, less than about 400 nm, less than about 300 nm, less than about 200 nm, and less than about 100 nm.

Where the Dv50 is less than about 800 nm, the Dv90 may be less than about 1600 nm, less than about 1500 nm, less than about 1400 nm, less than about 1300 nm, less than about 1200 nm, less than about 1100 nm, less than about 1000 nm and less than about 900 nm. The Dv10 may be less than about 750 nm, less than about 700 nm, less than about 600 nm, less than about 500 nm, less than about 400 nm, less than about 300 nm, less than about 200 nm, and less than about 100 nm.

Where the Dv50 is less than about 700 nm, the Dv90 may be less than about 1500 nm, less than about 1400 nm, less than about 1300 nm, less than about 1200 nm, less than about 1100 nm, less than about 1000 nm, less than about 900 nm and less than about 800 nm. The Dv10 may be less than about 650 nm, less than about 600 nm, less than about 500 nm, less than about 400 nm, less than about 300 nm, less than about 200 nm, and less than about 100 nm.

Where the Dv50 is less than about 600 nm, the Dv90 may be less than about 1500 nm, less than about 1400 nm, less than about 1300 nm, less than about 1200 nm, less than about 1100 nm, less than about 1000 nm, less than about 900 nm and less than about 800 nm, and less than about 700 nm. The Dv10 may be less than about 550 nm, less than about 500 nm, less than about 400 nm, less than about 300 nm, less than about 200 nm and less than about 100 nm.

Where the Dv50 is less than about 500 nm, the Dv90 may be less than about 1500 nm, less than about 1400 nm, less than about 1300 nm, less than about 1200 nm, less than about 1100 nm, less than about 1000 nm, less than about 900 nm and less than about 800 nm, less than about 700 nm, and less than about 600 nm. The Dv10 may be less than about 450 nm, less than about 400 nm, less than about 300 nm, less than about 200 nm, and less than about 100 nm.

Where the Dv50 is less than about 400 nm, the Dv90 may be less than about 1500 nm, less than about 1400 nm, less than about 1300 nm, less than about 1200 nm, less than about 1100 nm, less than about 1000 nm, less than about 900 nm and less than about 800 nm, less than about 700 nm, less than about 600 nm, and less than about 500 nm. The Dv10 may be less than about 350 nm, less than about 300 nm, less than about 200 nm and less than about 100 nm.

Where the Dv50 is less than about 300 nm, the Dv90 may be less than about 1500 nm, less than about 1400 nm, less than about 1300 nm, less than about 1200 nm, less than about 1100 nm, less than about 1000 nm, less than about 900 nm and less than about 800 nm, less than about 700 nm, less than about 600 nm, and less than about 500 nm, and less than about 400 nm. The Dv10 may be less than about 250 nm, less than about 200 nm and less than about 100 nm.

Where the Dv50 is less than about 200 nm, the Dv90 may be less than 1500 nm, less than about 1400 nm, less than about 1300 nm, less than about 1200 nm, less than about 1100 nm, less than about 1000 nm, less than about 900 nm and less than about 800 nm, less than about 700 nm, less than about 600 nm, and less than about 500 nm, and less than about 400 nm, and less than about 300 nm. The Dv10 may be less than about 150 nm, less than about 100 nm and less than about 50 nm.

Where the Dv50 is less than about 100 nm, the Dv90 may be less than about 1000 nm, less than about 900 nm and less than about 800 nm, less than about 700 nm, less than about 600 nm, and less than about 500 nm, and less than about 400 nm, and less than about 300 nm and less than about 200 nm. The Dv10 may be less than about 50 nm.

The composition may be formulated as a depot injection. This is the preferred route of administration in order to ensure the long acting release of aripiprazole. Some depot compositions are designed to deliver the drug over a period of several weeks or months. In this way the drug may be delivered in a controlled fashion over a prolonged period. Where the composition is to be used as a lead in composition (in combination with a separate long acting injectable), presenting the composition as a depot injection offers a potential benefit over other routes of administration (e.g. oral lead in) because of the potential to simplify the dosing regimen by reducing the frequency of the dosing administration. In one embodiment, the depot composition of the present invention can be administered once in order to cover an entire lead in period which aids patient compliance, particularly useful in the context of the patient population to which aripiprazole is aimed. In particular, aripiprazole is an atypical antipsychotic prescribed for treating, for example, subjects with depression, schizophrenia and bipolar disorder. Such subjects may have difficulty complying with multi-step drug dosing schedules; the simplest dosing regimen is likely to obtain the highest percentage of patient compliance.

Preferably, the depot injection is provided in an injection device such as a pre-filled single or dual chambered syringe. This provides a much simpler and faster means of administering the composition without the need for additional steps such as reconstituting a powder into a dispersion etc.

The composition of the invention may be formulated as a powder for reconstitution in a liquid medium, wherein the population of aripiprazole prodrug particles redisperse in the liquid medium such that the redispersed aripiprazole prodrug particles have a volume based particle size (Dv50) of less than about 1000 nm.

The composition of the invention may comprise a second population of aripiprazole prodrug particles, the second population having a volume based particle size (Dv50) of about 5000 nm or greater. Combining the composition of the present invention with a larger particle size composition results in a bimodal or multi-modal composition which can combine the advantages of fast onset of action and long acting therapeutic effect. It was surprisingly discovered that a bimodal or multimodal composition of aripiprazole prodrug did not experience particle size instability which commonly occurs with multi-modal compositions of other active ingredients. This second population may have a volume based particle size (Dv50) range of between about 15 μm and about 25 μm.

The composition may comprise an additional atypical antipsychotic other than the aripiprazole prodrug used with the present invention.

The present application also relates to a method of treating a condition in a mammal selected from schizophrenia, bipolar I disorder, major depressive disorder (MDD), autistic disorder, agitation associated with schizophrenia or bipolar I disorder. The method comprises administering a therapeutically effective amount of a composition as described herein to a mammal in need thereof. Said method may include administering a composition which is tailored to provide a therapeutic level of aripiprazole over at least about 30 days (the lead-in period). Alternatively, the lead-in period may be at least about 15 days, at least about 25 days, at least about 30 days, or any time point in between these values. This method simplifies the dosage regime associated with administering a lead in composition to a patient and eliminates the requirement to take an oral dose on a daily basis. The method may further include administering a composition of aripiprazole prodrug having a volume based particle size (Dv50) of greater than about 5000 nm, which can be carried out by co-administering the compositions (the respective compositions are administered at about the same time; as separate compositions) or by administering the respective compositions together as a single composition. Alternatively, the method may include administering a composition which is tailored to maintain a therapeutic level of aripiprazole in the blood for no more than about 13 days and re-administering the composition at an appropriate time point thereafter.

The present invention also relates to methods of improving initial in vivo pharmacokinetic release profiles by providing a population of aripiprazole prodrugs having a volume based particle distribution size (Dv50) between about 350 and about 175 nm as determined by light scattering techniques, wherein the 17:1 ratio of said particles to polysorbate (most preferably polysorbate 20) achieves a therapeutic concentration of aripiprazole in less than seven days. In a preferred embodiment the population of aripiprazole prodrugs has a volume based particle distribution size (Dv50) of less than about 400 nm, less than about 300 nm, less than about 200 nm and/or less than about 100 nm. In a further preferred embodiment, the ratio of said particles to polysorbate 20 achieves a therapeutic concentration of aripiprazole in less than about 72 hours, about 48 hours and/or about 24 hours.

DETAILED DESCRIPTION OF THE INVENTION

Figure 1:
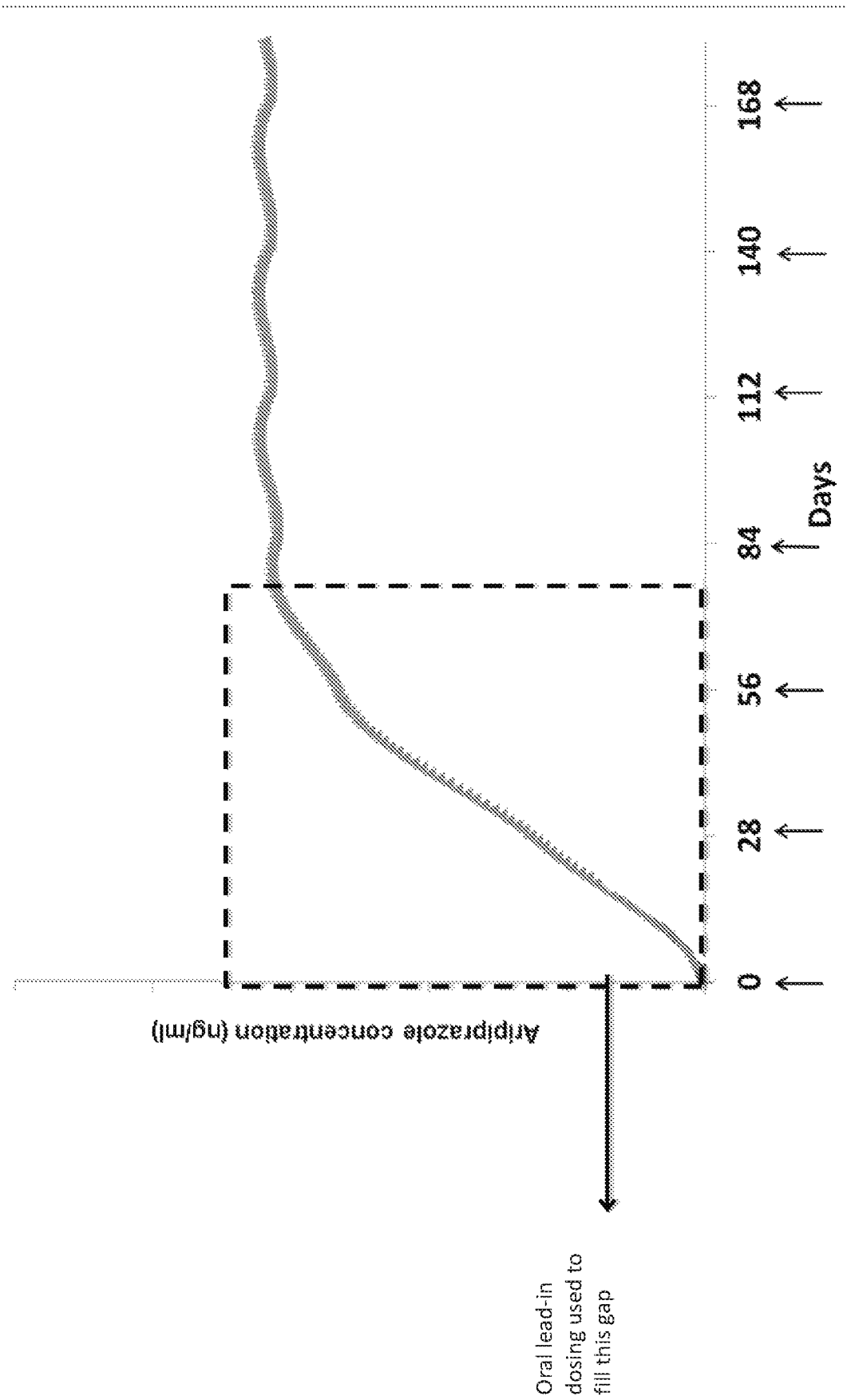
FIG. 1 is a prior art graphical representation of an induction period experienced with a 20 μm aripiprazole lauroxil formulation.

The present invention is described herein using several definitions, as set forth below and throughout the application.

As used herein, "about" will be understood by persons of ordinary skill in the art and will vary to some extent on the context in which it is used. If there are uses of the term which are not clear to persons of ordinary skill in the art given the context in which it is used, "about" will mean up to plus or minus 10% of the particular term.

A "long acting injectable" or "depot" injection is an injectable composition (usually subcutaneous or intramuscular) which upon injection forms a reservoir of the drug substance within the body of the subject from which the drug is slowly distributed into systemic circulation. In this way the drug may be delivered in a controlled fashion over a prolonged period. As defined herein, a depot injection releases the aripiprazole prodrug over an extended period of time, at least about 24 hours and preferably about 1 week or more.

The term "injection site reaction" as used herein refers to any adverse physiological response around the site of needle entry after injection.

The term "lead in composition" as used herein refers to a formulation of an active agent which reduces or eliminates the "lead in" period as referenced below. In other words, a lead in composition acts to increase the active agent levels during the lead in period over and above the level of what would be observed in the absence of the lead in composition. This may also be referred to as a loading dose.

The term "lead in" or "lead in period" as used herein refers to a period of time following administration of an active agent to a subject before the level of active agent in systemic circulation reaches a therapeutically effective amount for the mammalian subject to which it is dosed.

The term "particle size" or "volume based particle size" or "volume based particle size distribution" as used herein is equivalent to and also referred to as the Dv50 or D50 and means that at least about 50% of the aripiprazole prodrug particles have a diameter of less than the size specified. The aforementioned terms are used interchangeably herein. For example a volume based particle size (Dv50) of less than 1000 nm, means that 50% of the particle population has a diameter of less than 1000 nm when measured by static or dynamic light scattering techniques known to those skilled in the art. Since the particles of the present invention tend to be irregular in shape, an approximation of the particle size is made on the basis of the volume based particle size, which specifies the diameter of the sphere that has same volume as a given particle. Unless otherwise specified, all particle sizes are specified in terms of volume based measurements and are measured by laser light scattering/diffraction. Particle sizes are then determined based on Mie scattering theory. More specifically, unless otherwise specified, volume based particle size (Dv50) is determined using a Horiba LA-950 standard model laser particle size analyser. Deionized water or water with a small quantity (for example 0.1% w/w) of surface stabilizer (for example polysorbate 20) is used as the sizing medium unless otherwise specified. The terms "D90" and "D10" mean that, respectively at least about 90% and 10% of the aripiprazole prodrug particles have a diameter of less than the size specified. These may also be referred to as "Dv90" and "Dv10" respectively, and these terms are used interchangeably herein.

The term "mean particle size" is essentially the same as "volume mean diameter" and in the present application this is defined in the same manner as defined in the Horiba Scientific brochure, "A guidebook to particle size analysis" (2012), available from Horiba's website, www.horiba.com. The calculation is expressed by conceptualizing a histogram table showing the upper and lower limits of n size channels along with the percent within each channel. The Di value for each channel is the geometric mean, the square root of upper×lower diameters. For the numerator take the geometric Di to the fourth power×the percent in that channel, summed over all channels. For the denominator take the geometric Di to the third power×the percent in that channel, summed over all channels. The volume mean diameter is referred to by several names including D[4,3].

$$D[4,3] = \frac{\sum_i^n D_i^4 v_i}{\sum_i^n D_i^3 v_i}$$

The skilled person will appreciate that particle size can also be determined by other suitable measurement means, such as by volume, number, etc.), and can be measured by, for example, sedimentation flow fractionation, dynamic light scattering, disk centrifugation, and other techniques known in the art. A full description of dynamic and static light scattering techniques is provided from pages 121-131 of "Nanoparticle technology for drug delivery" by Ram B. Gupta and Uday B. Kompella, published by Taylor & Franceis Group (ISBN 1-57444-857-9) and pages 569-580 of "Pharmaceutics, the science of dosage form design" edited by Michael E. Aulton and published by Churchill Livingstone (ISBN: 0-443-03643-8). It is intended that the definition of particle size as specified in the claims should cover measurements using any technique used in the art for particle size characterisation.

A "prodrug" is a therapeutically inactive molecule which can be physiologically metabolized into an active pharmaceutical ingredient. The terms "drug" or "active agent," when used herein, typically refers to aripiprazole (the metabolite) but may, if clearly indicated by its context, refer to another drug.

A "size stable" composition is a composition that exhibits no flocculation or particle agglomeration visible to the naked eye at least about 15 minutes, and preferably at least about two days or longer after preparation. Preferably, a "size stable" composition is a composition where the volume based particle size (Dv50) and/or mean particle size does not increase by any more than about 400 nm when the composition is stored at about 20° C. for a period of about 24 hours. More preferably, a "size stable" composition is where the volume based particle size (Dv50) and/or mean particle size does not increase by any more than about 400 nm when the composition is stored at about 40° C. for a period of about 6 months. Most preferably, a "size stable" composition is where the volume based particle size (Dv50) and/or mean particle size does not increase by any more than about 100 nm when the composition is stored at about 40° C. for a period of about 6 months.

As used herein, the term "subject" is used to mean an animal, preferably a mammal, including a human or non-human. The terms patient and subject may be used interchangeably.

The term "therapeutically effective amount" refers to the minimum blood concentration of aripiprazole in order to have a therapeutic effect. This may vary depending on the type of subject. In the case of humans, the US Food and Drug Administration summary basis of approval document for Abilify Maintena defines this value as 94 ng/mL. Unless otherwise indicated this value in relation to humans is defined herein as at least about 34-about 50 ng/mL, and preferably about 94 ng/mL.

The terms "treatment," "therapy," "therapeutic" and the like, as used herein, encompass any course of medical intervention aimed at a pathologic condition, and includes not only permanent cure of a disease, but prevention of disease, control or even steps taken to mitigate a disease or disease symptoms.

Relationship Between Free Surface Stabilizer and Initial In-Vivo Release

The composition of the present invention comprises stabilized aripiprazole particles (particles having a surface stabilizer adsorbed to the surface thereof to mitigate against drug particle aggregation and/or crystal growth) having a volume based particle size (Dv50) of less than about 1000 nm and a free component of surface stabilizer. It was surprisingly discovered that the combination of these features i.e., stabilized aripiprazole particle size to free surface stabilizer ratio results in a significantly enhanced pharmacokinetic profile in comparison to aripiprazole compositions which do not include these features.

By appropriate selection of the stabilized aripiprazole particle size and the level of free surface stabilizer, the composition of the present invention can be tailored to achieve an in vivo release profile based on a given dosage application. For example, appropriate selection of the stabilized aripiprazole particle size and level of free surface stabilizer can provide a significant modulation of the pharmacokinetic profile by providing a shorter time to $T_{max}$ and onset time (i.e. period of time after administration before the active reaches a therapeutic concentration in the blood). In order to ensure that sufficient free component of surface stabilizer will be present in the composition of the present invention, a sufficient quantity (in excess of that required to stabilize particles) of surface stabilizer must be added to the composition. The total amount of surface stabilizer added must take account the aripiprazole prodrug particle size. It is the combination of features i.e., stabilized aripiprazole particle size to free stabilizer ratio that modulates the desired rate of aripiprazole release as described in FIGS. 16-22 and Table 13 of Example 8.

As defined herein, a lead in pharmacokinetic profile may be defined as any in vivo pharmacokinetic release profile in human or mammalian subjects which achieves a therapeutic concentration in the blood of less than about 1 week, preferably less than about 72 hours, more preferably less than about 48 hours and more preferably less than about 24 hours, and which maintains a therapeutic level for at least about 1 week, preferably about 2 weeks and more preferably about 3 weeks.

Without being bound to theory, a possible mechanism by which the free surface stabilizer modifies the in vivo pharmacokinetic release profile of the composition described herein is through assisting or increasing the solubility of the aripiprazole prodrug. One mechanism by which it may do so is by forming micelles containing solubilized drug. This ensures that a greater proportion of the prodrug can be solubilised in a given time period. Another possible mechanism of action is that after the prodrug composition is administered (e.g. by intramuscular depot injection), particles have a tendency to aggregate in the muscle tissue and the presence of a free surface stabilizer component reduces, slows or prevents such aggregation from occurring, thus speeding up distribution and ultimately absorption.

It is particularly preferred that the volume based particle size (Dv50) of the aripiprazole prodrug composition of the present invention be within the range of about 50 nm to about 750 nm, and that the ratio of drug to surface stabilizer in the composition lies within the range of about 17:1 to about 26:1. Preferably, the volume based particle size (Dv50) of the aripiprazole prodrug composition of the present invention be within the range of about 350 nm and about 175 nm. Even more preferably, compositions provide a free surface stabilizer amount within the range of about 1% to about 1.6% (w/w).

The composition of the present invention may be tailored as a lead in composition to a conventional long acting antipsychotic formulation, in order to address any delay in onset which may occur with such formulations. The present composition can be used as a lead in in conjunction with any long acting atypical antipsychotic (for example Abilify Maintena®) to address any delay in onset experienced with these formulations. The preferred use of the present invention is as a lead in for the aripiprazole prodrugs as described herein.

Compositions of the Present Invention

The composition of the present invention comprises certain aripiprazole prodrugs which are described in U.S. Pat. No. 8,431,576, which is specifically incorporated by reference. In particular, the aripiprazole prodrug referenced in relation to the present invention has the general formula:

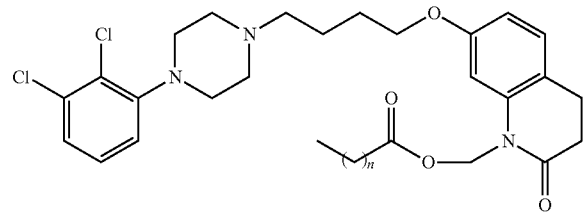

where n is any whole number greater than or equal to 0 and less than 20. In the preferred embodiments discussed below, n is equal to 4 or 10.

One such compound is aripiprazole hexanoate (in this case n=4), the USAN term for which is aripiprazole cavoxil. Aripirazole cavoxil is the N-hexanoyloxymethyl prodrug of aripiprazole and has the following structure.

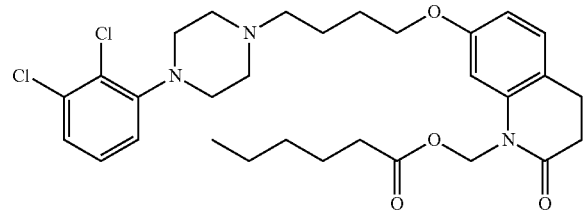 [SMILES: CCCCCC(=O)OCN1C(=O)CCc2ccc(OCCCCN3CCN(c4cccc(Cl)c4Cl)CC3)cc21]

The above compound may be described by the chemical name (7-(4-(4-(2,3-Dichlorophenyl)piperazin-1-yl)butoxy)-2-oxo-3,4-dihydroquinolin-1(2H) yl)methyl hexanoate and the molecular formula $C_{30}H_{39}Cl_2N_3O_4$. The molecule has the CAS registry number 1259305-26-4.

Another such compound is aripiprazole laurate (in this case n=10). The USAN term for which is aripiprazole lauroxil. Aripirazole lauroxil is the N-lauroyloxymethyl prodrug of aripiprazole and has the following structure:

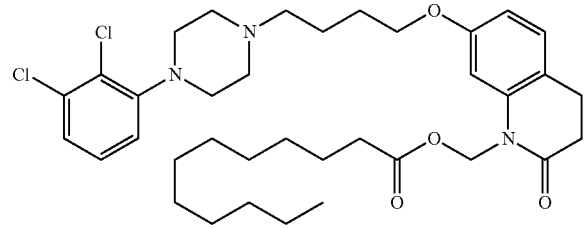 [SMILES: CCCCCCCCCCCC(=O)OCN1C(=O)CCc2ccc(OCCCCN3CCN(c4cccc(Cl)c4Cl)CC3)cc21]

This above compound can be described by the chemical name Dodecanoic acid, [7-[4-[4-(2,3-dichlorophenyl)-1-piperazinyl]butoxy]-3,4-dihydro-2-oxo-1(2H)-quinolinyl] methyl ester and the molecular formula $C_{36}H_{51}Cl_2N_3O_4$. The molecule has the CAS registry number 1259305-29-7.

Aripiprazole lauroxil is a long acting injectable indicated for schizophrenia developed by Alkermes Pharma Ireland Limited in the form of a microcrystalline suspension having a particle size in the order of about 20 µm.

Dosage Forms and Administration of the Present Invention

The composition of the present invention may also be formulated as a dosage form to be administered about once a week. A once-weekly dosage regimen according to the present invention can be provided in the form of an intramuscular depot injection, which can be provided as a re-constitutable powder or provided in an injection device such as a pre-filled syringe.

A once-weekly dosage form may be defined as a dosage that provides an in vivo pharmacokinetic profile in human or mammalian subjects characterised by achieving a therapeutic concentration in the blood in less than about 72 hours and which maintains a therapeutic level for a minimum of about 5 days and a maximum of about 13 days. Preferably, a once weekly dosage form when dosed in a mammalian subject reaches a therapeutic concentration in the blood of the subject in less than about 36 hours and maintains a therapeutic level in the blood of the subject for a minimum of about 5 days and a maximum of about 9 days.

The composition may also be formulated for administration once every two weeks or once every three weeks. An example of such a composition would reach a therapeutic concentration in the blood of the subject in less than about 7 days, and would maintain a concentration of aripiprazole which is above the therapeutic concentration for a minimum of about 14 days, preferably about 21 days and a maximum of about 28 days. Such a composition could provide an alternative dosing regimen which provides a structure for regular visits to a healthcare professional, but is less stringent and inconvenient for the patient than a once weekly dosing regimen.

The composition of the present invention may also be formulated as a long acting composition, which can maintain a therapeutic level of active in the blood for at least about 1 week and up to about 1 month. Accordingly the composition of the present invention can be tailored to a release profile serving as both a lead in and a long acting injectable in its own right.

The composition may also be formulated for administration once every two weeks or once every three weeks. An example of such a composition would reach a therapeutic concentration in the blood of the subject in less than about 7 days, and would maintain a concentration of aripiprazole which is above the therapeutic concentration for a minimum of about 14 days, preferably about 21 days and a maximum of about 28 days. Such a composition could provide an alternative dosing regimen which provides a structure for regular visits to a healthcare professional, but is less stringent and inconvenient for the patient than a once weekly dosing regimen.

The composition of the present invention may also be formulated for concurrent administration with an oral atypical antipsychotic, preferably Aripiprazole. Aripiprazole is commercially available in the United States under the brand name Abilify® (Abilify is a registered trademark of Otsuka Pharmaceutical Co., Ltd.), manufactured/marketed by Bristol-Myers Squibb of Princeton, N.J. and marketed by Otsuka America Pharmaceutical, Inc. Aripiprazole is available in tablet form, orally disintegrating tablet form and as an oral solution. In particular, the oral antipsychotic is dosed at 10 mg, 20 mg, 30 mg, 40 mg, 50 mg, 60 mg, 70 mg, 80 mg, 90 mg and/or 100 mg. Preferably, the oral antipsychotic is dosed at 30 mgs.

The composition of the present invention, in addition to having a population of particles with a volume based particle size (Dv50) of less than 1000 nm may also include a second larger particle size population of aripiprazole prodrug particles having a volume based particle size (Dv50) of about 5000 nm or greater. For example, a population of aripiprazole prodrug particles having a volume based particle size (Dv50) of 20 µm can be included in the composition of the present invention in order to provide the characteristics of a lead in composition as described earlier with a long acting release profile in a single composition.

This therefore leads to a simplified dosage regime since the lead in component which provides fast onset and therapeutic levels of aripiprazole in the blood thereafter for the duration of the lead in period and a long acting component, which reaches a therapeutic level in the blood after the lead in period and maintains the therapeutic level over a period of at least about 30 days. This ensures that a single composition maintains therapeutic concentration in the blood for a period of at least about 1 to about 30 days. The requirement for a separate lead in and long acting injection is therefore avoided, which has the direct consequence of simplifying the dosage regime and improving patient compliance.

It is considered surprising that a mixed population of particles can be produced as a stable composition at all. The present inventors have observed in relation to mixed populations of other active ingredients that where at least one of the populations has a small (less than about 2000 nm) volume based particle size (Dv50), both populations have a tendency to experience a change in particle size due to the effects of Ostwald ripening. Ostwald ripening is a phenomenon observed in small particle populations where multiple particle sizes are present. Typically, smaller particles dissolve then crystallise causing the larger particles present to grow. The phenomenon is relatively common with a large number of active agents, particularly active agents having a high solubility. Surprisingly, the incidence of Ostwald ripening in mixed populations of aripiprazole prodrug according to the present invention was observed to be very low when measured over a period of about 1 month. A possible explanation for this might lie in the fact that the present active agent has a particularly low aqueous solubility, meaning that particles of the active agent have a lower tendency to dissolve and recrystallize. This may be a unique property of hydrophobic materials: that the low surface free energies prevent particle size growth from occurring.

In another embodiment, the composition of the present invention, in addition to having an aripiprazole prodrug population of particle size less than 1000 nm, may include a second aripiprazole prodrug particle population having a volume based particle size (Dv50) which is less than 1000 nm in size, and at least about 100 nm, at least about 200 nm, at least about 300 nm, at least about 400 nm, at least about 500 nm, at least about 600 nm, at least about 700 nm, at least about 800 nm or at least about 900 nm greater than the Dv50 of the (first) aripiprazole prodrug population.

In another embodiment, the composition of the present invention may be delivered in a dual chamber syringe, in which one of the chambers is provided with a second aripiprazole prodrug composition having a different particle size. For example, the second aripiprazole composition may have a particle size which is also less than 1000 nm, between about 1000 and about 5000 nm or greater than about 5000 nm. Both compositions are thereby stored separately.

The composition of the present invention may be presented in the form of a particulate dispersion. The composition comprises a dispersion medium in which the population of aripiprazole prodrug particles is dispersed, and in which the free component of the surface stabilizer is dissolved or otherwise dispersed.

The composition of the present invention may additionally be provided as a dispersion (as described above). Such a dispersion may for example be provided in an injection device such as a pre-filled syringe. However, it should be understood that an injection device can include any device capable of delivering an injection which may be used with the present invention. For example, the compositions of the present invention may also be administered using an auto-injector device. Alternatively, the compositions of the present invention may be delivered using a needless syringe, or a dual-chamber syringe.

The composition of the present invention may be formulated as a powder for reconstitution in a liquid medium. A significant feature of the present invention in this regard is that the population of aripiprazole prodrug particles redisperse when reconstituted in a liquid medium such that the redispersed aripiprazole prodrug particles have a volume based particle size (Dv50) of less than 1000 nm.

One of ordinary skill will appreciate that effective amounts of aripiprazole prodrug can be determined empirically. Actual dosage levels of aripiprazole prodrug in the composition of the invention may be varied to obtain an amount of an aripiprazole prodrug that is effective to obtain a desired therapeutic response for a particular composition and method of administration. The selected dosage level therefore depends upon the desired therapeutic effect, the route of administration, the potency of aripiprazole prodrug, the desired duration of treatment, and other factors. Dosage unit compositions may contain such amounts of such submultiples thereof as may be used to make up the daily dose. It will be understood, however, that the specific dose level for any particular patient will depend upon a variety of factors: the type and degree of the cellular or physiological response to be achieved; activity of the specific agent or composition employed; the specific agents or composition employed; the age, body weight, general health, sex, and diet of the patient; the time of administration, route of administration, and rate of excretion of the agent; the duration of the treatment; drugs used in combination or coincidental with the specific agent; and like factors well known in the medical arts.

Surface Stabilizers

The composition of the invention comprises at least one surface stabilizer. However, combinations of more than one surface stabilizer have been found to be useful and can be used in the invention. Where a plurality of surface stabilizers is used there may be a primary surface stabilizer that is present in greater concentration than the other (secondary) surface stabilizer(s).

Without being restricted to theory, it is believed that the surface stabilizer functions by forming a steric barrier or an electrostatic barrier around the drug particles, thereby providing enough physical separation of the particles to prevent particle aggregation. Several compounds are known to possess the properties of forming such a steric or electrostatic barrier when applied to small particles. It is therefore plausible that any one of these substances could function as a surface stabilizer in the context of the present invention and therefore fall within the scope of the invention. The term surface stabilizer may be used interchangeably with the term surface modifier.

Useful surface stabilizers which can be employed in the invention include, but are not limited to, known organic and inorganic pharmaceutical excipients. Such excipients include various polymers, low molecular weight oligomers, natural products, and surfactants. Exemplary surface stabilizers include non-ionic and ionic (e.g., anionic, cationic, and zwitterionic) surface stabilizers. Without wishing to be bound by any particular theory, it is believed that polymeric materials adhering to a particle surface can present a steric barrier preventing particle aggregation, while in the case of ionic surface stabilizers the stabilizing action may be attributed to electrostatic interactions.

Particularly preferred surface stabilizers for use with the present invention are polysorbate surfactants also referred to as polysorbates or polyoxyethylene sorbitan fatty acid esters. Examples include those available under the Tween® tradename (a registered trademark of Uniqema, a business unit of ICI Americas Inc.), such as Tween® 20 (polyoxyethylene 20 sorbitan monolaurate) also referred to as polysorbate 20 or PS20 herein, Tween® 40 (polyoxyethylene 20 sorbitan palmitate), also referred to as polysorbate 40 or PS40 herein or Tween® 80 (polyoxyethylene 20 sorbitan monooleate), also referred to as polysorbate 80 or PS80 herein. Polysorbates are amphiphilic, nonionic surfactants composed of a hydrophilic head group (sorbitan polyoxyethylene) linked by an ester bond to a hydrophobic tail group. The various grades differ in the length of this tail group, for example PS20 (laurate, C12), PS40 (palmitate, C16), PS80 (oleate, C18).

Other preferred surface stabilizers for use with the present invention include low molecular weight povidones, lecithin, DSPG (1,2-Distearoyl-sn-glycero-3-phospho-rac-(1-glycerol)), DOSS (dioctyl sodium sulfosuccinate, or docusate sodium), methyl and propyl parabens, sorbitan monolaurate, also referred to as SML, available under the trade name Span® 20, a registered trademark of Croda International PLC, carboxymethyl cellulose, hydroxypropylcellulose, also referred to as HPC and including examples such as HPC-SL a low viscosity grade which has a viscosity of 2.0 to 2.9 mPa·s in aqueous 2% w/v solution at 20° C. (available from Nippon Soda Co Ltd, Japan), sodium deoxycholate, akylsaccharides. Also preferred are block copolymers based on ethylene oxide and propylene oxide, also known as poloxamers and sold for example under the trade names Pluronic® and Lutrol®, registered trademarks of the BASF Corporation and Synperonic, a registered trademark of Croda international PLC. Examples include poloxamer 407 (Lutrol® F127), poloxamer 188 (Lutrol® F68/Pluronic® F68) or Poloxamer 338 (Lutrol® F108/Pluronic® F108). Poloxamers are amphiphilic, nonionic tri-block copolymers consisting of a central hydrophobic poly(propylene oxide) (PPO) block with terminal hydrophilic poly(ethylene oxide) (PEO) blocks. The various grades differ in the length of these blocks and proportion of the hydrophilic content. Poloxamer 188 is (18×100≈) 1800 g/mol and an (8×10≈) 80% of the total is polyoxyethylene; ($PEO_N$—$PPO_{27}$-$PEO_{80}$). Poloxamer 338 is (33×1000≈) 3300 g/mol and an (8×10≈) 80% of the total is polyoxyethylene; ($PEO_{132}$-$PPO_{50}$-$PEO_{132}$). It is also envisaged to use only the individual components which make up these block co-polymers, for example in the case of Pluronic F108, such individual components are Polyoxyethylene and polyoxypropylene glycol. It is particularly preferred to use the aforementioned individual components given their approval status. Other preferred stabilizers include TPGS (d-alpha tocopheryl polyethylene glycol 1000 succinate), gelatin and albumin, lysozyme and cyclodextrins (for e.g. betahydroxcyclodextrin). Also useful are gel forming polymers such as ReGel® (thermosetting biodegradable gel developed by British Technology Group)(ReGel is a registered trademark of protherics salt lake city, inc.). Particularly preferred surface stabilizers for use with the present invention are those which are approved by any regulatory authority for the preferred route of administration, intramuscular use.

Of the aforementioned, the following are particularly preferred as they would generally be considered to be more acceptable for intramuscular use: polysorbate surfactants such as Polysorbate 80, Polysorbate 40 and Polysorbate 20, low molecular weight povidones, lecithin, DSPG, and sorbitan monolaurate.

Other useful surface stabilizers include copolymers of vinylpyrrolidone and vinyl acetate or copovidone (e.g., Plasdone® S630, which is a random copolymer of vinyl acetate and vinyl pyrrolidone available from ISP Technologies, Inc (USA)); hydroxypropylmethylcellulose (HPMC, such as Pharmacoat® 603 available from Shin-Etsu Chemical Co Ltd, Japan); a polyvinylpyrrolidone (PVP), such as those available from ISP Corp (New Jersey, USA) under the Plasdone® trade name, e.g. Plasdone® C29/32 (which is equivalent to BASF PVP K29/32), Plasdone® C-30, Plasdone® C17 (equivalent to BASF PVP K-17) and Plasdone® C12 (equivalent to povidone K12); deoxycholic acid sodium salt, sodium lauryl sulphate (SLS also known as sodium dodecyl sulphate or SDS), benzalkonium chloride (also known as alkyldimethylbenzylammonium chloride), lecithin, distearyl palmitate glyceryl or a combination thereof. Other preferred surface stabilizers include albumin, lysozyme, gelatin, macrogol 15 hydroxystearate (available for example from BASF AG under the trade name Solutol® 15), tyloxapol and polyethoxylated castor oil (available for example from BASF AG under the trade name Cremophor® EL), PEG-40 Castor oil (Cremophor® RH 40, a registered trademark of the BASF group), (2-Hydroxypropyl)β-cyclodextrin, Polyethylene glycol tert-octylphenyl ether (Triton X-100™, a trademark of The Dow Chemical Company), Polyethylene glycol (15)-hydroxystearate (Solutol® HS 15, a registered trademark of the BASF group), sulfobutyl ether β-cyclodextrin.

The surface stabilizers are commercially available and/or can be prepared by techniques known in the art. Most of these surface stabilizers are known pharmaceutical excipients and are described in detail in the *Handbook of Pharmaceutical Excipients*, published jointly by the American Pharmaceutical Association and The Pharmaceutical Society of Great Britain (R. C. Rowe et al (ed.) $5^{th}$ Edition, The Pharmaceutical Press, 2006), specifically incorporated by reference.

Excipients

The composition of the present invention may further comprise one or more non-toxic physiologically acceptable carriers, adjuvants, or vehicles, collectively referred to as carriers. The composition can be formulated for administration via any pharmaceutically acceptable means, including but not limited to, parental injection (e.g. intramuscular, or subcutaneous). The small size of the aripiprazole prodrug particles (i.e. less than 1000 nm) makes the composition of the invention particularly advantageous for parenteral formulations.

The composition of the invention may include a chelating agent such as sodium citrate or sodium phosphate monobasic dihydrate ($NaH_2PO_4$ $2H_2O$) or Sodium phosphate dibasic anhydrous ($NaH_2PO_4$). Chelating agents bind with metal ion impurities introduced during the milling process thus preventing the formation of aldehydes.

The present composition may also include a buffer in order to raise the pH of the dispersion medium. Certain surface stabilizers, in particular Polysorbate 20 may be susceptible to oxidation. If after milling, the polysorbate 20 in composition oxidises, this may have the effect of lowering the overall pH of the dispersion medium. The drug thereafter may become more soluble in a medium of lower pH, possibly leading to growth in particle size due to processes such as Oswald ripening occurring. A buffer may therefore be included to counter any drop in pH and prevent this effect from occurring. Buffers which may be used with the composition of the present invention include sodium citrate or sodium phosphate monobasic dihydrate ($NaH_2PO_4$ $2H_2O$) or Sodium phosphate dibasic anhydrous ($NaH_2PO_4$).

The present composition may also include an antioxidant to prevent the oxidation of the surface stabilizer or any other constituent. Citric acid may be used an effective antioxidant.

The composition of the invention may also comprise a tonicity agent such as saline, sugars or polyols.

As described above, the composition of the present invention may be formulated as a dispersion, in which case the particles of the present invention are dispersed within a dispersion medium. The dispersion medium may be comprised of water and/or any of the excipients described above. Oils or other non-aqueous media may be used where compatible with the aripiprazole prodrug. Preferably, the dispersion medium is water or an aqueous based medium.

Alternatively, the composition of the present invention may be presented as particles in a dry form to be dispersed in a dispersion medium prior to administration. In such embodiments, the composition preferably comprises one or more of the above mentioned excipients and is reconstituted in water prior to administration.

Methods of Preparing the Aripiprazole Prodrug Composition of the Invention

The present invention further relates to a method of preparing an aripiprazole prodrug composition according to the present invention.

The method comprises the step of (a) calculating a quantity of at least one stabilizer to be added to the composition in order to ensure that both an adsorbed component and a free component of the stabilizer are present in the composition. This calculation may be done for example using methods for approximating the quantity of free surface stabilizer described herein. The method further includes (b) producing a population of aripiprazole prodrug particles having a volume based particle size (Dv50) of less than 1000 nm as determined by light scattering. This may be performed using any of the methods described below for producing small particles. The preferred method is milling. The method further includes (c) combining the quantity of surface stabilizer with the population of aripiprazole prodrug particles, such that the adsorbed component of the surface stabilizer is adsorbed on the surface of the aripiprazole prodrug particles. Adsorption of the surface stabilizer to the particles of aripiprazole prodrug may be attained by contacting the particles with the at least one surface stabilizer for a time and under conditions sufficient to provide a composition comprising particles of aripiprazole prodrug having a volume based particle size (Dv50) of less than 1000 nm. Step (b) and step (c) may be performed simultaneously by milling the aripiprazole prodrug with the stabilizer present, which is described in detail below and in the examples. The method may further comprise the step of (d) retaining a sample of the composition for testing the quantity of the free component of surface stabilizer, (e) separating the aripiprazole lauroxil particles and the surface stabilizer adsorbed thereto from the dispersion medium in the sample to form a supernatant, and (f) measuring the quantity of surface stabilizer in the supernatant using a high performance liquid chromatography (HPLC) apparatus in order to verify that the free component of stabilizer is indeed present in the composition.

The method may further comprise the step of (g) combining the aripiprazole prodrug particles and the surface stabilizer with a dispersion medium to form a dispersed aripiprazole prodrug composition. Further possible steps include (h) combining the aripiprazole prodrug particles with an additional population of aripiprazole prodrug particles having a volume based particle size (Dv50) at least about 100 nm greater in size and (i) filling the dispersed aripiprazole prodrug composition into an injection device (for example prefilled syringe, auto-injector, needleless syringe or dual chambered syringe. If a dual chambered syringe is used, the method can include the additional step of (g) filling the aripiprazole prodrug composition into one chamber of the dual chambered syringe, and filling the other chamber of the dual chamber syringe with a second composition. The second composition may be a second aripiprazole prodrug composition, having a different volume based particle size (Dv50) or could be an non-aripiprazole active ingredient, for example an atypical antipsychotic.

The composition of the present invention can be made using, for example, milling or attrition (including but not limited to wet milling), homogenization, precipitation, freezing, template emulsion techniques, supercritical fluid techniques, nano-electrospray techniques, or any combination thereof. Exemplary methods of making nanoparticulate compositions are described in the '684 patent. Methods of making nanoparticulate compositions are also described in U.S. Pat. No. 5,518,187 for "Method of Grinding Pharmaceutical Substances;" U.S. Pat. No. 5,718,388 for "Continuous Method of Grinding Pharmaceutical Substances;" U.S. Pat. No. 5,862,999 for "Method of Grinding Pharmaceutical Substances;" U.S. Pat. No. 5,665,331 for "Co-Microprecipitation of Nanoparticulate Pharmaceutical Agents with Crystal Growth Modifiers;" U.S. Pat. No. 5,662,883 for "Co-Microprecipitation of Nanoparticulate Pharmaceutical Agents with Crystal Growth Modifiers;" U.S. Pat. No. 5,560,932 for "Microprecipitation of Nanoparticulate Pharmaceutical Agents;" U.S. Pat. No. 5,543,133 for "Process of Preparing X-Ray Contrast Compositions Containing Nanoparticles;" U.S. Pat. No. 5,534,270 for "Method of Preparing Stable Drug Nanoparticles;" U.S. Pat. No. 5,510,118 for "Process of Preparing Therapeutic Compositions Containing Nanoparticles;" and U.S. Pat. No. 5,470,583 for "Method of Preparing Nanoparticle Compositions Containing Charged Phospholipids to Reduce Aggregation," all of which are specifically incorporated by reference.

Milling to Obtain an Aripiprazole Prodrug Composition

Milling aripiprazole prodrug to obtain an aripiprazole prodrug composition according to the present invention comprises dispersing the particles in a liquid dispersion medium in which the aripiprazole prodrug is poorly soluble, followed by applying mechanical means in the presence of grinding media to reduce the particle size of the aripiprazole prodrug to the desired volume based particle size (Dv50). The dispersion medium can be, for example, water, safflower oil, ethanol, t-butanol, glycerin, polyethylene glycol (PEG), hexane, or glycol. A preferred dispersion medium is water.

The aripiprazole prodrug particles can be reduced in size in the presence of at least one surface stabilizer. Alternatively, aripiprazole prodrug particles can be contacted with one or more surface stabilizers after attrition. Other compounds, such as a diluent, can be added to the aripiprazole prodrug/surface stabilizer composition during the size reduction process. Dispersions can be manufactured continuously or in a batch mode.

The grinding media can comprise particles that are preferably substantially spherical in shape, e.g., ceramic beads or beads consisting essentially of polymeric or copolymeric resin. Alternatively, the grinding media can comprise a core having a coating of a polymeric or copolymeric resin adhered thereon.

In general, suitable polymeric or copolymeric resins are chemically and physically inert, substantially free of metals, solvent, and monomers, and of sufficient hardness and friability to enable them to avoid being chipped or crushed during grinding. Suitable polymeric or copolymeric resins include crosslinked polystyrenes, such as polystyrene crosslinked with divinylbenzene; styrene copolymers; polycarbonates; polyacetals, such as Delrin™ (E.I. du Pont de Nemours and Co.); vinyl chloride polymers and copolymers; polyurethanes; polyamides; poly(tetrafluoroethylenes), e.g., Teflon® (E.I. du Pont de Nemours and Co.), and other fluoropolymers; high density polyethylenes; polypropylenes; cellulose ethers and esters such as cellulose acetate; polyhydroxymethacrylate; polyhydroxyethyl acrylate; and silicone-containing polymers such as polysiloxanes and the like. The polymer can be biodegradable. Exemplary biodegradable polymers or copolymers include poly(lactides), poly(glycolide) copolymers of lactides and glycolide, polyanhydrides, poly(hydroxyethyl methacrylate), poly(imino carbonates), poly(N-acylhydroxyproline)esters, poly(N-palmitoyl hydroxyproline) esters, ethylene-vinyl acetate copolymers, poly(orthoesters), poly(caprolactones), and poly(phosphazenes). For biodegradable polymers or copolymers, contamination from the media itself advantageously can metabolize in vivo into biologically acceptable products that can be eliminated from the body.

The grinding media preferably ranges in size from about 0.01 to about 3 mm. For fine grinding, the grinding media is preferably from about 0.02 to about 2 mm, and more preferably from about 0.03 to about 1 mm in size. The polymeric or copolymeric resin can have a density from about 0.8 to about 3.0 g/cm$^3$.

In a preferred grinding process the aripiprazole prodrug particles are made continuously. Such a method comprises continuously introducing an aripiprazole prodrug composition according to the invention into a milling chamber, contacting the aripiprazole prodrug composition according to the invention with grinding media while in the chamber to reduce the aripiprazole prodrug particle size of the composition according to the invention, and continuously removing the aripiprazole prodrug composition from the milling chamber. The grinding media is separated from the milled aripiprazole prodrug composition according to the invention using known separation techniques, in a secondary process such as by simple filtration, sieving through a mesh filter or screen, and the like. Other separation techniques such as centrifugation may also be employed.

An exemplary milling process using a Nanomill® 01 mill includes the following steps:
1. Calculation of the quantity of active pharmaceutical ingredient (API), surface stabilizer and other excipient needed for the composition.
2. Preparation of the continuous phase or dispersion medium, which includes the steps of weighing the excipients in a clean vial and vortexing the contents for a number of seconds, allowing the contents to sit for a short period of time thereafter. For preparation of the 10× vehicle, for example, sodium chloride may be dissolved in a citrate buffer. After filtration, the vehicle may be then transferred into a sterile container and stored in cold room.
3. Weighing the API and transferring the API into a milling chamber.
4. Adding the dispersion medium to the API in the chamber.
5. Mixing the content to ensure the surfaces are wetted.
6. Weighing milling media and adding the media to the milling chamber.
7. Mixing the contents of the chamber to ensure most of the media is wetted.
8. Installing the chamber onto the NanoMill and connecting the cooling bath.
9. Running the mill at its lowest setting for 5 minutes.
10. Milling the content at the desired tip speed and time.
11. Harvesting the milled composition. Where a Nanomill® 01 mill is used, it has been noted that compositions with mean particle size of less than 200 nm are best harvested by centrifuging using a 10 μm harvesting tube or a 10 mL stainless steel harvesting vessel with stainless steel screen having a mesh size ranging from 100 to 150 μm. For compositions having mean particle size of less than 250 nm, it is best to collect most of the NCD using a 23G needle first and then centrifuge the slurry left using the 10 μm harvesting tube and to combine the two portions thereafter.

An exemplary formulation using polysorbate 20 as a surface stabilizer may be prepared by milling crystals of aripiprazole lauroxil using a NanoMill at 30% (w/w) load in 2% (w/w) polysorbate 20. Dosing concentration may be achieved thereafter by diluting the resulting dispersion with vehicle. The potency can be accurately determined by HPLC.

Wet-milling can be conducted in aqueous vehicles containing stabilizing surface modifiers with polystyrene beads (Polymill® 500 milling media) using a NanoMill® 0.01 milling system. The milling shaft tip speed, the milling volume and the milling time may be adapted according to various experimental set-ups until the desired particle size is reached. "Stock" formulations can be harvested by pumping the dispersion through an appropriate filter (10 um polystyrene or 100 um metal mesh) at approximately 30% (w/w) API load. The solid load, surface stabilizer concentration, milling temperature, the milling shaft tip speed, the milling volume and the milling time may be adapted according to various experimental set-ups until the desired particle size is reached.

Precipitation to Obtain an Aripiprazole Prodrug Composition

Another method of forming an aripiprazole prodrug composition according to the present invention is by microprecipitation. This is a method of preparing stable dispersions of poorly soluble active agents in the presence of one or more surface stabilizers and one or more colloid stability enhancing surface active agents free of any trace toxic solvents or solubilized heavy metal impurities. Such a method comprises, for example: (1) dissolving aripiprazole prodrug in a suitable solvent; (2) adding the formulation from step (1) to a solution comprising at least one surface stabilizer; and (3) precipitating the formulation from step (2) using an appropriate non-solvent. The method can be followed by removal of any formed salt, if present, by dialysis or diafiltration and concentration of the dispersion by known means.

Homogenization to Obtain an Aripiprazole Prodrug Composition

Exemplary homogenization methods of preparing active agent compositions are described in U.S. Pat. No. 5,510,118, for "Process of Preparing Therapeutic Compositions Containing Nanoparticles." Such a method comprises dispersing aripiprazole prodrug particles in a liquid dispersion medium, followed by subjecting the dispersion to homogenization to reduce the particle size of aripiprazole prodrug to the desired volume based particle size (Dv50). The aripiprazole prodrug particles can be reduced in size in the presence of at least one surface stabilizer. Alternatively, the aripiprazole prodrug particles can be contacted with one or more surface stabilizers either before or after attrition. Other compounds, such as a diluent, can be added to the aripiprazole prodrug/surface stabilizer composition either before, during, or after the aripiprazole prodrug particle size reduction process. Dispersions can be manufactured continuously or in a batch mode.

Cryogenic Methodologies to Obtain an Aripiprazole Prodrug Composition

Another method of forming the aripiprazole prodrug composition of the present invention is by spray freezing into liquid (SFL). This technology comprises an organic or organo-aqueous solution of aripiprazole prodrug with surface stabilizers, which is injected into a cryogenic liquid, such as liquid nitrogen. The droplets of aripiprazole prodrug solution freeze at a rate sufficient to minimize crystallization and particle growth, thus formulating aripiprazole prodrug particles less than 1000 nm in size. Depending on the choice of solvent system and processing conditions, the aripiprazole prodrug particles can have varying particle morphology. In the isolation step, the nitrogen and solvent are removed under conditions that avoid agglomeration or ripening of the aripiprazole prodrug particles.

As a complementary technology to SFL, ultra rapid freezing (URF) may also be used to created equivalent aripiprazole prodrug particles with greatly enhanced surface area. URF comprises an organic or organo-aqueous solution of aripiprazole prodrug with surface stabilizers onto a cryogenic substrate.

Emulsion Methodologies to Obtain an Aripiprazole Prodrug Composition

Another method of forming the aripiprazole prodrug composition of the present invention is by template emulsion. Template emulsion creates nanostructured aripiprazole prodrug particles with controlled particle size distribution and rapid dissolution performance. The method comprises an oil-in-water emulsion that is prepared, then swelled with a non-aqueous solution comprising aripiprazole prodrug and surface stabilizers. The particle size distribution of aripiprazole prodrug is a direct result of the size of the emulsion droplets prior to loading with aripiprazole prodrug, a property which can be controlled and optimized in this process. Furthermore, through selected use of solvents and stabilizers, emulsion stability is achieved with no or suppressed Ostwald ripening. Subsequently, the solvent and water are removed, and the stabilized aripiprazole prodrug particles are recovered. Various aripiprazole prodrug particle morphologies can be achieved by appropriate control of processing conditions.

Supercritical Fluid Methods of Making an Aripiprazole Prodrug Composition

Aripiprazole prodrug compositions can also be made using methods employing the use of supercritical fluids. In such a method aripiprazole prodrug is dissolved in a solution or vehicle which can also contain at least one surface stabilizer. The solution and a supercritical fluid are then co-introduced into a particle formation vessel. If a surface stabilizer was not previously added to the vehicle, it can be added to the particle formation vessel. The temperature and pressure are controlled, such that dispersion and extraction of the vehicle occur substantially simultaneously by the action of the supercritical fluid. Chemicals described as being useful as supercritical fluids include carbon dioxide, nitrous oxide, sulphur hexafluoride, xenon, ethylene, chlorotrifluoromethane, ethane, and trifluoromethane.

Examples of known supercritical methods of making nanoparticles include International Patent Application No. WO 97/14407 to Pace et al, published on Apr. 24, 1997, which refers to particles of water insoluble biologically active compounds with an average size of 100 nm to 300 nm prepared by dissolving the compound in a solution and then spraying the solution into compressed gas, liquid, or supercritical fluid in the presence of appropriate surface stabilizers.

Similarly, U.S. Pat. No. 6,406,718 to Cooper et al. describes a method for forming a particulate fluticasone propionate product comprising the co-introduction of a supercritical fluid and a vehicle containing at least fluticasone propionate in solution or suspension into a particle formation vessel, the temperature and pressure in which are controlled, such that dispersion and extraction of the vehicle occur substantially simultaneously by the action of the supercritical fluid. Chemicals described as being useful as supercritical fluids include carbon dioxide, nitrous oxide, sulphur hexafluoride, xenon, ethylene, chlorotrifluoromethane, ethane, and trifluoromethane. The supercritical fluid may optionally contain one or more modifiers, such as methanol, ethanol, ethyl acetate, acetone, acetonitrile or any mixture thereof. A supercritical fluid modifier (or co-solvent) is a chemical which, when added to a supercritical fluid, changes the intrinsic properties of the supercritical fluid in or around the critical point. According to Cooper et al, the fluticasone propionate particles produced using supercritical fluids have a particle size range of 1 to 10 μm, preferably 1 to 5 μm.

Nano-Electrospray Techniques Used to Obtain an Aripiprazole Prodrug Composition

In electrospray ionization a liquid is pushed through a very small charged, usually metal, capillary. This liquid contains the desired substance, e.g., aripiprazole prodrug, dissolved in a large amount of solvent, which is usually much more volatile than the analyte. Volatile acids, bases or buffers are often added to this solution as well. The analyte exists as an ion in solution either in a protonated form or as an anion. As like charges repel, the liquid pushes itself out of the capillary and forms a mist or an aerosol of small droplets about 10 μm across. This jet of aerosol droplets is at least partially produced by a process involving the formation of a Taylor cone and a jet from the tip of this cone. A neutral carrier gas, such as nitrogen gas, is sometimes used to help nebulize the liquid and to help evaporate the neutral solvent in the small droplets. As the small droplets evaporate, suspended in the air, the charged analyte molecules are forced closer together. The drops become unstable as the similarly charged molecules come closer together and the droplets once again break up. This is referred to as Coulombic fission because it is the repulsive Coulombic forces between charged analyte molecules that drive it. This process repeats itself until the analyte is free of solvent and is a lone ion.

In nanotechnology the electrospray method may be employed to deposit single particles on surfaces, e.g., aripiprazole prodrug particles. This is accomplished by spraying colloids and ensuring that on average there is not more than one particle per droplet. Consequent drying of the surrounding solvent results in an aerosol stream of single aripiprazole prodrug particles. Here the ionizing property of the process is not crucial for the application but may be put to use in electrostatic precipitation of the particles.

Particle Size Characterization

The particle size of the present composition may be measured using techniques such as light scattering with either water or a dilute surface stabilizer solution as the diluent. Measurements may be verified using microscopy. Particle size distributions may be determined using a Horiba 950 particle size analyser as a wet suspension. The volume based particle size (Dv50) is expressed herein by the mean volume diameter of the particles. Particle size measurement can also be carried out using PCS (Dynamic light scattering measurements).

In addition to light scattering techniques, there are other methods for determining particle size as documented below.

Optical microscopy may be conducted on a Leica DMR microscope at 100× magnifications using Phase contrast optics. Image analysis may be performed using Axiovision software.

Scanning electron microscopy (SEM) may be conducted using a suitable scanning electron microscope such as a Phenom Pro G2. Samples may be prepared by casting diluted formulation at about 0.5 mg/mL on to 9 mm Pelcon carbon adhesive tabs, followed by air drying overnight. The samples may be sputter coated (2×) using a Denton Vacuum Desk V sputter coater.

Free Surface Stabilizer

In order to ensure that the appropriate amount of free surface stabilizer is present in the composition of the present invention, a rough approximation of the amount of surface stabilizer that must be added can be arrived at using the following theory. Note that the following abbreviations are used SA=Surface Area, NP=Nanoparticle, PS=Particle Size. The presence of free surface stabilizer may be approximately predicted according to the formula $SA_{stabilizer}/SA_{Available}$. If the resulting value is equal to 1 then the system is saturated with surface stabilizer. If the resulting value is less than 1, this would indicate that the system will not be saturated, and therefore there will not be any free surface stabilizer available. If the value is determined to be greater than 1 then the system is saturated, and free stabilizer will be available.

In the above equation $SA_{available}$ is the total surface area of drug substance available for a given mass. $SA_{stabilizer}$ is the surface area of the stabilizer head groups adsorbed to the surface of the drug particles. These values can be calculated by working out the total surface area based on the estimated radius of the drug particles. The radius (r) is calculated simply by taking the value for the volume based particle size (Dv50) and dividing by 2, when using the assumption that the drug particles are spherical. The resultant value is then multiplied by the number of particles (N), which is determined by the mass of drug used (M) divided by the mass of one drug particle. The mass of one particle may be calculated from the density of the drug substance ($\sigma$) multiplied by the volume of one particle ($V_{np}$), where $V_{np}=4\pi r^3/3$.

$$N=M/\sigma*V_{np}$$

Surface area of one nanoparticle=$SA_{NP}=4\pi r^2$

Surface area total=$SA_{total}=N*SA_{NP}$

Due to packing of the surface stabilizer head groups not all surface area is available. This may be modelled by assuming the nanoparticle is a sphere and assuming that Hexagonal Close Pack (HCP) packing will give a maximum for packing on the surface. The HCP for two dimensional circles (which this model assumes the stabilizer head groups to be) is 0.9069 (i.e. 90.69% of surface is covered).

$$SA_{available}=SA_{total}*0.9069$$

$SA_{stabilizer}$=Surface area of stabilizer head groups adsorbed to drug surface.

The value for $SA_{stabilizer}$ may be calculated as follows. First the mass of stabilizer to be included in the composition is converted to moles of stabilizer used. This is then used to calculate the number of stabilizer molecules present, which is the number of moles*NA (where NA is Avagadro's constant=$6.022*10^{-23}$ mol$^{-1}$). The number of stabilizer molecules is then multiplied by the surface area of the head group. The head group area for Polysorbate 20 is taken to be the surface area of the aliphatic C12 chain. Values for the head group area may be calculated from the literature and will depend on the orientation of this group at the surface (Tween surfactants: Adsorption, self-organization, and protein resistance: Lei Shen, Athena Guo, Xiaoyang Zhu; Surface Science 605 (2011) 494-499).

The aforementioned technique provides an approximate guideline of the quantity of surface stabilizer to be added.

Measurement of Free Surface Stabilizer

The quantity of free surface stabilizer may be determined after the compositions have been produced using techniques such as thermogravimetric analysis (TGA) or High-performance liquid chromatography (HPLC).

A method for determining a free component of surface stabilizer in an aripiprazole prodrug composition may comprise the following steps: (i) separating particles and the surface stabilizer adsorbed thereto from the dispersion medium to form a supernatant, and (ii) measuring the quantity of surface stabilizer in the supernatant using a high performance liquid chromatography (HPLC) apparatus.

HPLC could be used to determine the quantity of free surface stabilizer using for example reversed-phase HPLC analysis with a C8 column. This exemplified method is isocratic with 35% 10 mM Potassium phosphate buffer (pH 2.5) and 65% acetonitrile as the mobile phase and UV detection at 240 nm. The drug product is re-suspended and centrifuged/filtered to remove the drug substance and "bound" polysorbate 20. The amount of "free" polysorbate 20 is quantitated against polysorbate 20 standard solutions.

Method of Treatment and Use of the Aripiprazole Prodrug Composition of the Invention The invention also provides a method of treating a mammal in need comprising administering a stable aripiprazole prodrug composition comprising: (a) particles of aripiprazole prodrug or a salt thereof having a volume based particle size (Dv50) of less than about 1000 nm; and (b) at least one surface stabilizer.

The aripiprazole prodrug composition of the invention may be useful in the treatment of diseases and disorders of the CNS, such as mental diseases and disorders, including but not limited to schizophrenia, acute manic and mixed episodes associated with bipolar disorder, and other schizophreniform illnesses, major depressive disorder (MDD), and treatment of irritability associated with autistic disorder. The method may include treating a mammal, including a human, for disorders of the central nervous system, such as mental diseases or disorders; such treatments may include psychiatric treatment. The treatment may involve administering to the mammal a composition comprising an aripiprazole prodrug according to the present invention.

The composition of the invention can be administered to a subject via any pharmaceutically acceptable means including, but not limited to parenterally (e.g., intramuscular, or subcutaneous).

A composition suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents, or vehicles including water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants.

The composition may be administered in any pharmaceutically acceptable form; however, an injectable formulation is preferred.

For example, the injectable formulation may be administered as an intramuscular or subcutaneous injection so as to form a bolus or depot; the depot may allow for a prolonged duration of action, for example, by dissolving slowly and steadily into the subject's system. Thus, the injectable formulations may be configured to allow for the controlled release of the aripiprazole prodrug after subcutaneous, intramuscular, intraperitoneal, etc. injection. For example, particle size and excipient concentration may be adjusted to result in the controlled release (e.g., the blood levels of aripiprazole prodrug in the subject's remain within an effective therapeutic window) greater than about 24 hours, greater than about 3 days, for greater than about 5 days, for greater than about 7 days, for greater than about 10 days, for greater than about 14 days, for greater than about 20 days, for greater than about 30 days, for greater than about 2 months, for greater than about 3 months or for greater than about 4 months, or for any time period in between these values. The composition may be formulated such that the injected depot may release aripiprazole prodrug at therapeutic levels for periods of from about two to about twenty-four weeks; from about two to about six weeks; from about two to about four weeks; or from about one to about four weeks.

In the treatment of central nervous system disorders, it is useful to provide a drug dosage form that delivers the required therapeutic amount of the drug in vivo and renders the drug bioavailable in a rapid and consistent manner. These goals may be achieved using the injectable formulations of the aripiprazole prodrug composition described herein, via the formation of a depot (e.g., with intramuscular injection) as described above. In some embodiments, the drug is released from the depot into the blood stream at a constant rate, thus providing the patient with the proper dose of the drug continuously for an extended period of time. This method (e.g., depot injection) also results in improved patient compliance. A single injection once per month, for example, will provide the patient with the appropriate therapeutic dosage for the month, versus the daily struggle to remember or to decide to take a tablet, capsule, etc.

An exemplary injectable formulation of aripiprazole prodrug for intramuscular or subcutaneous administration may include aripiprazole prodrug particles having a volume based particle size (Dv50) of less than 1000 nm and having one or more surface stabilizers, such as but not limited to a polyoxyethylene sorbitan fatty acid ester (polysorbate 80, polysorbate 40, polysorbate 20), low molecular weight povidones, lecithin, d-alpha tocopheryl polyethylene glycol 1000 succinate, dioctyl sodium sulfosuccinate, or docusate sodium), methyl and propyl parabens, sorbitan monolaurate, carboxymethyl cellulose, hydroxypropylcellulose, sodium deoxycholate, akylsaccharides, difunctional block copolymers, d-alpha tocopheryl polyethylene glycol 1000 succinate, gelatin, albumin, lysozyme, cyclodextrins (for example betahydroxcyclodextrin) and gel forming polymers, adsorbed on the surface thereof in an amount sufficient to maintain a volume based particle size (Dv50) for the desired duration of efficacy. Such an aripiprazole prodrug composition formulated for parenteral administration may enhance the efficacy of aripiprazole prodrug in the treatment of various types of CNS diseases or disorders, such as mental diseases and disorders.

A composition suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents, or vehicles including water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants.

The aripiprazole prodrug composition may also comprise adjuvants such as preserving, wetting, emulsifying, and dispensing agents. Prevention of the growth of microorganisms can be ensured by various antibacterial and antifungal agents, such as parabens, chlorobutanol, phenol, sorbic acid, and the like. It may also be desirable to include isotonic agents, such as sugars, sodium chloride, and the like. Prolonged absorption of the injectable pharmaceutical form can be brought about by the use of agents delaying absorption, such as aluminum monostearate and gelatin.

In addition, it is anticipated that a higher concentration of the form of aripiprazole prodrug may be delivered in a smaller injectable dose size (and thus smaller volume) as compared to conventional forms of aripiprazole prodrug. This ensures that any discomfort to the patient when administering is kept to a minimum.

The composition may also comprise adjuvants such as preserving, wetting, emulsifying, and dispensing agents. Prevention of the growth of microorganisms can be ensured by various antibacterial and antifungal agents, such as parabens, chlorobutanol, phenol, sorbic acid, and the like. It may also be desirable to include isotonic agents, such as sugars, sodium chloride, and the like. Prolonged absorption of the injectable pharmaceutical form can be brought about by the use of agents delaying absorption, such as aluminum monostearate and gelatin.

All publicly available documents referenced herein, including but not limited to US patents, are specifically incorporated by reference.

EXAMPLES

The following examples are provided to illustrate the present invention. It should be understood, however, that the invention is not to be limited to the specific conditions or details described in these examples.

All units specified in terms of percentages (%) refer herein to percentage weight by weight (% w/w), i.e. the weight of the constituent is expressed as a percentage of the overall weight of the sample prepared.

Horiba: refers to a Horiba LA 910 of LA 950 particle size analyser (Horiba Instruments, Irvine, Calif., USA).

For all of the below examples, milling was performed on a NanoMill® 0.01 (Alkermes Pharma Ireland Limited) which has a chamber size of 10 ml, 50 ml, or 100 ml along with a 500 µm or 250 µm Polymill® grinding media, which was supplied by Dow chemical Co., Michigan, United States (PolyMill® is a registered trademark of Alkermes Pharma Ireland Limited).

Unless otherwise indicated, materials were sourced as follows: Polysorbate 20, Sodium Citrate and Sodium chloride were supplied by Avantor™ Performance Materials supplied under its J. T. Baker® brand. Avantor Performance Materials, Inc, Philadelphia, USA. Phosphate buffered saline was supplied by either EMD Millipore in the case of sodium phosphate monobasic dihydrate ($NaH_2PO_4 \cdot 2H_2O$) or Avantor™ Performance Materials, J. T. Baker® brand in the case of Sodium phosphate dibasic anhydrous ($NaH_2PO_4$). Arginine-HCL was supplied by Sigma-Aldrich Co. LLC, St. Louis, Mo., USA. Aripirazole lauroxil and aripiprazole cavoxil may be produced as described in U.S. Pat. No. 8,431,576. Each of the formulations described below were produced from a solid particulate form, in the case of aripirazole cavoxil the particle size (Dv50) prior to milling was greater than 8 microns and in the case of aripiprazole lauroxil the particle size (Dv50) prior to milling was greater than 10 microns.

In some cases, abbreviations are used for some components of the composition. For instance, PS20 signifies polysorbate 20, PBS signifies phosphate buffered saline, CBS signifies citrate buffered saline. All printed publications referenced herein, including but not limited to patents, are specifically incorporated by reference.

Example 1: Rodent Study

The purpose of this study was to compare the pharmacokinetic properties of a dispersion of aripiprazole cavoxil having an volume based particle size (Dv50) of less than 200 nm with a larger particle size dispersion of aripiprazole cavoxil.

Three samples were prepared as follows.

Formulation 1 was prepared according to the following steps. 4.66 g of a crude slurry of 13.6% (w/w) aripiprazole cavoxil and 1.6% (w/w) polysorbate 20 was first prepared. The mixture was then diluted by adding 10 mM buffer solution prepared from 0.8% (w/w) polysorbate 20 and the remainder phosphate buffered saline. The slurry was then transferred to a NanoMill 0.01 having a 10 ml chamber and straight shaft. The slurry was first mixed by hand with a spatula. The composition was milled for 60 minutes at a milling speed of 2500 rpm (revolutions per minute). The milling temperature during this process was 15° C. The resulting mixture was collected using Vectaspin tubes, over a period of 10 minutes at a temperature of 10° C. and a milling speed of 2500 rpm. The final composition as determined by potency assay comprised 8.39% (w/w) aripiprazole cavoxil, 1.6% (w/w) polysorbate 20, 10 mM phosphate buffer and 0.8% (w/w) sodium chloride. The drug to surface stabilizer ratio was approximately 5:1. Particle size analysis was performed on a Horiba LA950 using water as the observation medium (DDH20 at 79% T; RI=1.57-0.01i) and the composition was found to have a mean particle size of 127 nm, with a Dv90 of 194 nm, a Dv50 of 120 nm and a Dv10 of 73 nm.

Formulation 2 (comparator) was prepared as a comparator composition having a particle size larger than the composition of the present invention. A crude slurry of 13.6% (w/w) aripiprazole cavoxil crystals and 1.6% (w/w) Polysorbate 20 was first prepared and mixed for 1 hour. This was then diluted with a buffer solution comprising 1.6% (w/w) polysorbate 20 and phosphate buffered saline to the desired potency. The final composition comprised approximately 8.8% (w/w) of aripiprazole cavoxil, 1.6% (w/w) polysorbate 20, 10 mM phosphate buffered saline, and 0.8% (w/w) sodium chloride. The final composition was determined to have a pH of 6.9 with an osmolality of 279. Particle size analysis was conducted on a Horiba LA910, observation medium was water with 0.1% (w/w) polysorbate 20. The composition was subjected to sonication over a period of 1 minute prior to the analysis. The composition was determined to have a mean particle size of 28,000 nm (28 µm), with a Dv90 of 52, 800 nm (52.8 µm) and a Dv10 of 3,774 nm (3.8 µm).

Formulation 3 (comparator) was an additional composition outside the scope of the present invention. This formulation comprised 8.3% (w/w) aripiprazole cavoxil, 2% (w/w) carboxy methyl cellulose, 0.2% (w/w) Polysorbate 20, 10 mM Phosphate buffer, and 0.6% (w/w) sodium chloride. The composition was sonicated for 1 minute prior to particle size analysis on a Horiba LA 910 using a mixture of water and 0.1% (w/w) polysorbate 20 as the sizing medium. The composition was determined to have a mean particle size of 26,200 nm (26.2 µm), a Dv10 of 3,616 nm (3.6 µm) and a Dv90 of 51,260 nm (51.3 µm).

All three formulations were stored at room temperature prior to dosing. Six rat subjects were used. The compositions were dosed intramuscularly, at a dose strength of approximately 20 mg, active concentration of 65 mg/mL and a dose volume of 0.3 mL.

The pharmacokinetic properties measured as aripiprazole concentration in plasma are shown below in Table 1.

TABLE 1

Mean aripiprazole concentrations

Mean aripiprazole concentrations (ng/ml) in rat plasma

| Timepoint (hr) | Formulation 1 | Formulation 2 (comparator) | Formulation 3 (comparator) |
| --- | --- | --- | --- |
| 0.6 | 34.4 | 2.13 | 2.42 |
| 1 | 135 | 6.31 | 5.23 |
| 6 | 513 | 44.8 | 31.8 |
| 24 | 489 | 54.4 | 23.0 |
| 48 | 167 | 59.2 | 19.0 |
| 72 | 90.6 | 64.7 | 17.5 |
| 96 | 64.9 | 70.7 | 19.6 |
| 168 | 48.9 | 98.7 | 60.9 |
| 192 | 38.6 | 94.2 | 68.2 |
| 216 | 23.6 | 88.4 | 69.2 |
| 240 | 16.9 | 74.6 | 61.0 |

Figure 2:
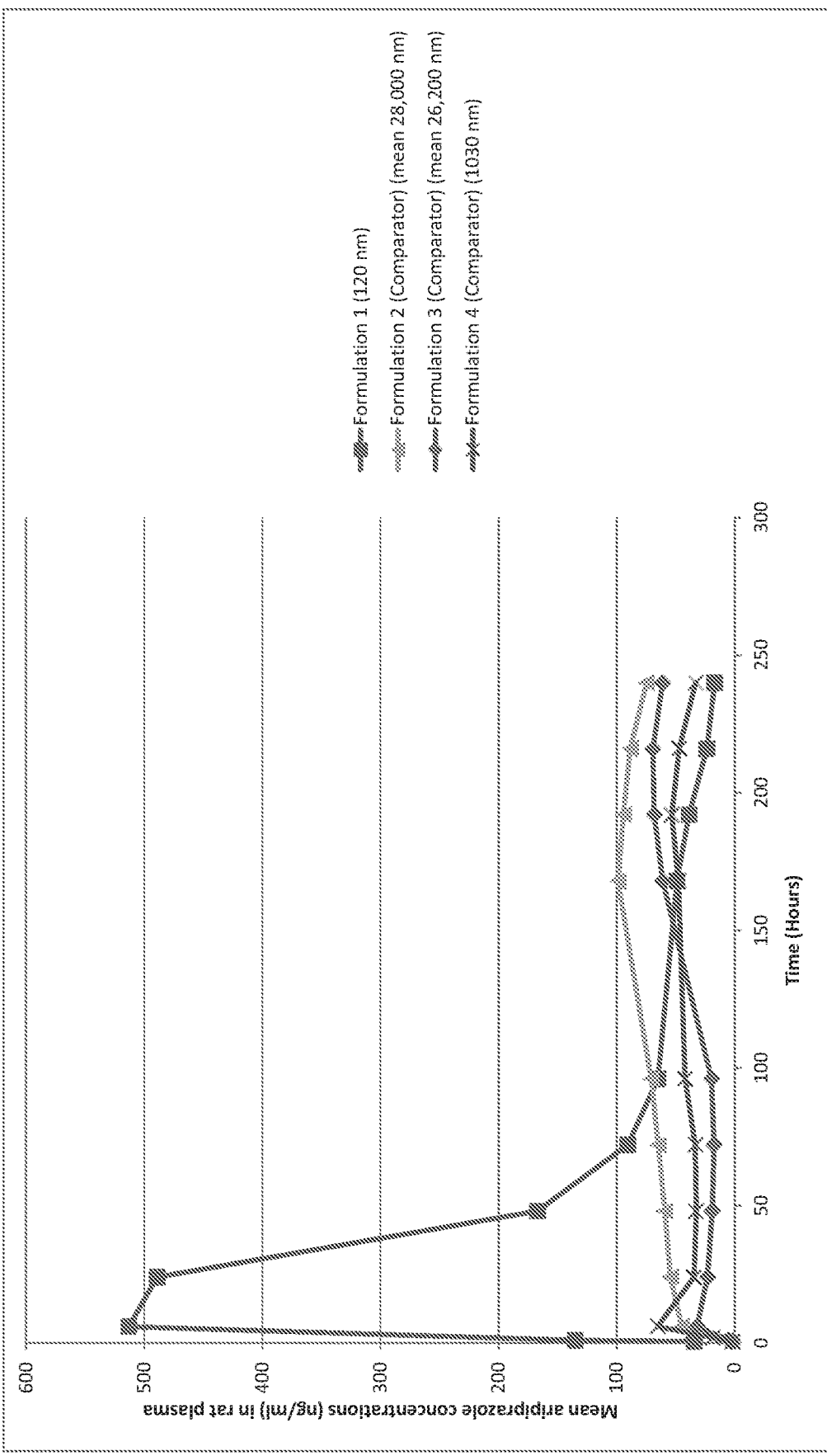
FIG. 2 is a plot of the mean plasma and blood concentrations for Formulations 1, 2 (comparator), 3 (comparator) and 4 as measured in vivo in rodent subjects over the various time points and as discussed in Examples 1 and 2.

The mean aripiprazole concentration curves for Formulations 1, 2 (comparator) and 3 (comparator) are shown in FIG. 2. The study demonstrated that a formulation of aripiprazole cavoxil according to the invention (Formulation 1) results in a significant change in the $T_{max}$ observed in vivo. In this instance the $T_{max}$ was shortened from 168 hours in the case of a larger particle size comparator composition to 6 hours in the case of a composition having a particle size of less than 1000 nm as per the present invention, (i.e. a 28 fold decrease in $T_{max}$, or a decrease of 96%).

Example 2: Rodent Study (Comparative Example)

A further rodent study was conducted as a comparative example in order to determine the pharmacokinetic properties of a dispersion of aripiprazole cavoxil having a particle size of just over 1000 nm.

Formulation 4 (comparator) was prepared as follows. A crude slurry of 30% (w/w) aripiprazole cavoxil, 1.6% (w/w) polysorbate 20 and water was prepared. This was then mixed for 5-10 minutes, before being transferred to a NanoMill 0.01, having 10 ml chamber and straight shaft. 500 μm PolyMill milling media was then added to make up a 69% (w/w) media load (4.21 g media). This was milled at 1500 rpm's for between 45 and 60 minutes at 15° C. The concentration of this composition after harvesting was 29% (w/w) aripiprazole cavoxil in 1.6% (w/w) polysorbate 20. This was then diluted to the desired potency in a buffer solution comprising 1.6% (w/w) polysorbate 20 and 10 mM phosphate buffered saline. The final composition comprised 7.9% (w/w) aripiprazole cavoxil, 1.6% (w/w) polysorbate 20 in phosphate buffered saline, and had a pH of 7.03 and an osmolality of 253. Particle size analysis was performed on a Horiba 950 using water as the diluent (RI=1.57-0.01i); where it was determined that the mean particle size was 1080 nm, the Dv90 was 1,740 nm, and the Dv50 was 1,030 nm. The free component of surface stabilizer was determined to be 21 ug/ml.

The study was performed using four rat subject subjects. The compositions were dosed intramuscularly, at a dose strength of 20 mg and a dose volume of 0.3 mL.

The mean aripiprazole concentration values as measured in whole blood are shown in Table 2 below. These values are plotted in the concentration curve depicted in FIG. 2, such that they are compared against the respective concentration curves obtained for Formulations 1-3 of Example 1.

TABLE 2

Mean aripiprazole concentrations

| Timepoint (hr) | Mean aripiprazole concentrations (ng/ml) in whole blood Formulation 4 (comparator) |
|---|---|
| 0.5 | 2.14 |
| 2 | 18.3 |
| 6 | 65.2 |
| 24 | 34.4 |
| 48 | 32.4 |
| 72 | 33.4 |
| 96 | 41.9 |
| 168 | 47.7 |
| 192 | 53.3 |
| 216 | 47.0 |
| 240 | 33.0 |

The data generated from this study demonstrates that a formulation of aripiprazole cavoxil having a particle size of just over 1 um exhibits pharmacokinetic properties which are very similar to those observed in vivo in the case of Formulation 2 (comparator) and Formulation 3 (comparator), both of which have particle sizes which are orders of magnitude greater the particle size of the present invention.

Example 3: Rodent Study

The purpose of the study was to compare the pharmacokinetic characteristics of aripiprazole cavoxil compositions having a particle size of between 200 nm and 1000 nm.

Formulations 5 and 6 were prepared in accordance with the formulation details set out below.

For Formulation 5, a crude slurry (total 5.86 g) was prepared comprising 15% (w/w) aripiprazole cavoxil, 1.6% (w/w) polysorbate 20 and water. 500 μm PolyMill milling media was added, the total amount being 4.21 g (i.e. 69% media load). This was transferred to a NanoMill 0.01 having a 10 ml chamber and straight shaft and mixed by hand for 5 to 10 minutes using a spatula. The composition was milled at 2500 rpm for 55 minutes at 15° C. The milled composition was then collected using Vectaspin tubes. The concentration after harvesting was 13.7% (w/w) aripiprazole cavoxil, 1.6% (w/w) polysorbate and the remainder water. This was then diluted to the desired potency with a buffer solution of 1.6% (w/w) polysorbate 20 and 10 mM phosphate buffered saline. The final composition comprised 8.4% (w/w) aripiprazole cavoxil, 1.6% (w/w) polysorbate 20 and phosphate buffered saline; and had a pH of 6.9 and an osmolality of 287 mOsm/kg. Particle size analysis was conducted on a Horiba 950 using water as the diluent (RI=1.57-0.01i); and the composition was determined to have a mean particle size of 245 nm, with a Dv90 of 459 nm, a Dv50 of 200 nm, and a Dv10 of 91 nm.

For Formulation 6, a crude slurry (total 5.86 g) comprising 15% (w/w) aripiprazole cavoxil and 1.6% (w/w) polysorbate 20 in water was prepared. 500 μm PolyMill milling media was added (i.e. 69% media load or 4.21 g. The slurry was added to a NanoMill 0.01 having a 10 ml chamber and straight shaft, and mixed for 5 to 10 minutes using a spatula. The composition was then milled at 1500 rpm for 45 minutes and collected using a syringe. The concentration of the respective components after harvesting was determined to be 12.9% (w/w) aripiprazole cavoxil, 1.6% (w/w) polysorbate 20 and water. This was diluted to the desired potency with a buffer solution, again 1.6% (w/w) polysorbate 20 and 10 mM phosphate buffered saline. The final composition was 8.1% (w/w) aripiprazole cavoxil and 1.65% (w/w) polysorbate 20 in phosphate buffered saline. The measured pH was 7.0 with an osmolality of 281 mOsm/kg. Particle size analysis on a Horiba 950 with water as the sizing medium (R1-1.57-0.01i) determined that the mean particle size of the composition was 475 nm, with a Dv90 of 942 nm, a Dv50 of 363 nm and a Dv10 of 143 nm.

Figure 3:
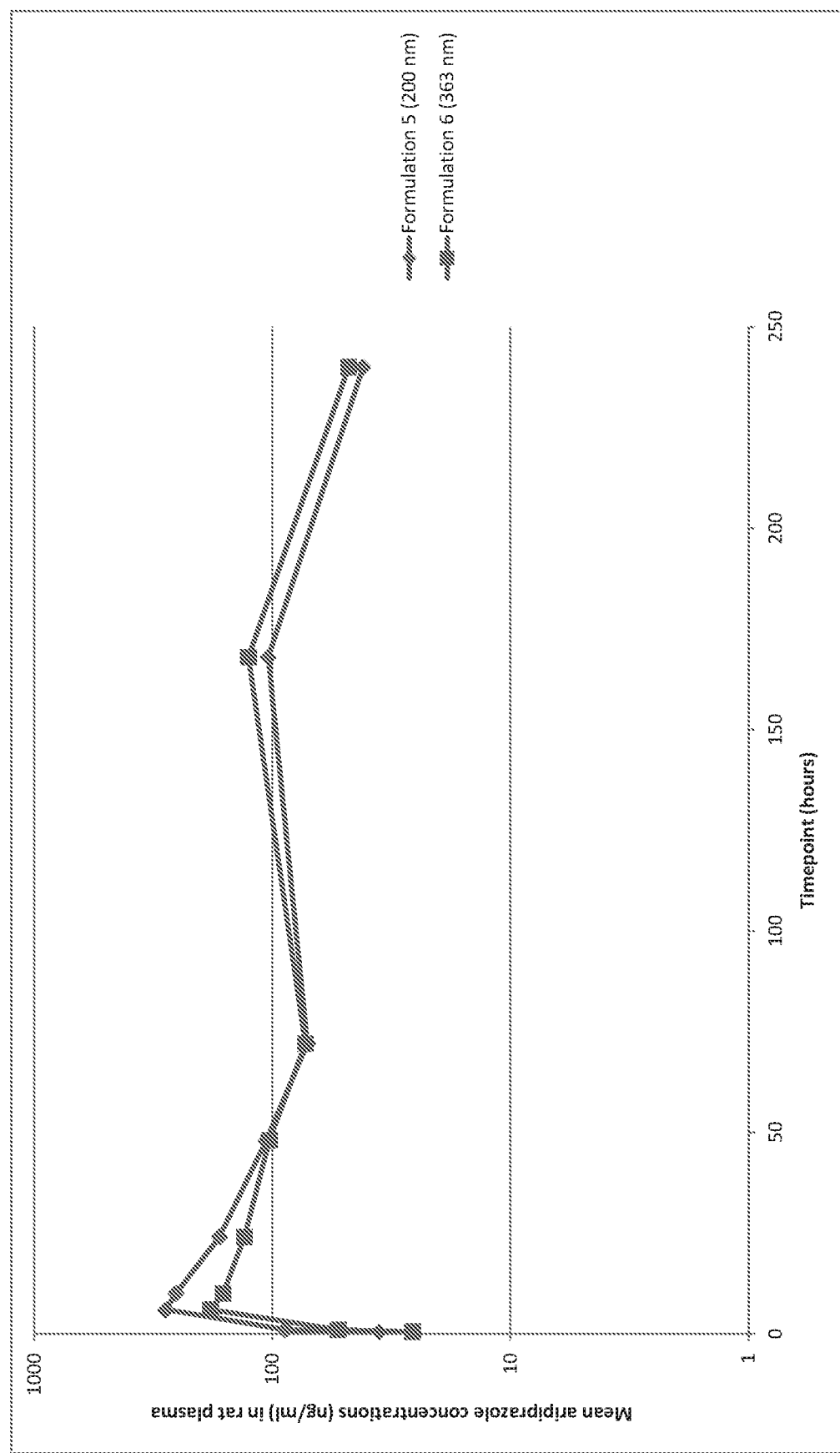
FIG. 3 is a plot of the mean blood concentrations as measured in vivo in rodent subjects for Formulations 5 and 6 as discussed in Example 3.

The study was performed using 4 rat subjects. The compositions were dosed intramuscularly, at a dose strength of 20 mg and a dose volume of 0.3 mL. The mean aripiprazole concentrations as measured in vivo in plasma at various time points are set out in Table 3 and plotted in the aripiprazole concentration curves shown in FIG. 3.

TABLE 3

Mean aripiprazole concentrations

| | Mean aripiprazole concentrations (ng/ml) in plasma | |
|---|---|---|
| Timepoint (hr) | Formulation 5 | Formulation 6 |
| 0.5 | 35.5 | 25.8 |
| 1 | 88.2 | 53 |
| 6 | 280 | 182 |
| 10 | 254 | 161 |
| 24 | 167 | 131 |
| 48 | 106 | 103 |
| 72 | 71.3 | 72.6 |
| 168 | 104 | 126 |
| 240 | 41.6 | 47.8 |

The results of this study suggest that a smaller particle size showed a higher exposure of aripiprazole.

Example 4: Rodent Study

This study focussed on aripiprazole lauroxil in an in-vivo model. The objective of this study was to examine whether changes in pharmacokinetic properties (e.g. reduction in onset time or $T_{max}$) could be achieved by reducing the particle size to the sub-1000 μm range were achievable in the case of aripiprazole lauroxil. The study compared the pharmacokinetic properties of formulations of aripiprazole lauroxil having a particle size range according to the present invention with formulations of aripiprazole lauroxil whose size range lies outside the scope of the present invention.

Formulation 7 comprised aripiprazole lauroxil and was prepared as follows. 5.86 g of a crude slurry of 30% (w/w) aripiprazole lauroxil, 2% (w/w) polysorbate 20 and water was first prepared. This was mixed for 5-10 minutes prior to being milled in a NanoMill 0.01 having a 10 ml bucket and straight shaft. The milling media used was 500 μm PolyMill (4.21 g added, 69% (w/w) media load). The composition was milled at 2500 rpm for a period of 35 minutes at 15° C. After harvesting, the milled composition was diluted to the desired potency with water and 10 mM citrate buffered saline. The final composition comprised 9.2% (w/w) aripiprazole lauroxil, 0.67% (w/w) polysorbate 20 in 10 mM Citrate buffered saline. [0207] The pH was determined to be 6.6 and the osmolality was 281 mOsm/kg. Particle size analysis was carried out on a Horiba 950 using water as the diluent (RI: 1.62-0.01i) and the mean particle size was determined to be 174 nm, with a Dv90 of 286 nm, a Dv50 of 157 nm and a Dv10 of 82 nm.

Formulations 8 and 9 were prepared from the same milled slurry, and differed only in the sense that Formulation 9 was prepared without any buffer, tonicity agents or hypotonic agents. The crude slurry for both Formulation 8 and 9 comprised 30% (w/w) aripiprazole lauroxil, 2% (w/w) polysorbate 20 and water. The crude slurry was calculated at 5.86 g in total. This was mixed for 5-10 minutes prior to being milled in a NanoMill 0.01 having a 10 ml bucket and straight shaft. The milling media used was 500 μm PolyMill (4.21 g added, 69% (w/w) media load). The composition was milled at 2500 rpm for a period of 30 minutes at 15° C. After harvesting. In the case of Formulation 8, the milled composition was diluted to the desired potency with 10 mM citrate buffered saline. The final composition comprised 9.56% (w/w) aripiprazole lauroxil, and 0.67% (w/w) polysorbate 20 in 10 mM Citrate buffered saline. The pH was determined to be 6.3 and the osmolality was 229 mOsm/kg.

Particle size analysis was conducted on a Horiba 950 using water as the diluent (RI: 1.62-0.01i) and the mean particle size was determined to be 687 nm with a Dv50 of 649 nm, a Dv90 of 1134 nm and a Dv10 of 284 nm. In the case of Formulation 9, the dilution used just water. The final composition comprised 9.41% (w/w) aripiprazole lauroxil, 0.67% (w/w) polysorbate 20 in water and had a pH of 6.4. The particle size distribution was very similar to Formulation 8 above (the mean was 584 nm, the Dv50 was 549 nm, the Dv90 was 961 and the Dv10 was 261)

Formulation 10 was an un-milled comparator comprising 10% (w/w) aripiprazole lauroxil+2% (w/w) polysorbate 20 (LSC12-226) in Citrate Buffered Saline. The composition was prepared and stirred overnight before dosing. Final pH was 6.2 with an osmolality of 264 mOsm/kg. The mean particle size was measured at 17,000 nm, with a Dv90 of 28,300 nm, a Dv50 of 14,200 nm, and a Dv10 of 7,500 nm.

The formulations were dosed in rats and dosing details are provided in Table 4 below. The column labelled ARI dose depicts the aripirazole equivalent dose value in miligrams.

TABLE 4

(Summary of dosing details for rodent study)

| Formulation | API level | PS20 (%) | Ratio | Milling | Mean (nm) | Dose Level (mg/ml) | ARI Dose (mg) | pH | Osmolality (mOsm/kg) | Vehicle |
|---|---|---|---|---|---|---|---|---|---|---|
| 7 | 30 | 2 | 15:1 | 135 min @ 2500 rpm | 200 | 63 | 100 | 6.6 | 281 | 10 mM citrate, 0.8% salt |
| 8 | 30 | 2 | 15:1 | 30 min @ 2500 rpm | 540 | 65 | 100 | 6.3 | 229 | 10 mM citrate, 0.8% salt |
| 9 | 30 | 2 | 15:1 | 30 min @ 2500 rpm | 540 | 64 | 100 | 6.4 | 12 | Water for injection |
| 10 | 10 | 2 | 5:1 | Stirred at 300 rpm overnight | 22000 | 63 | 100 | 6.2 | 264 | 10 mM citrate, 0.8% salt |

Figure 4:
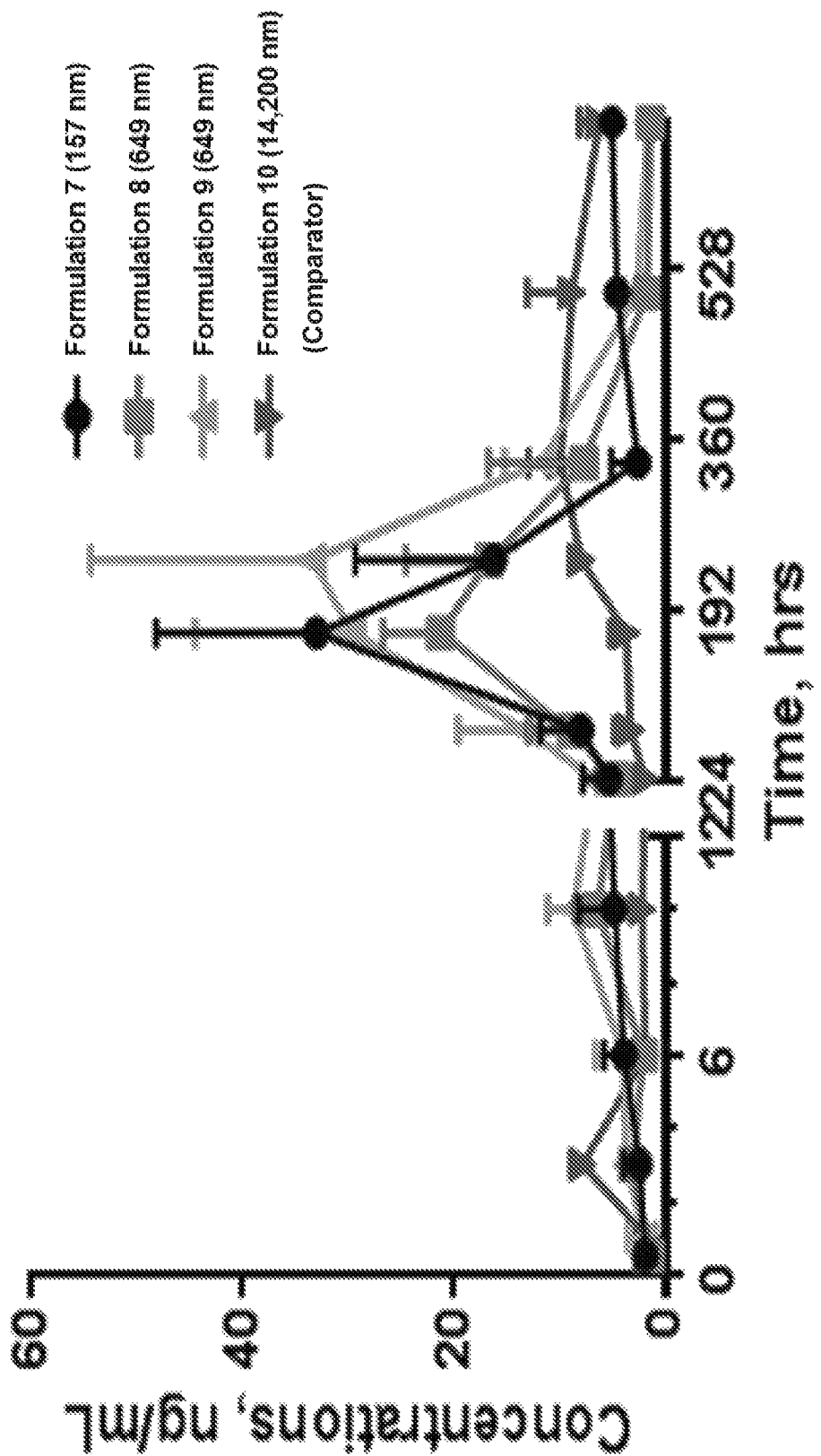
FIG. 4 is a plot of the mean aripiprazole concentrations as measured in vivo in rodent subjects for Formulations 7, 8, 9 and 10 (comparator) discussed in Example 4.

The mean aripiprazole values as measured in vivo over the various time points are depicted in Table 5 below. These values are also plotted in FIG. 4.

TABLE 5

Mean aripiprazole concentrations

| | Mean aripiprazole concentrations (ng/ml) in whole blood | | |
|---|---|---|---|
| Timepoint (hr) | Formulation 7 | Formulation 8 | Formulation 9 |
| 0.5 | 35.5 | 25.8 | 16.4 |
| 1 | 88.2 | 53 | 42.8 |
| 6 | 280 | 182 | 114 |
| 10 | 254 | 161 | 100 |
| 24 | 167 | 131 | 75.6 |
| 48 | 106 | 103 | 61.3 |
| 72 | 71.3 | 72.6 | 45.6 |
| 96 | | | |
| 168 | 104 | 126 | 51.4 |
| 192 | | | |
| 216 | | | |
| 240 | 41.6 | 47.8 | 18.3 |

The results indicate that reducing the particle size of aripiprazole lauroxil to less than 1000 nm provides a faster onset and reduced $T_{max}$ in comparison to a larger particle size comparator formulation having a Dv50 of 14,200 nm (Formulation 10). Such properties are useful in the context of a lead-in formulation. This study provided a basis for further studies with aripiprazole lauroxil examining the effect of particle size in the sub-1000 nm range.

Example 5: Dog Study

The purpose of this study was to examine the respective pharmacokinetic profiles obtained for aripiprazole lauroxil composition having a particle size of about 350 nm, about 450 nm and a mixed population of particles when dosed in vivo in dogs.

Formulation 11: A crude slurry (total 73 g) was prepared which comprised 30% (w/w) aripiprazole lauroxil, 2% (w/w) polysorbate 20 and water. The mixture was milled on a NanoMill® 0.01 mill having a 50 ml bucket and pegged shaft, at 300 rpm for 5 minutes and at 1300 rpm for 330 minutes. 500 μm PolyMill milling media was used, and the total media load was 69% (w/w). The resulting mixture was hand collected in a laminar flow hood using a 5 ml syringe and a 23 gauge needle, potency tested and then diluted. The final composition was comprised of 14.3% (w/w) aripiprazole lauroxil and 1% (w/w) polysorbate 20 in 10 mM citrate buffered saline and had a pH of 6.3 and an osmolality of 320 mOsm/kg. Particle size analysis conducted on a Horiba 950 (sizing medium was water) and it was determined that the mean particle size was 395 nm; the Dv90 was 623 nm; the Dv50 was 368 nm; and the Dv10 was 205 nm.

Formulation 12: A crude slurry (total 73 g) was prepared which comprised aripiprazole lauroxil 30% (w/w), 2% (w/w) polysorbate 20 as the surface stabilizer and water. 1.6% (w/w) arginine HCl was added as a buffer. The composition was milled on a NanoMill® 0.01 mill having a 50 ml bucket and pegged shaft, and using 500 μm PolyMill media at a media loading of 69% (w/w). The milling temperature was maintained at 15° C. The composition was milled at 300 rpm for 5 minutes and subsequently milled at 1300 rpm for 335 minutes. The milled composition was then hand collected in a laminar flow hood using a 5 ml syringe and a 23 gauge needle, potency tested and then diluted. The composition was then diluted to the desired potency with Arginine-HCL solution. The final composition comprised 14.9% (w/w) aripiprazole lauroxil, 1% (w/w) polysorbate 20 and 1.6% (w/w) Arginine hydrochloride. Particle size analysis was conducted on a Horiba 950 using water as the sizing medium, where it was determined that the mean particle size was 465 nm; the Dv90 was 794 nm, the Dv50 was 447 nm, and the Dv10 was 231 nm. The pH as measured was 5.7, with an osmolality of 182 mOsm/Kg.

Formulation 13: This composition was prepared in order to determine the properties of a composition according to the present invention, whereby a lead in is combined with a larger particle size component. A mixed particle size population was prepared by combining particles from Formulation 11 with particles of 19,000 nm in size. The micrometer sized particles were prepared by mixing 30% (w/w) aripiprazole lauroxil in 2% (w/w) Polysorbate and leaving the mixture overnight.

The particles of Formulation 11 and the micrometer sized particles were mixed on a 1:1 weight basis, and were diluted to the desired concentration using Citrate Buffered Saline. The final composition comprised 73.5 mg/ml of Formulation 11, 73.5 mg/ml of the micrometer sized particles, 10 mM CBS, and water. In total, the dosed composition comprised 10.3% (w/w) aripiprazole lauroxil, 1% (w/w) polysorbate 20 in Citrate Buffered Saline and had a pH of 6.6 and an osmolality of 324 mOsm/kg.

A portion of Formulations 11, 12 and 13 was retained for stability testing. The data generated from the stability test is outlined below in Table 6. The data indicates that the compositions are stable over the three month period of testing.

TABLE 6

Stability of Formulations 12-15 over 3 month period

| Formulation No. | Stability time point (months) | Storage Temperature (° C.) | pH | mOs/kg | Mean (nm) 1.44-001i | Mean (nm) 1.62-0.00i |
|---|---|---|---|---|---|---|
| Formulation 11 | 0 (initial) |  | 6.6 | ND | 403 | 378 |
|  | 3 | 5 | 7.15 | 321 | 407 | 394 |
|  | 3 | 25 | 7.22 | 319 | 428 | 416 |
|  | 3 | 40 | 7.04 | 321 | 495 | 529 |
| Formulation 12 | 0 (initial) |  | 5.7 | ND | 509 | 532 |
|  | 3 | 5 | 5.43 | 183 | 433 | 422 |
|  | 3 | 25 | 5.21 | 181 | 594 | 787 |
|  | 3 | 40 | 4.98 | 182 | 750 | 1135 |
| Formulation 13-Peak A | 0 (initial) |  |  |  |  | 240 |
|  | 3 | 5 |  |  |  | 220 |
|  | 3 | 25 |  |  |  | 220 |
|  | 3 | 40 |  |  |  | 263 |
| Formulation 13-Peak B | 0 (initial) |  |  |  |  | 19000 |
|  | 3 | 5 |  |  |  | 13500 |
|  | 3 | 25 |  |  |  | 11000 |
|  | 3 | 40 |  |  |  | 21700 |

The number of dogs dosed in the dog study was 4 per formulation. The dogs were dosed intramuscularly. Samples for pharmacokinetic analysis were collected at regular intervals from dosing until 672 hours (28 days) post dosing.

The concentration of aripiprazole in each respective sample was measured. The mean pharmacokinetic parameters (for all of the dogs in the study) as measured in whole blood is presented in Table 7 below.

TABLE 7

Pharmacokinetic parameter (Aripiprazole)

| Dose | $T_{max}$ (hr) | $C_{max}$ (ng/mL) | $AUC_{last}$ (ng*hr/mL) | $T_{1/2}$ (hr) |
|---|---|---|---|---|
| Aripiprazole lauroxil (approx. 20 μm) formulation | 336 | 8.1 ± 1.8 | 2910 ± 778 | 174 ± 43 |
| Formulation 11 | 204 | 9.0 ± 4.7 | 1893 ± 277 | 89 ± 32 |
| Formulation 12 | 240 | 10.0 ± 4.0 | 2625 ± 981 | 96 ± 14 |
| Formulation 13 | 204 | 4.2 ± 0.8 | 1359 ± 394 | 284 ± 159 |

Figure 5:
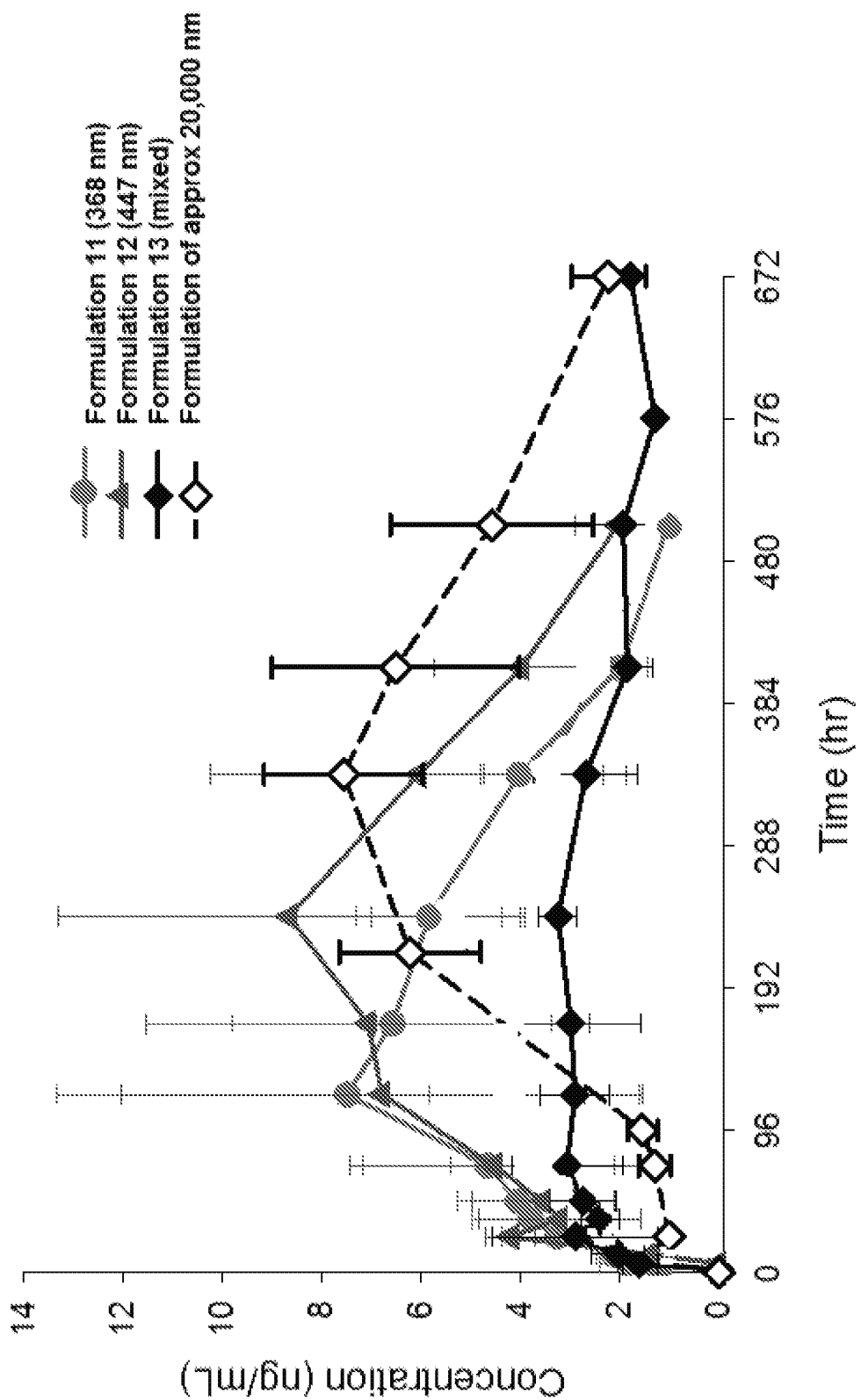
FIG. 5 is a plot of mean aripiprazole concentrations as measured in vivo in dog subjects for Formulations 11, 12 and 13 as compared with a 20,000 nm formulation, which is discussed in Example 5.

The results indicate that Formulations 11, 12 and 13 exhibits a reduced time to $T_{max}$ in comparison to a larger formulation having a particle size of approximately 20 microns. For Formulation 11 a relatively high early exposure to prodrug moiety was observed. For Formulation 13 a fast onset of aripiprazole concentration was observed followed by extended coverage of aripiprazole concentration over time was observed. FIG. 5 depicts the mean aripiprazole concentrations as measured in vivo.

Example 6: Dog Study

Building on the findings of the previous study described which suggested a faster onset and reduced $T_{max}$ in the pharmacokinetic properties of a composition according to the present invention in comparison to compositions having a larger aripiprazole prodrug particle size, the aim of this study was to examine more specifically the impact of using various aripiprazole prodrug particle sizes within the sub 1000 nm range defining the composition of the present invention. Furthermore, the study aimed to determine the pharmacokinetic profile achievable by using a mixture of a formulation of the size range specified by the present invention (less than 1000 nm), with a larger particle size formulation of aripiprazole lauroxil.

Formulation 14: A crude slurry (total 53 g) comprising 13% (w/w) aripiprazole lauroxil composition and 1.3% (w/w) polysorbate 20 which was used as the surface stabilizer was prepared. The ratio of aripirazole lauroxil to surface stabilizer was therefore about 10:1. 10 mM Citrate buffered saline was added as a buffer. The composition was milled in a Nanomill 0.01 having a chamber volume of 100 ml using a straight (pegless) shaft, at a milling speed of 973 rpm for 240 minutes at a temperature of 15° C. The media used was 500 μm Polymill milling media, and the media load was 69%. The final particle size analysis on a Horiba LA 950 determined a mean particle size of 110 nm, a Dv90 of 164 nm a Dv50 of 103 nm and a Dv10 of 67 nm.

Formulation 15: A crude slurry (5.86 g) comprising 15% (w/w) aripiprazole lauroxil and 1% (w/w) polysorbate 20 which was used as the surface stabilizer was first prepared. The total ratio of aripirazole lauroxil to stabilizer was therefore 15:1. Citrate buffered saline was added as a buffer. The composition was milled in a Nanomill 0.01 having a chamber volume of 10 ml using a straight shaft, at a milling speed of 2500 rpm for 105 minutes at a temperature of 15° C. The media used was 500 μm Polymill milling media, and the media load was 69%. The mean particle size of the final composition as measured on a Horiba LA 950 was 192 nm, with a Dv90 of 347, a Dv50 of 153 nm and a Dv10 of 77 nm.

Formulation 16 was a mixture of 100 mg of a composition having a volume based particle size (Dv50) of approximately 100 nm (Formulation 16 above) with 100 mg of a larger particle size composition of aripirazole lauroxil having a volume based particle size (Dv50) of approximately 20 μm (20,000 nm). Citrate buffered saline was added as a buffer.

Formulation 17: A crude slurry (53 g) comprising 13% (w/w) aripiprazole lauroxil was perpared. Polysorbate, 1.3% (w/w) and 2% (w/w) dextrose were added as surface stabilizers. The total ratio of aripiprazole lauroxil to stabilizer was about 10:1. Arginine was added as a buffer. Milling of the composition was carried out using a NanoMill 0.01 having a chamber volume of 100 ml and a straight shaft. The milling speed was 973 rpm and the composition was milled for 240 minutes at 15° C. The milling media was 500 μm PolyMill milling media. The media load of 69%. The mean particle size as measured on a Horiba LA 950 was 105 nm, with a Dv90 of 155 nm, a Dv50 of 97 nm and a Dv10 of 65 nm.

A total of 4 dogs per formulation were used in the study and all doses were intramuscularly administered. Formulation 14 was dosed at a level equivalent to 100 mg of aripirazole or 147 mg of aripiprazole lauroxil and the dose volume was 1.1 ml per animal. Formulation 15 was dosed at a level equivalent to 100 mg of aripirazole or 147 mg of aripiprazole lauroxil and the dose volume was 1 ml per animal. Formulation 16 was dosed at a level equivalent to 200 mg of aripirazole (100 mg attributed to each particle size component in the mixture) or 147 mg of aripiprazole lauroxil and the dose volume was 2.1 ml per animal. Formulation 17 was dosed at a level equivalent to 100 mg of aripirazole or 147 mg of aripiprazole lauroxil and the dose volume was 1.1 ml per animal. Samples for pharmacokinetic analysis were collected at regular intervals from dosing until 672 hours (28 days) post dosing.

The collected samples of whole blood were analyzed. The concentrations of aripiprazole lauroxil and aripiprazole were measured. The mean concentration values for aripiprazole are shown in Table 8 below.

TABLE 8

Mean aripirazole concentrations for Formulations 14-17

Mean aripirazole concentration in whole blood

| Time (hrs) | Formulation 14 (100 nm) | Formulation 15 (150 nm) | Formulation 16 (100 + 20,000) | Formulation 17 (100 nm) |
|---|---|---|---|---|
| 2 | 12.00 | 2.20 | 7.31 | 5.12 |
| 6 | 15.10 | 5.38 | 8.77 | 4.62 |
| 12 | 11.18 | 7.63 | 7.05 | 6.30 |
| 24 | 18.07 | 12.54 | 10.26 | 12.64 |
| 36 | 12.56 | 8.26 | 6.69 | 7.30 |
| 48 | 16.38 | 9.46 | 11.76 | 12.83 |
| 72 | 13.55 | 8.17 | 9.11 | 12.05 |
| 120 | 8.06 | 6.53 | 5.45 | 7.28 |
| 168 | 7.02 | 8.28 | 4.08 | 5.62 |
| 240 | 7.50 | 6.39 | 3.48 | 2.46 |
| 336 | 5.11 | 2.45 | 2.36 | 1.27 |
| 408 | 4.08 | 2.07 | 1.66 | 2.68 |
| 504 | 3.56 | 1.65 | 1.15 | |
| 576 | 2.2 | 1.01 | | |
| 672 | 1.98 | | | |

TABLE 9

Pharmacokinetic parameters for analyte aripiprazole

| Dose | $T_{max}$ (hr) | $C_{max}$ (ng/mL) | $AUC_{last}$ (ng*hr/mL) | $T_{1/2}$ (hr) |
|---|---|---|---|---|
| Aripiprazole lauroxil (20 μm) formulation | 336 | 8.1 ± 1.8 | 2910 ± 778 | 174 ± 43 |
| Formulation 14 | 24 | 12.8 ± 5.6 | 1661 ± 147 | 110 ± 54 |
| Formulation 15 | 24 | 12.8 ± 5.2 | 2613 ± 684 | 118 ± 47 |
| Formulation 16 | 48 | 19.0 ± 9.7 | 4152 ± 1128 | 228 ± 86 |
| Formulation 17 | 36 | 14.9 ± 6.2 | 1854 ± 431 | 104 ± 66 |

TABLE 10

Pharmacokinetic parameters for analyte aripiprazole lauroxil (prodrug)

| Dose | $C_{max}$ (ng/mL) | $AUC_{last}$ (ng*hr/mL) | $T_{1/2}$ (hr) |
|---|---|---|---|
| Aripiprazole lauroxil (20 μm) formulation | 4.53 | 112.7 | 332 |
| Formulation 14 | 441 | 4201 | 16.7 |
| Formulation 15 | 47.4 | 597 | 13.7 |
| Formulation 16 | 500 | 4824 | 26 |
| Formulation 17 | 215 | 2812 | 25 |

Figure 6:
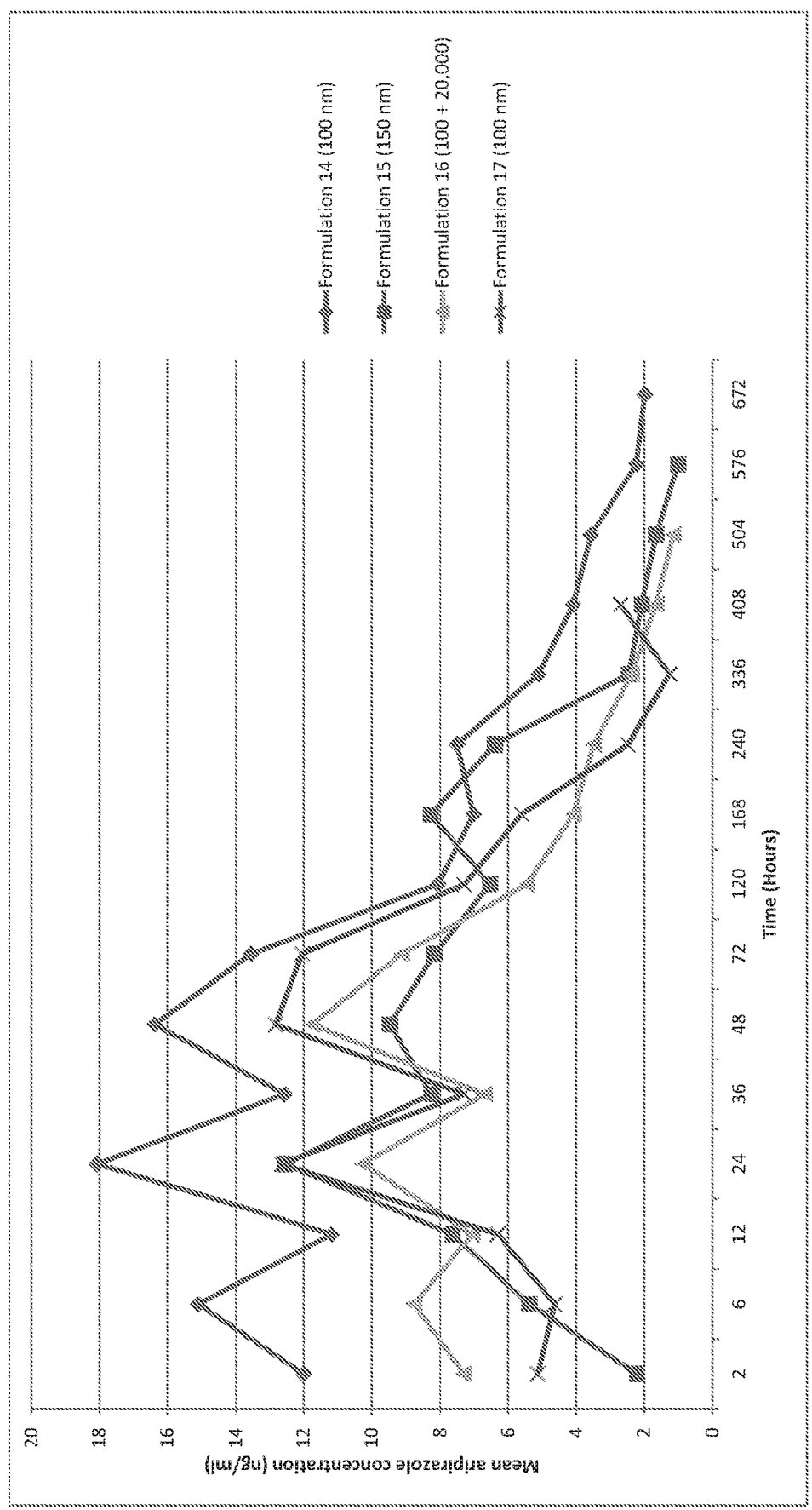
FIG. 6 is a plot of mean aripiprazole concentrations as measured in vivo in dog subjects for Formulations 14 to 17 of Example 6.

FIG. 6 depicts the mean aripiprazole concentrations as measured in vivo in a dog model for Formulations 14 to 17. All of formulations 14 to 17 were noted to have a reduced onset time and $T_{max}$ when compared to the aripiprazole lauroxil formulation of approximately 20 microns in size.

Example 7: Dog Study

The purpose of this example was to determine the Pharmacokinetic parameters for various aripiprazole compositions in an animal model. The study focused in particular on the effect of dose level and quantity of surface stabilizer on levels of aripiprazole prodrug and aripiprazole measured in vivo in dogs.

Formulation 18: A crude slurry (116 g) was first prepared in which Polysorbate 20 was used as a surface stabilizer at a level of 2% (w/w). A citrate buffer was used at an amount of 15:1. Milling of the composition was carried out using a NanoMill 0.01 having a chamber volume of 100 ml and a pegged shaft. The milling was initially conducted at a speed of 3100 rpm for 45 minutes and then at 700 rpm for 20 minutes. The milling temperature was 15° C. 500 µm PolyMill milling media was used. The media load was 89%. Total dose strength was equivalent to 100 mg of aripiprazole. The particle size distribution as measured after formulation was found to have a Dv90 value of 296.8 nm, a Dv50 value of 166.1 nm, and a Dv10 value of 84.0 nm.

Formulation 19: A crude slurry (58 g) was first prepared in which Polysorbate 20 was used as a surface stabilizer at a level of 1% (w/w). A citrate buffer was used at an amount of 28:1. Milling took placed on a NanoMill 0.01 mill having a 50 ml chamber and a pegged shaft. The milling speed was 962 rpm for 180 minutes which was reduced to 450 rpm for 60 minutes thereafter. The milling process took place at a temperature of between 8 and 10° C. The media used was 500 µm PolyMill milling media. The total media load was 89%. Total dose strength was equivalent to 300 mg of aripiprazole. The particle size distribution as measured after formulation was found to have a Dv90 value of 679.1 nm, a Dv50 value of 242.6 nm, and a Dv10 value of 88.1 nm.

Formulation 20: A crude slurry (116 g) was first prepared in which Polysorbate 20 was used as a surface stabilizer at a level of 2% (w/w). A citrate buffer was used at an amount of 15:1. Milling was carried out using a NanoMill 0.01 mill having a chamber volume of 100 ml and a pegged shaft. The milling speed was 3100 rpm for 45 minutes and 700 rpm for 20 minutes. The milling temperature was 15° C. The media used was 500 µm PolyMill milling media. The media load was 89%. Total dose strength was equivalent to 300 mg of aripiprazole. The particle size distribution as measured after formulation was found to have a Dv90 value of 296.8 nm, a Dv50 value of 166.1 nm, and a Dv10 value of 84.0 nm.

Formulation 21: A crude slurry (116 g) was first prepared in which Polysorbate 20 was used as a surface stabilizer at a level of 3% (w/w). A citrate buffer was used at an amount of 10:1. Milling was carried out using a NanoMill 0.01 having a 100 ml chamber and pegged shaft. The milling speed was initially 3100 rpm for a period of 4 minutes, reduced to 389 rpm for 50 minutes, then increased to 3100 rpm for 40 minutes and finally reduced to 450 rpm for 90 minutes. The milling temperature was 8° C. The media used was 500 µm PolyMill milling media. The total media load was 89%. The final dose strength of the composition was equivalent to 300 mg of aripiprazole. The particle size distribution as measured after formulation was found to have a Dv90 value of 361.8 nm, a Dv50 value of 151.8 nm, and a Dv10 value of 76.4 nm.

Formulation 22: A crude slurry (total 116 g) was first prepared in which Polysorbate 20 was used as a surface stabilizer at a level of 2% (w/w). A phosphate and sodium citrate buffer was used at an amount of 15:1. Milling was carried out using a NanoMill 0.01 having a 100 ml chamber and pegged shaft. The milling speed was initially 3100 rpm for a period of 45 minutes which was then reduced to 700 rpm for 20 minutes. The milling temperature was 15° C. The media used was 500 µm PolyMill milling media. The total media load was 89%. Total dose strength was equivalent to 300 mg of aripiprazole. The particle size distribution as measured after formulation was found to have a Dv90 value of 306 nm, a Dv50 value of 171 nm, and a Dv10 value of 86 nm.

Formulation 23: A crude slurry (total 116 g) was first prepared comprising Polysorbate 20 used as a surface stabilizer at a level of 2% (w/w). A citrate buffer was used at an amount of 15:1. Milling was carried out using a NanoMill 0.01 having a 100 ml chamber and pegged shaft. The milling speed was initially 3100 rpm for a period of 45 minutes which was then reduced to 700 rpm for 20 minutes. The milling temperature was 15° C. The media used was 500 µm PolyMill milling media. The total media load was 89%. Total dose strength was equivalent to 700 mg of aripiprazole. The particle size distribution as measured after formulation was found to have a Dv90 value of 296.8 nm, a Dv50 value of 166.1 nm, and a Dv10 value of 84.0 nm.

Formulation 24: A crude slurry (total 116 g) was first prepared comprising Polysorbate 20 was used as a surface stabilizer at a level of 2% (w/w). A citrate/sucrose buffer was used at an amount of 15:1. Milling was carried out using a NanoMill 0.01 having a 100 ml chamber and pegged shaft. The milling speed was initially 3100 rpm for a period of 45 minutes which was then reduced to 700 rpm for 20 minutes. The milling temperature was 15° C. The media used was 500 µm PolyMill milling media. The total media load was 89%. Total dose strength was equivalent to 300 mg of aripiprazole. The particle size distribution as measured after formulation was found to have a Dv90 value of 301 nm, a Dv50 value of 168 nm, and a Dv10 value of 84 nm.

A total of 4 dogs were used for each formulation. All formulations were dosed intramuscularly. Formulation 18 was dosed at a level of 147 mg aripiprazole lauroxil (equivalent to 100 mg aripiprazole) and the dose volume was 0.67 ml per animal. Formulations 19, 20, 21, 22 and 24 were dosed at a level of 441 mg aripiprazole lauroxil (equivalent to 300 mg of aripiprazole) and the dose volume was 2 ml per animal. Formulation 23 was dosed at a level of 1029 mg of aripiprazole lauroxil (equivalent to 700 mg of aripirazole) and the dose volume was 4.7 ml per animal.

Figure 7:
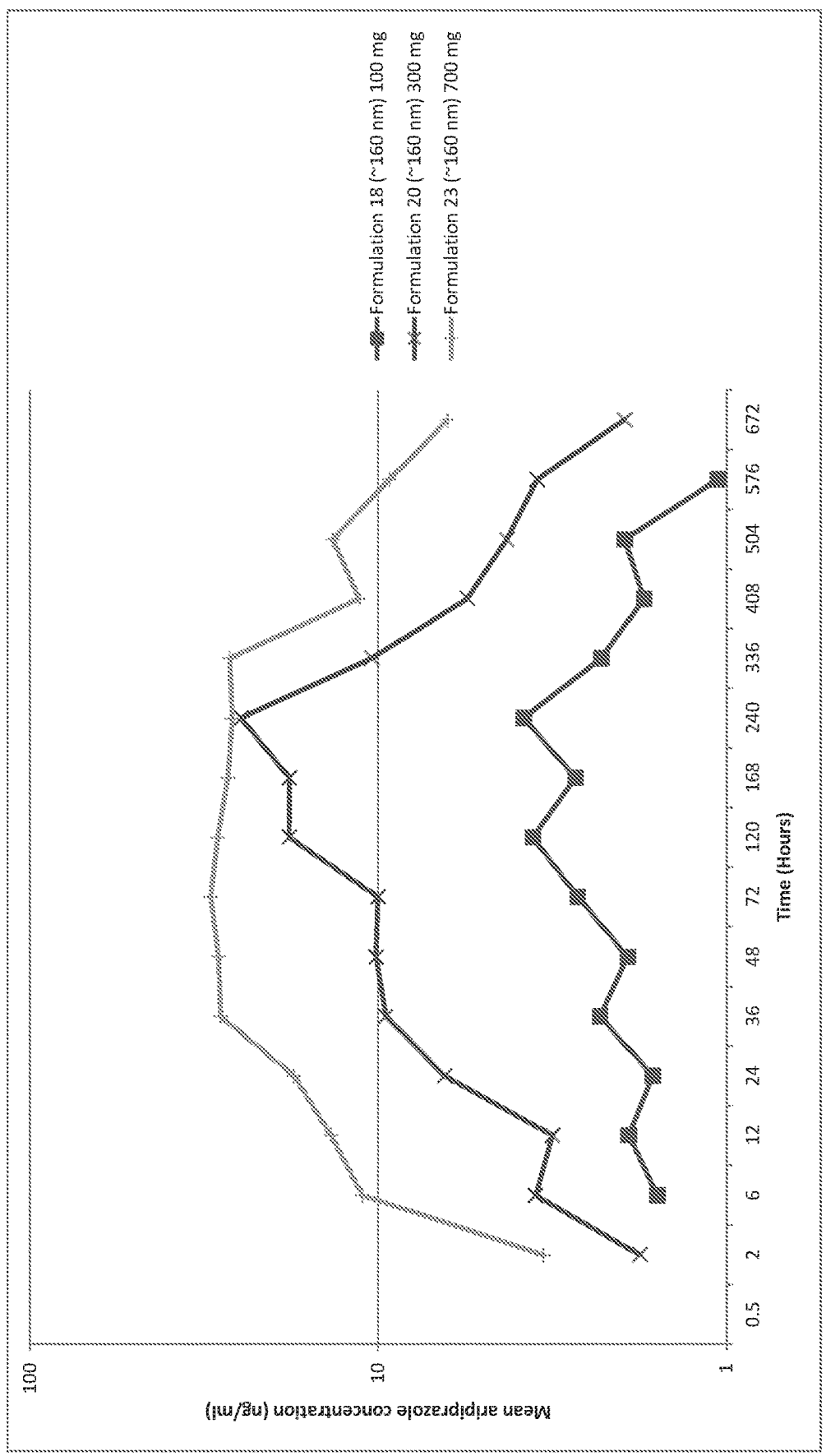
FIG. 7 is a plot of the mean aripiprazole concentrations as measured in vivo in dog subjects for Formulations 18, 20 and 23 of Example 7.
Figure 8:
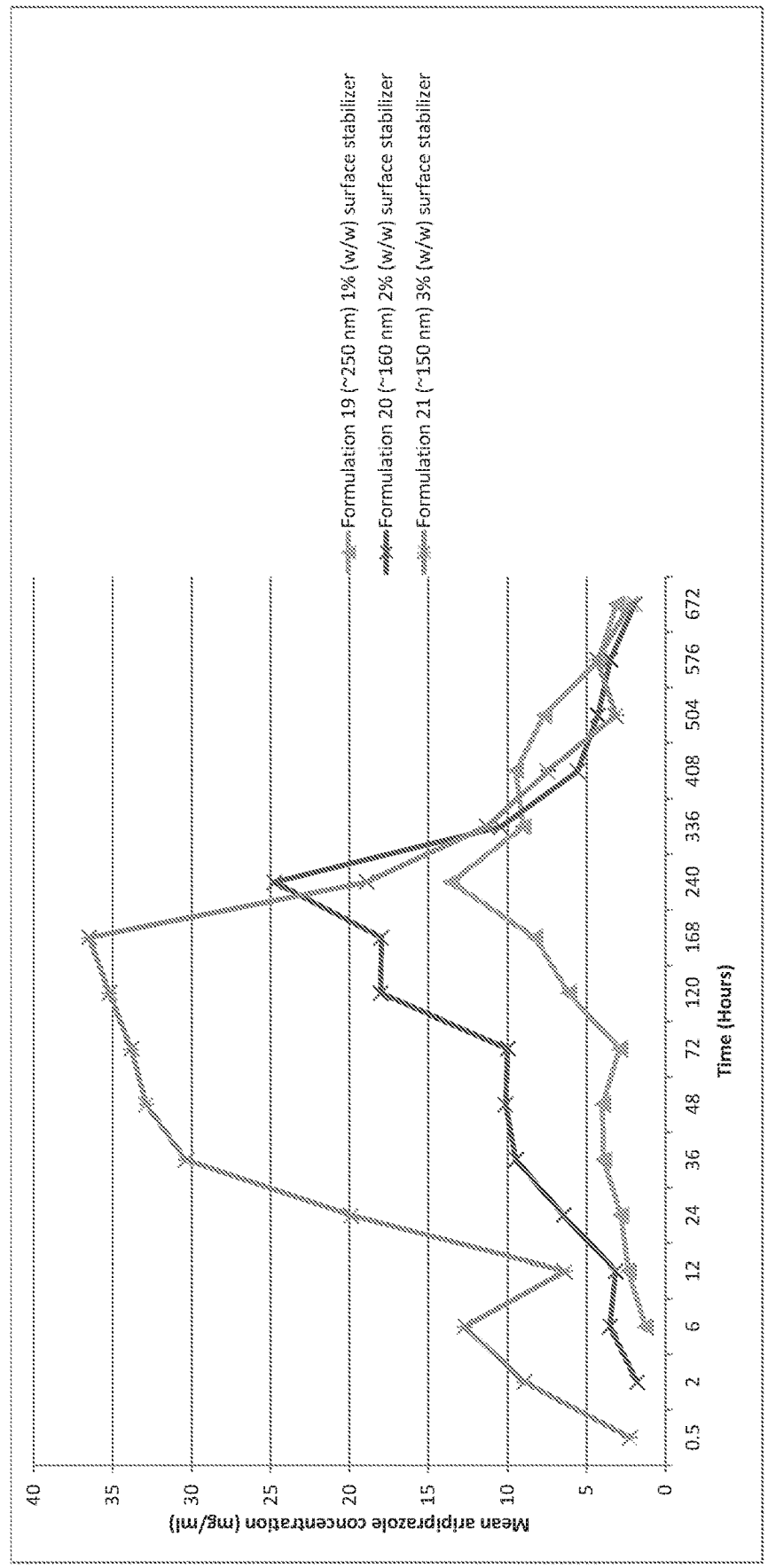
FIG. 8 is a plot of mean aripiprazole concentrations as measured in vivo in dog subjects for Formulations 19, 20 and 21 of Example 7.

The mean aripiprazole concentrations as measured in whole blood are shown below in Table 11. These values are also plotted in FIGS. 7 and 8. FIG. 7 directly compares the mean aripiprazole concentrations as measured in vivo for Formulations 18, 20 and 23. FIG. 8 directly compares the mean aripiprazole concentrations as measured in vivo for Formulations 19, 20 and 21.

TABLE 11

Mean aripiprazole concentrations

| Time point (hr) | Mean aripiprazole concentration in whole blood (ng/ml) | | | | | | |
| --- | --- | --- | --- | --- | --- | --- | --- |
| | Formulation 18 (~160 nm) | Formulation 19 (~250 nm) | Formulation 20 (~160 nm) | Formulation 21 (~150 nm) | Formulation 22 (~170 nm) | Formulation 23 (~160 nm) | Formulation 24 (~170 nm) |
| 0.5 | — | — | — | 2.24 | — | — | — |
| 2 | — | — | 1.78 | 8.94 | 4.73 | 3.36 | 2.12 |
| 6 | 1.58 | 1.27 | 3.53 | 12.73 | 7.85 | 11.07 | 5.058 |
| 12 | 1.91 | 2.35 | 3.16 | 6.37 | 4.19 | 13.66 | 5.20 |

TABLE 11-continued

Mean aripiprazole concentrations

Mean aripiprazole concentration in whole blood (ng/ml)

| Time point (hr) | Formulation 18 (~160 nm) | Formulation 19 (~250 nm) | Formulation 20 (~160 nm) | Formulation 21 (~150 nm) | Formulation 22 (~170 nm) | Formulation 23 (~160 nm) | Formulation 24 (~170 nm) |
|---|---|---|---|---|---|---|---|
| 24  | 1.63 | 2.81  | 6.45  | 19.90 | 13.43 | 17.43 | 9.27  |
| 36  | 2.30 | 3.93  | 9.48  | 30.35 | 17.85 | 28.33 | 10.55 |
| 48  | 1.92 | 3.99  | 10.13 | 32.85 | 14.50 | 28.75 | 11.54 |
| 72  | 2.67 | 2.90  | 10.01 | 33.80 | 17.98 | 30.28 | 10.00 |
| 120 | 3.60 | 6.14  | 18.02 | 35.20 | 16.68 | 28.91 | 14.14 |
| 168 | 2.71 | 8.26  | 17.97 | 36.48 | 18.18 | 27.00 | 18.75 |
| 240 | 3.82 | 13.58 | 24.75 | 18.93 | 16.58 | 26.23 | 20.38 |
| 336 | 2.29 | 9.00  | 10.42 | 11.36 | 6.50  | 26.70 | 14.53 |
| 408 | 1.73 | 9.48  | 5.56  | 7.45  | 8.47  | 11.31 | 6.19  |
| 504 | 1.96 | 7.70  | 4.27  | 3.13  | 4.09  | 13.51 | 5.46  |
| 576 | 1.06 | 4.23  | 3.49  | 4.33  | 6.17  | 9.24  | 3.21  |
| 672 | —    | 3.11  | 1.96  | 2.25  | 4.01  | 6.33  | 2.44  |

The mean pharmacokinetic parameters for aripiprazole levels as calculated for each group are shown in Table 12 shown below.

TABLE 12

Pharmacokinetic parameters for analyte aripiprazole

| Dose | $C_{max}$ (ng/mL) | $AUC_{last}$ (ng*hr/mL) |
|---|---|---|
| Formulation 18 | 4 | 1539 |
| Formulation 19 | 13.9 | 5518 |
| Formulation 20 | 26.6 | 7258 |
| Formulation 21 | 45.9 | 10449 |
| Formulation 22 | 23 | 8402 |
| Formulation 23 | 39.1 | 15248 |
| Formulation 24 | 21.2 | 7595 |

From the results obtained the following conclusions can be reached regarding the effect of dose level on exposure. Formulation 18 contained a 100 mg dose of aripiprazole, Formulation 23 contained a 700 mg dose and Formulations 19-22 and 24 contained a 300 mg dose. It is noted that increasing the dose did lead to an increase in the level of aripiprazole lauroxil (prodrug) detected in the blood. Secondly, it is noted that the level of aripiprazole measured was increased by increasing the dose.

With regard to the effect of the percentage of polysorbate 20 present on the overall prodrug exposure, the following observations were made. Formulation 19 had the lowest level of polysorbate 20 at 1% (w/w) of the overall composition. Formulations 18, 20, 22, 23 and 24 had a higher level at 2% (w/w) and Formulation 21 had the highest level at 3% (w/w). It was found that increasing the percentage of polysorbate 20 in the composition resulted in a higher free component of the dose. Accordingly, the level of aripiprazole and prodrug in blood was found to be increased by increasing the percentage of polysorbate 20 present.

Example 8: Dog Study

The purpose of this final dog study was to determine the effect of particle size and active surface stabilizer ratio on the levels of aripiprazole lauroxil and aripiprazole measured in whole blood following a single intramuscular injection in dogs. The samples were prepared essentially of the same constituents, whereby either the particle size of the aripiprazole lauroxil particles was varied and/or the total quantity of surface stabilizer present was varied. The formulations were prepared as follows:

Formulation 25 was prepared from a crude slurry (total 136 g) comprising 26% w/w aripiprazole lauroxil and 1.53% w/w polysorbate 20 as a surface stabilizer (i.e. approximately 17:1 ratio of active to surface stabilizer). To this, 10 mM phosphate buffered saline (pH 6.8) was added along with 26 mM of sodium citrate. (Polymill milling media of 250 μm in size was added in an amount to bring the total media load to 80%. The slurry was placed inside a 100 ml chamber of a NanoMill® 0.01 mill having a pegged shaft and milled at 1000 rpm for a total of 1860 minutes at a temperature of 5° C. The final composition prior to dosing had a mean particle size of 113 nm, a Dv90 of 166 nm, a Dv50 of 107 nm and a Dv10 of 69 nm. [0245] Formulation 26 was prepared from a crude slurry (total 136 g) comprising 26% w/w aripiprazole lauroxil and 1.53% w/w polysorbate 20 as a surface stabilizer (i.e. approximately 17:1 ratio of active to surface stabilizer). To this, 10 mM phosphate buffered saline (pH 6.8) was added along with 26 mM of sodium citrate. Polymill milling media of 500 μm in size was added, such that the total media load was 80%. The slurry was milled in a NanoMill® 0.01 mill having a 100 ml chamber and pegged shaft at 1000 rpm for 723 minutes at a milling temperature of 5° C. The final composition had a mean particle size of 202 nm, a Dv90 of 366 nm, a Dv50 of 167 nm, and a Dv10 of 82 nm.

Figure 18:
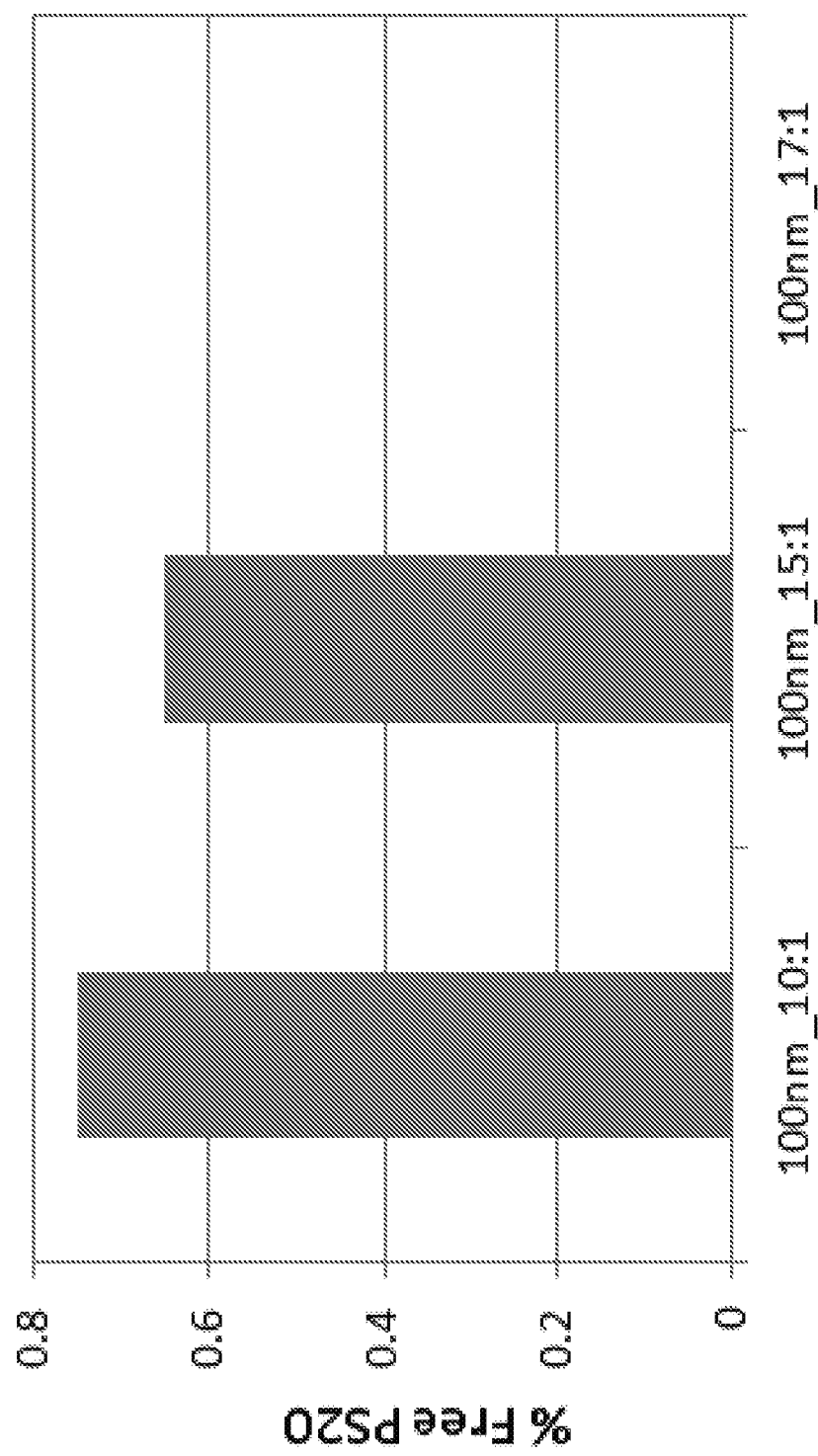
FIG. 18A depicts the amount of free polysorbate 20 for formulations 25, 28 and 29 (formulations at fixed surface area and increasing polysorbate 20 concentration) determined by HPLC.
FIG. 18B depicts the amount of dissolved aripiprazole lauroxil for formulations 25, 28 and 29 (formulations at fixed surface area and increasing polysorbate 20 concentration) determined by HPLC.
Figure 18:
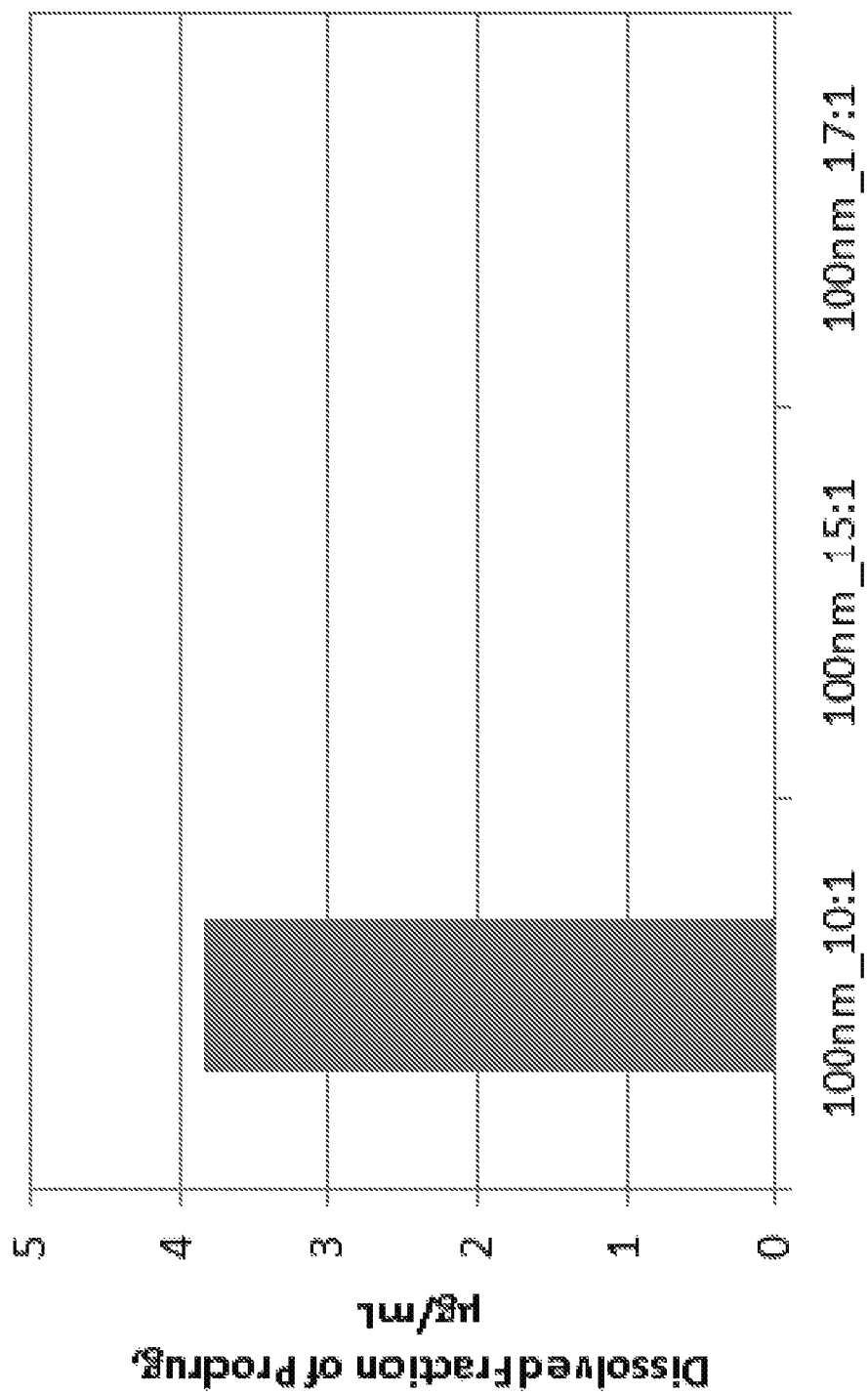
Figure 19:
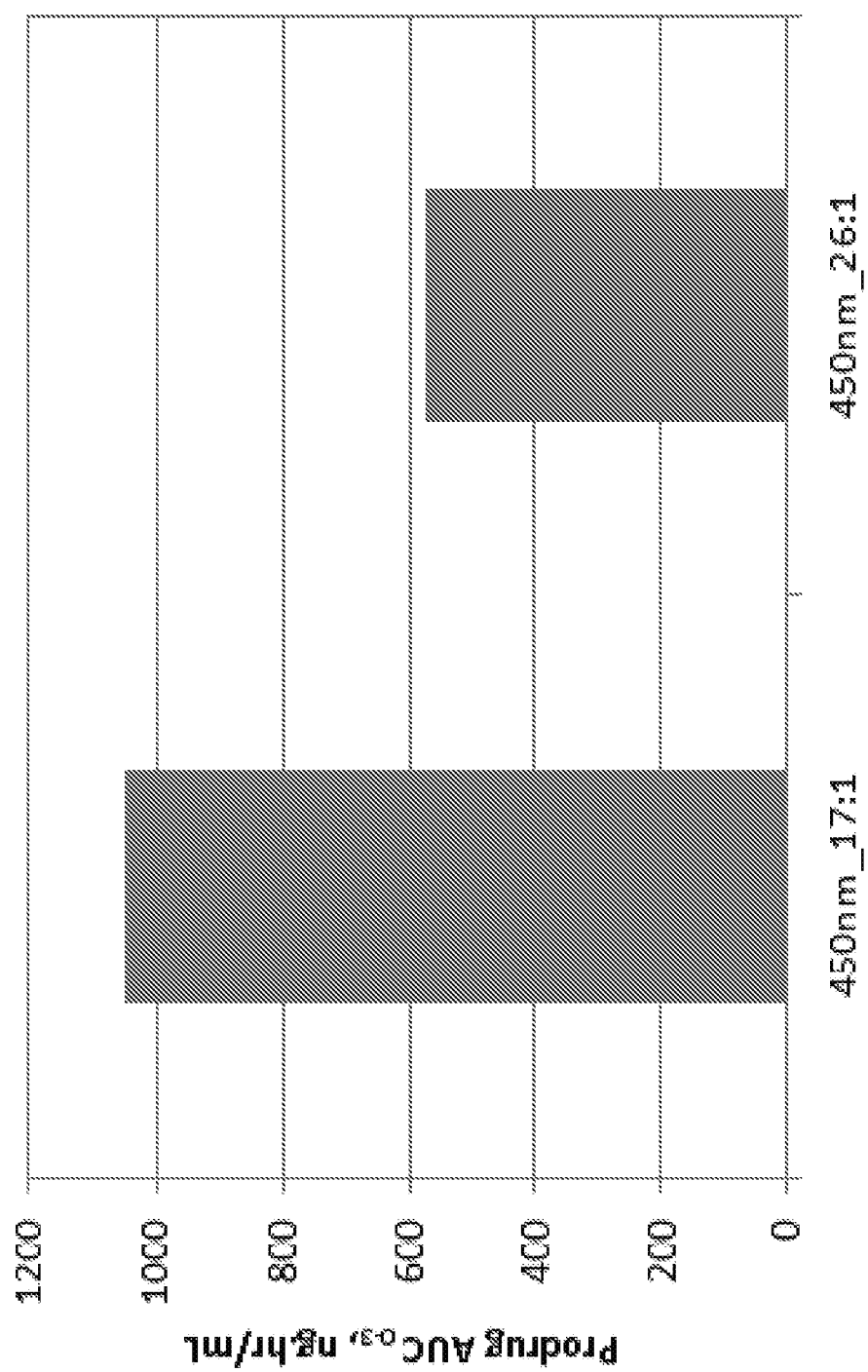
FIG. 19A depicts the AUC of aripiprazole lauroxil for formulations 27 and 30 (formulations at fixed surface area and increasing polysorbate 20 concentration) from dog study.
FIG. 19B depicts the AUC of aripiprazole for formulations 27 and 30 (formulations at fixed surface area and increasing polysorbate 20 concentration) from dog study.
Figure 19:
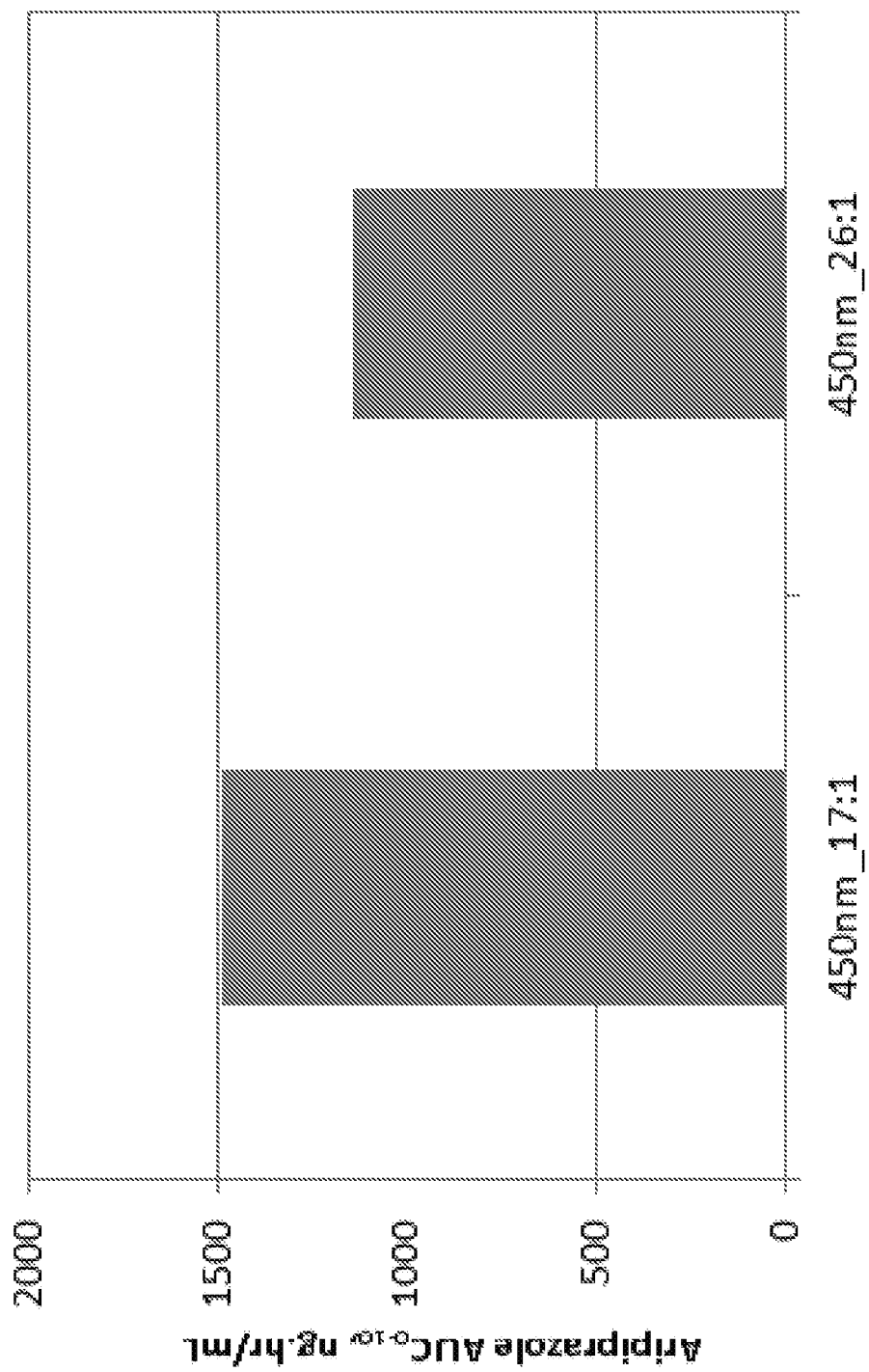

The viscosity of Formulation 26 was determined at various shear rates at a temperature of 25° C. At a shear rate of 1 s$^{-1}$, the viscosity was determined to be about 9 cP. The viscosity profile was observed to follow a shear thinning type profile where a Newtonian region was observed between 100 and 1000 s$^{-1}$, with the shear rate being maintained at approximately 3.5-4 cP. This test shows that Formulation 26 has favourable viscosity characteristics in the context of an injectable formulation where the shear rate is generally increased when injecting the composition. FIG. 18 depicts the viscosity versus shear curve for Formulation 26.

Formulation 27 was prepared from a crude slurry (total 136 g) comprising 26% w/w aripiprazole lauroxil and 1.53% w/w polysorbate 20 as a surface stabilizer (i.e. approximately 17:1 ratio of active to surface stabilizer). To this, 10 mM phosphate buffered saline (pH 6.8) was added along with 26 mM of sodium citrate. Polymill milling media having a size of 500 µm was added, the total media load being 80%. The slurry was placed inside a 100 ml chamber of a NanoMill® 0.01 mill having a pegged shaft and milled at 1000 rpm for a total of 538 minutes at a temperature of 5° C. The final composition had a mean particle size of 445 nm, a Dv90 of 769 nm, a Dv50 of 398 nm, and a Dv10 of 180 nm.

Formulation 28 was prepared from a crude slurry (total 136 g) comprising 26% w/w aripirazole lauroxil and 1.73% w/w polysorbate 20 as a surface stabilizer (i.e. approximately 15:1 ratio of active to surface stabilizer). To this, 10 mM phosphate buffered saline (pH 6.8) was added along with 26 mM of sodium citrate. Polymill milling media of 250 µm in size was added in an amount to bring the total media load to 80%. The slurry was milled in a NanoMill® 0.01 mill having a 100 ml chamber and pegged shaft, at 1000 rpm for a total of 1200 minutes at a milling temperature of 5° C. The final composition was found to have a mean particle size of 109 nm, a Dv90 of 161 nm, a Dv50 of 102 nm, and a Dv10 of 68 nm.

Formulation 29 was prepared from a crude slurry (total 136 g) comprising 26% w/w aripirazole lauroxil and 2.6% w/w polysorbate 20 as a surface stabilizer (i.e. approximately 10:1 ratio of active to surface stabilizer). To this, 10 mM phosphate buffered saline (pH 6.8) was added along with 26 mM of sodium citrate. Polymill milling media of 250 µm in size was added in an amount to bring the total media load to 80%. The slurry was placed inside a 100 ml chamber of a NanoMill® 0.01 mill having a pegged shaft and milled at 1000 rpm for a total of 1200 minutes at a temperature of 5° C. The final composition was found to have a mean particle size of 113 nm, a Dv90 of 168 nm, a Dv50 of 106 nm and a Dv10 of 68 nm.

Formulation 30 was prepared from a crude slurry (total 136 g) comprising 26% w/w aripirazole lauroxil and 1% w/w polysorbate 20 as a surface stabilizer (i.e. approximately 26:1 ratio of active to surface stabilizer). To this, 10 mM phosphate buffered saline (pH 6.8) was added along with 26 mM of sodium citrate. Polymill milling media of 500 µm in size was added in an amount to bring the total media load to 80%. The slurry was placed inside a 100 ml chamber of a NanoMill® 0.01 mill having a pegged shaft and milled at 1000 rpm for a total of 90 minutes at a temperature of 5° C. The final composition was found to have a mean particle size of 449 nm, a Dv90 of 765 nm, a Dv50 of 407 nm, and a Dv10 of 184 nm.

For each of the Formulations 25-30 described above, the level of free surface stabilizer and the dissolved aripiprazole lauroxil was determined experimentally using HLPC analysis as set out in Table 13 below. For some of the formulations the amount of free surface stabilizer or the dissolved aripiprazole lauroxil was less than the level of detection, abbreviated <LOD in the Table.

TABLE 13

Measurement of free surface stabilizer in composition

| Formulation number | Approximate particle size and API:surface stabilizer ratio | % w/w of total surface stabilizer | % w/w of free surface stabilizer | Dissolved API (µg/mL) |
|---|---|---|---|---|
| Formulation 25 | 100 nm 17:1 | 1.5 | <LOD | <LOD |
| Formulation 26 | 200 nm 17:1 | 1.5 | 0.24 | 1.51 |
| Formulation 27 | 450 nm 17:1 | 1.5 | 0.65 | 3.73 |
| Formulation 28 | 100 nm 15:1 | 1.7 | <LOD | <LOD |
| Formulation 29 | 100 nm 10:1 | 2.6 | 0.75 | 3.83 |
| Formulation 30 | 450 nm 26:1 | 1.0 | <LOD | <LOD |

Each of the aforementioned Formulations 25-30 were dosed intramuscularly into 4 male dogs. For each formulation, the dose level per animal was equivalent to 300 mg of aripiprazole or 441 mg of aripiprazole lauroxil. For each dosed sample, the target dose volume was 1.6 mL per animal. Whole blood was collected over the following time points post dosing (hours): 0.25, 0.5, 1, 2, 3, 6, 12, 24, 36, 48, 60, 72, 120, 168, 240, 336, 408, 504, 576, and 672. The levels of aripiprazole and aripiprazole lauroxil were analyzed in whole blood over the aforementioned time points, the mean values are respectively depicted in Table 14 and Table 15 below.

TABLE 14

Mean aripiprazole concentration values

Aripiprazole concentration in whole blood (ng/ml)

| Time | Formulation 25 100 nm 17:1 | Formulation 26 200 nm 17:1 | Formulation 27 450 nm 17:1 | Formulation 28 100 nm 15:1 | Formulation 29 100 nm 10:1 | Formulation 30 450 nm 26:1 |
|---|---|---|---|---|---|---|
| 0.25 | | | | | | |
| 0.50 | | | | 3.33 | 1.49 | 1.77 |
| 1 | 1.46 | 1.94 | 1.115 | 3.27 | 5.05 | |
| 2 | 2.14 | 2.77 | 1.3 | 5.61 | 9.86 | 1.63 |
| 3 | 1.85 | 3.29 | 1.97 | 6.11 | 12.80 | 2.50 |
| 6 | 1.70 | 5.59 | 2.35 | 5.57 | 12.93 | 2.48 |
| 12 | 3.06 | 7.30 | 4.48 | 6.34 | 12.13 | 5.14 |
| 24 | 4.53 | 10.02 | 7.15 | 8.30 | 14.37 | 9.34 |
| 36 | 5.18 | 12 | 7.19 | 8.80 | 22.11 | 9.71 |
| 48 | 4.77 | 9.75 | 9.60 | 8.94 | 22.49 | 11.47 |
| 60 | 6.80 | 10.54 | 8.74 | 10.09 | 28.13 | 11.63 |
| 72 | 6.58 | 8.33 | 13.55 | 11.08 | 35.36 | 15.48 |
| 120 | 24.33 | 19.55 | 39.70 | 37.25 | 45.58 | 37.53 |
| 168 | 9.43 | 8.22 | 11.94 | 11.34 | 11.57 | 17.68 |
| 240 | 9.81 | 9.60 | 10.2 | 8.53 | 11.15 | 18.64 |

TABLE 15

Mean aripiprazole lauroxil concentration (ng/ml)

| Time (hr) | Formulation 25 100 nm 17:1 | Formulation 26 200 nm 17:1 | Formulation 27 450 nm 17:1 | Formulation 28 100 nm 15:1 | Formulation 29 100 nm 10:1 | Formulation 30 450 nm 26:1 |
|---|---|---|---|---|---|---|
| 0.25 | 7.28 | 140.16 | 166.03 | 219.85 | 222.95 | 13.52 |
| 0.5 | 5.07 | 50.40 | 138.80 | 168.01 | 176.55 | 13.26 |
| 1 | 15.91 | 156.47 | 72.85 | 197.35 | 52.20 | 17.30 |
| 2 | 10.66 | 150.50 | 71.03 | 129.28 | 112 | 20.82 |
| 3 | 8.1 | 116 | 49.58 | 124.15 | 212.70 | 14.37 |
| 6 | 9.93 | 76.28 | 24.94 | 70.05 | 191.53 | 9.14 |
| 12 | 6.57 | 33.25 | 17.41 | 45.68 | 76.99 | 9.62 |
| 24 | 4.81 | 10.71 | 10.91 | 14.21 | 24.15 | 8.31 |
| 36 | 3.03 | 8.59 | 7.02 | 9.81 | 18.84 | 7.03 |
| 48 | 3.19 | 4.40 | 6.20 | 10.28 | 14.27 | 5.74 |
| 60 | 5.36 | 6.92 | 7.18 | 12.78 | 14.25 | 7.01 |
| 72 | 3.87 | 3.69 | 6.66 | 10.37 | 10.31 | 6.09 |
| 120 | 17.35 | 5.26 | 5.57 | 13.33 | 9.01 | 6.07 |
| 168 | 3.33 | 1.46 | 1.99 | 3.17 | 2.60 | 2.92 |
| 240 | 2.09 | | | 1.40 | 3.54 | 1.62 |

Figure 11:
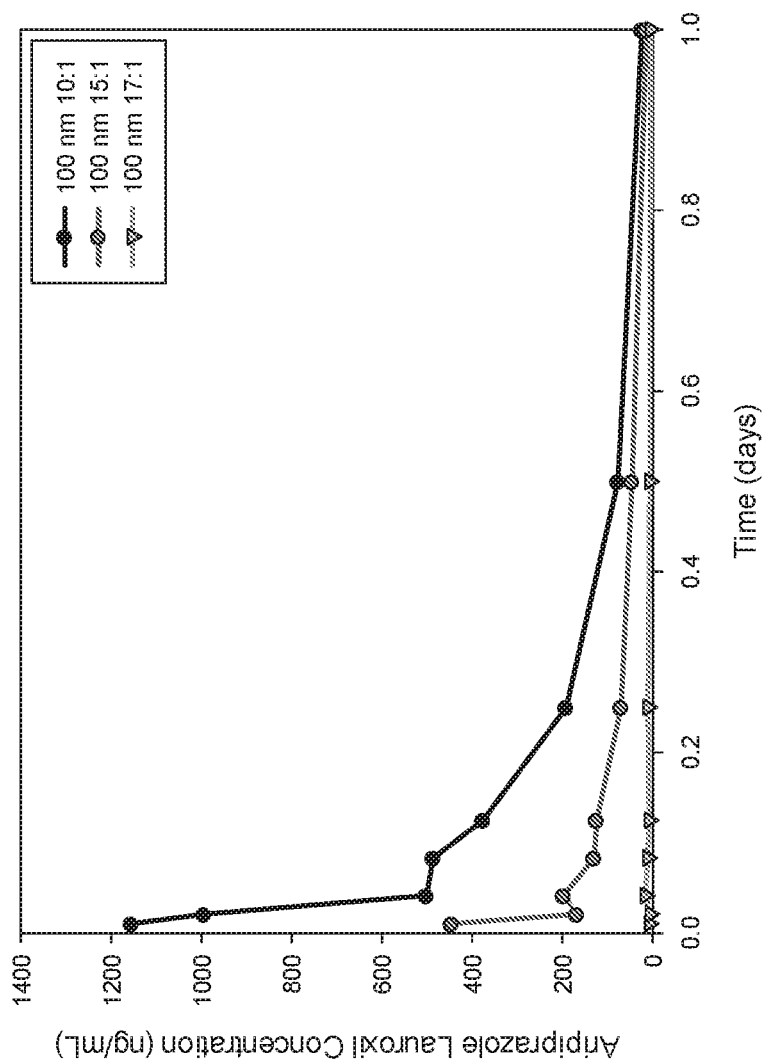
FIG. 11 is a plot of the mean aripiprazole lauroxil concentrations as measured in vivo in dog subjects for Formulations 25, 28 and 29 as discussed in Example 8.
Figure 12:
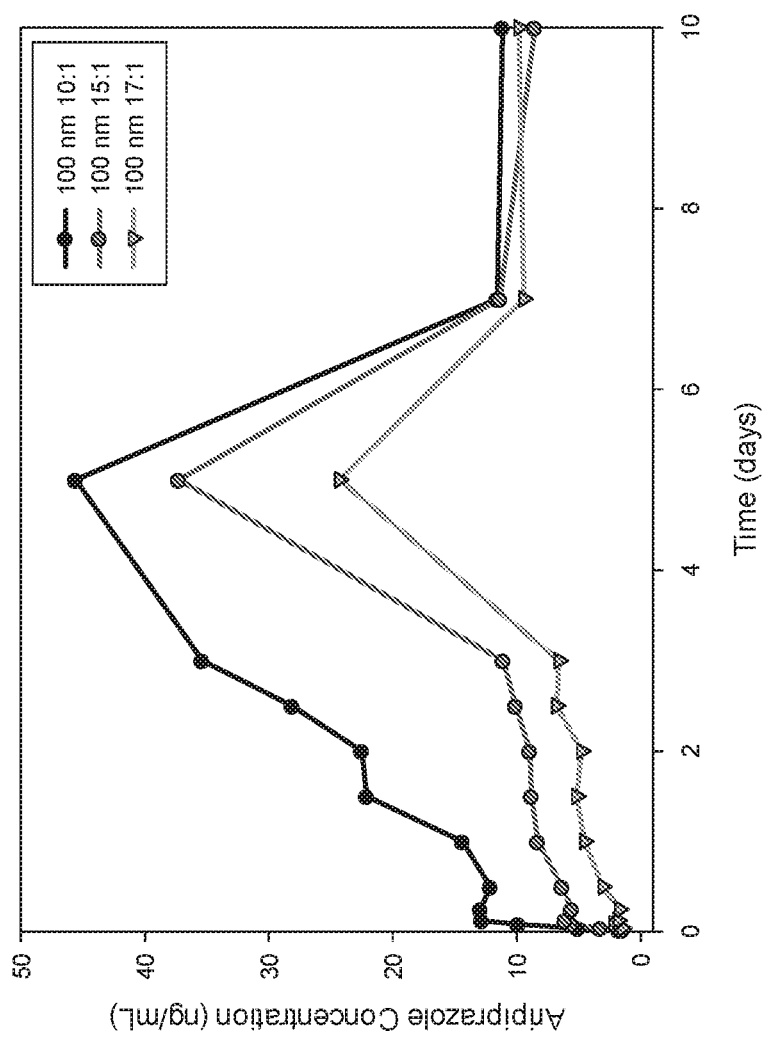
FIG. 12 is a plot of mean aripiprazole concentrations as measured in vivo in dog subjects for Formulations 25, 28 and 29 (illustrating the effect of the active to surface stabilizer ratio on measured aripiprazole levels) as discussed in Example 8.
Figure 16:
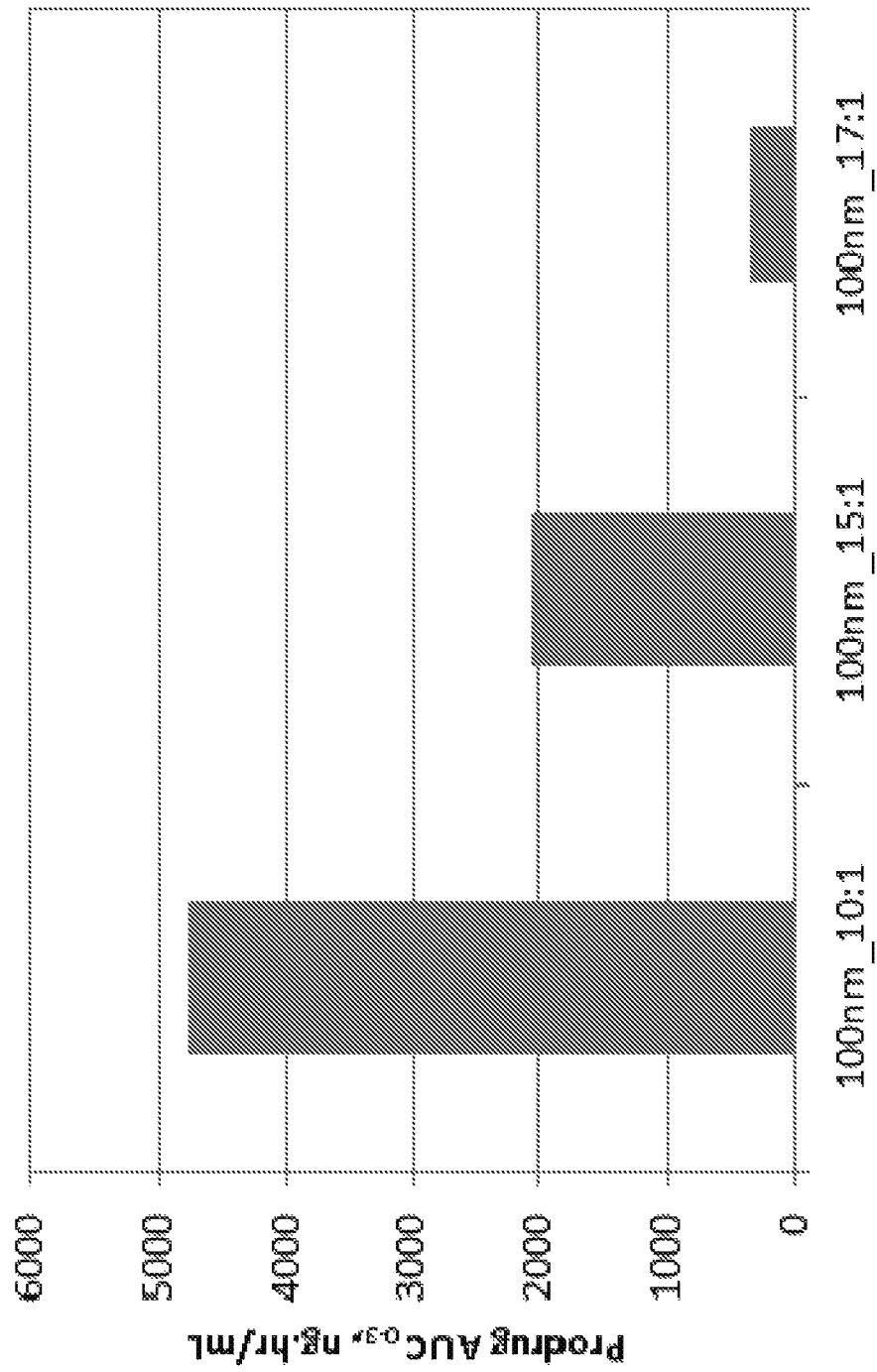
FIG. 16: depicts the AUC of aripiprazole lauroxil for formulations 25, 28 and 29 (formulations at fixed surface area and increasing polysorbate 20 concentration) from dog study.
Figure 17:
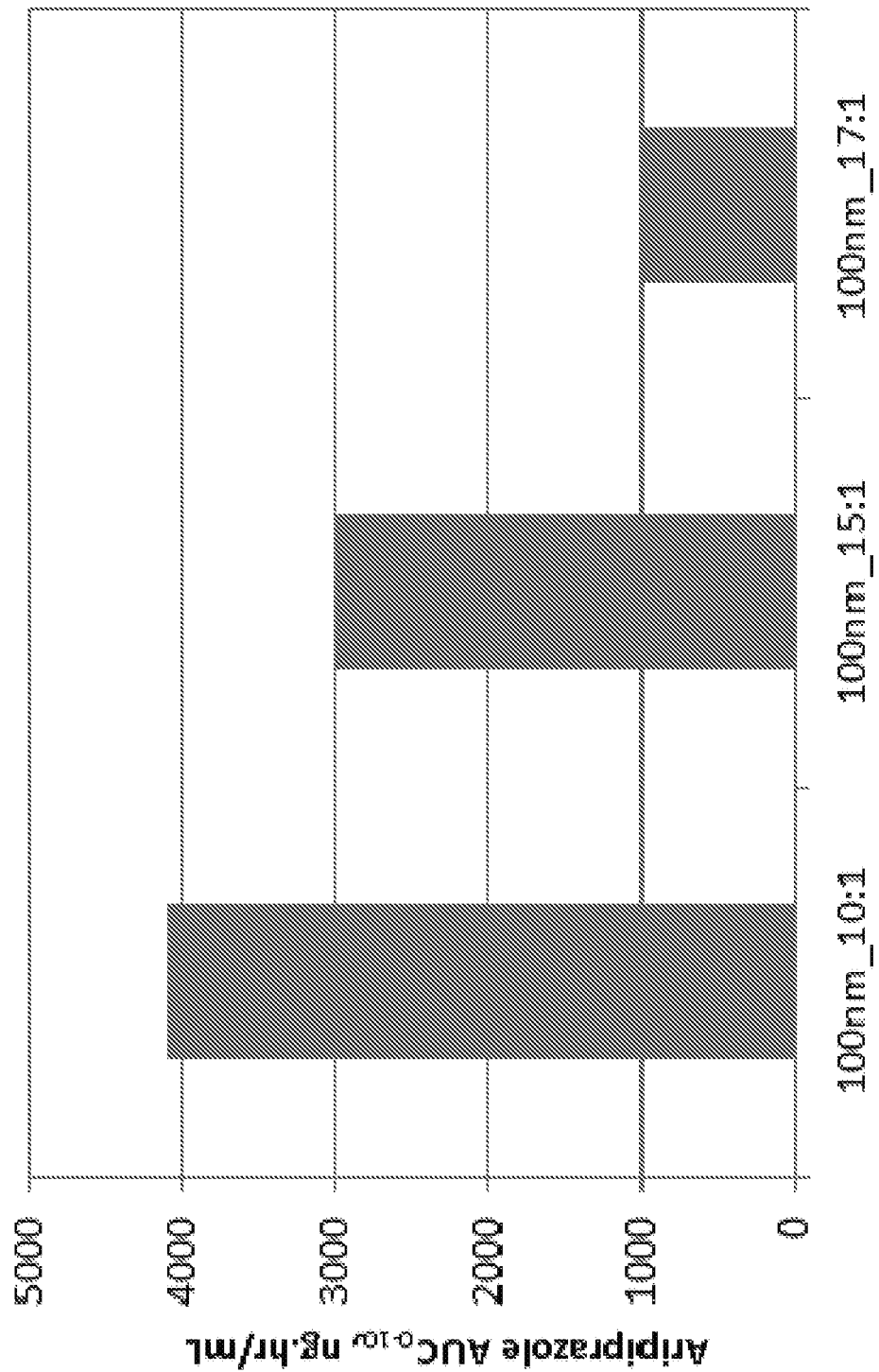
FIG. 17: depicts the AUC of aripiprazole for formulations 25, 28 and 29 (formulations at fixed surface area and increasing polysorbate 20 concentration) from dog study.

The data indicates that for a given particle size distribution (for example 100 nm) when the amount of the surface stabilizer is increased in the formulation, the exposure of aripiprazole lauroxil increases. FIGS. 11 and 16 illustrates the area under the curve (AUC) for aripiprazole lauroxil determined following intramuscular administration in dogs of formulations 25, 28 and 29. Similarly, the exposure of aripiprazole increases as a function of surface stabilizer (FIGS. 17 and 12). This is explained by the fact that at a fixed particle size, i.e. surface area, surface stabilizer will adhere to the surface of the particles until all surfaces are covered, any excess stabilizer present in the formulation vehicle is referred to as free stabilizer. As the amount of free stabilizer increases the solubility of the aripiprazole lauroxil increases. This is supported by the in-vitro data depicted in Table 13 and illustrated in FIG. 18. As more aripiprazole lauroxil is dissolved the exposure in the dog model increases and consequently aripiprazole exposure increases.

Figure 13:
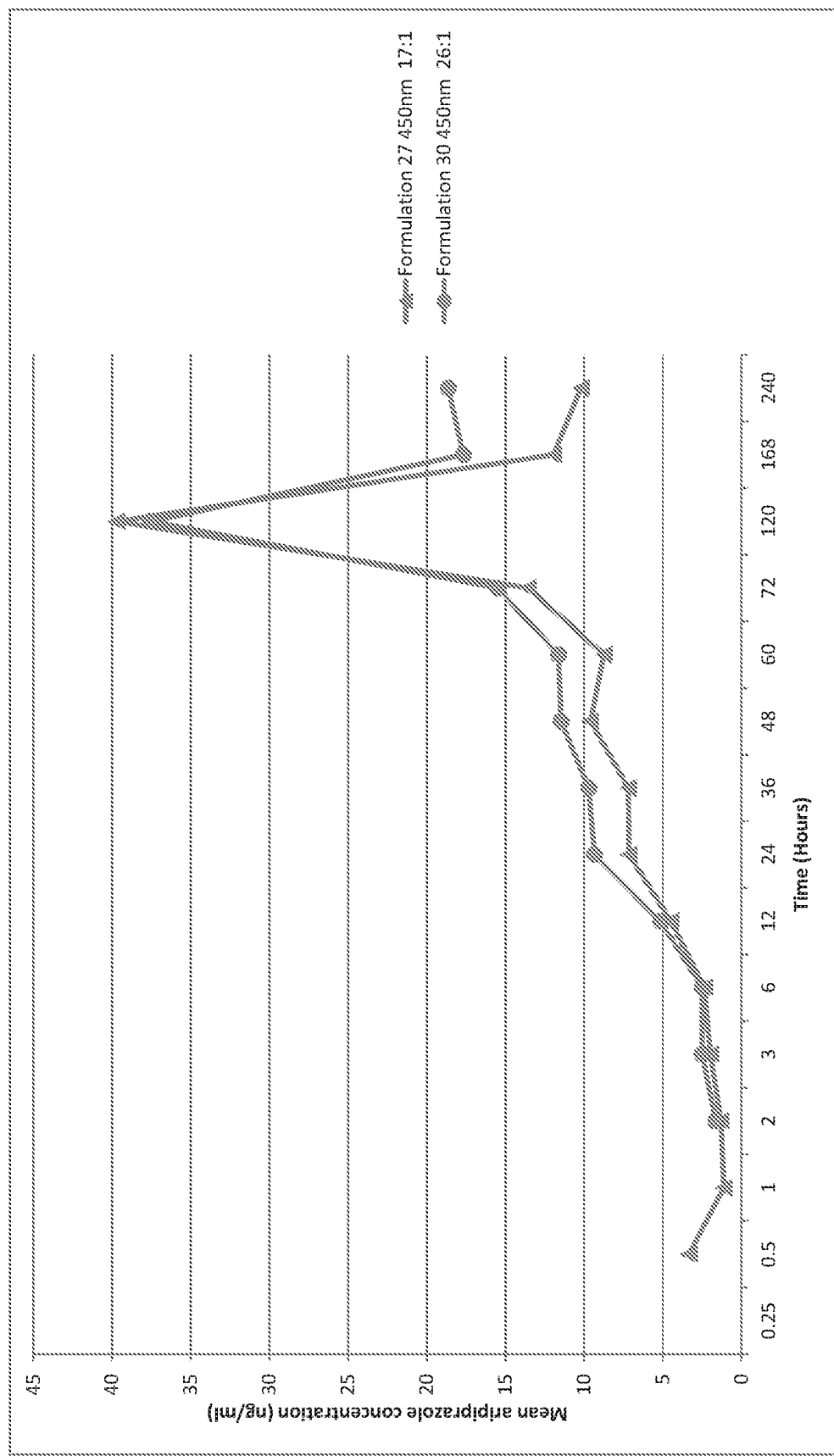
FIG. 13 is a plot of the mean aripiprazole concentrations as measured in vivo in dog subjects for Formulations 27 and 30 (illustrating the effect of the active to surface stabilizer ratio on aripiprazole levels), as discussed in Example 8.
Figure 20:
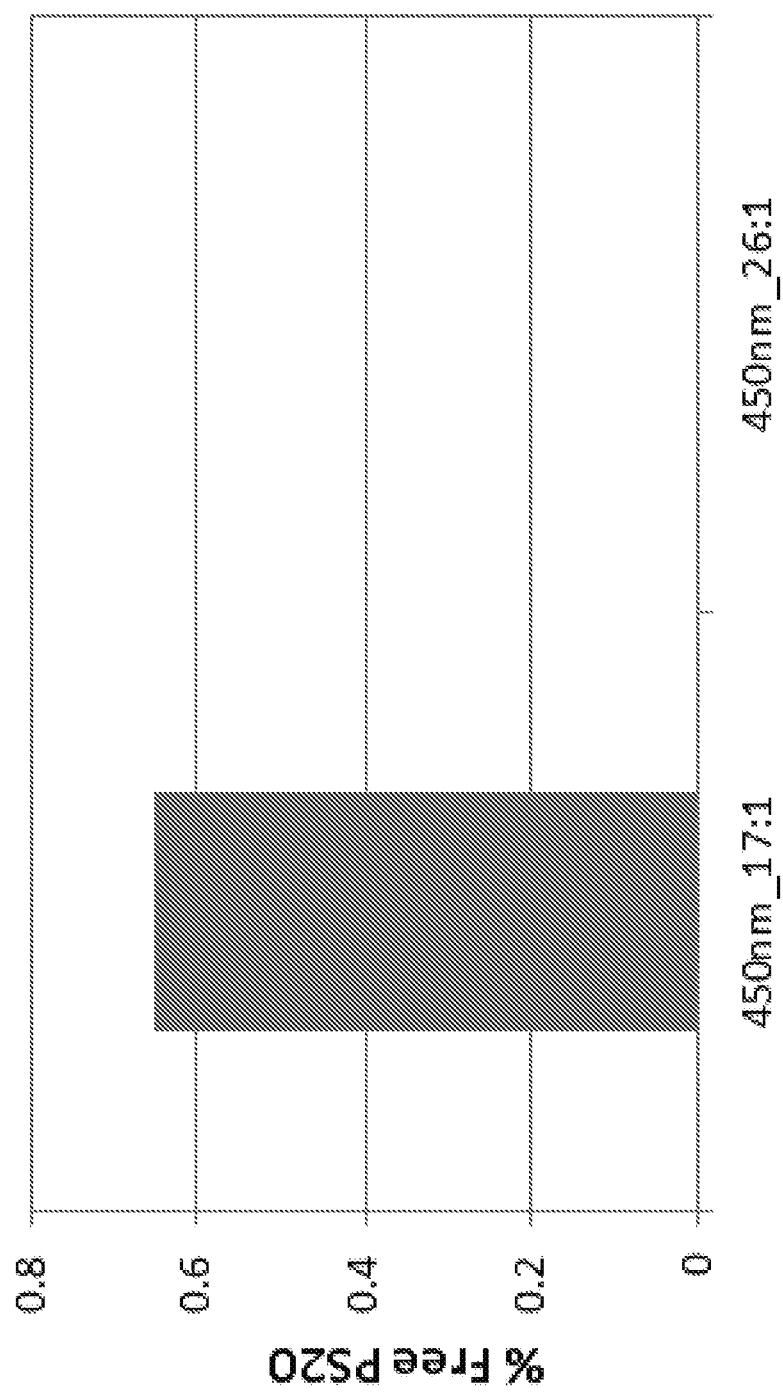
FIG. 20A depicts the amount of free polysorbate 20 for formulations 27 and 30 (formulations at fixed surface area and increasing polysorbate 20 concentration) determined by HPLC.
FIG. 20B depicts the amount of dissolved aripiprazole lauroxil for formulations 27 and 30 (formulations at fixed surface area and increasing polysorbate 20 concentration) determined by HPLC.
Figure 20:
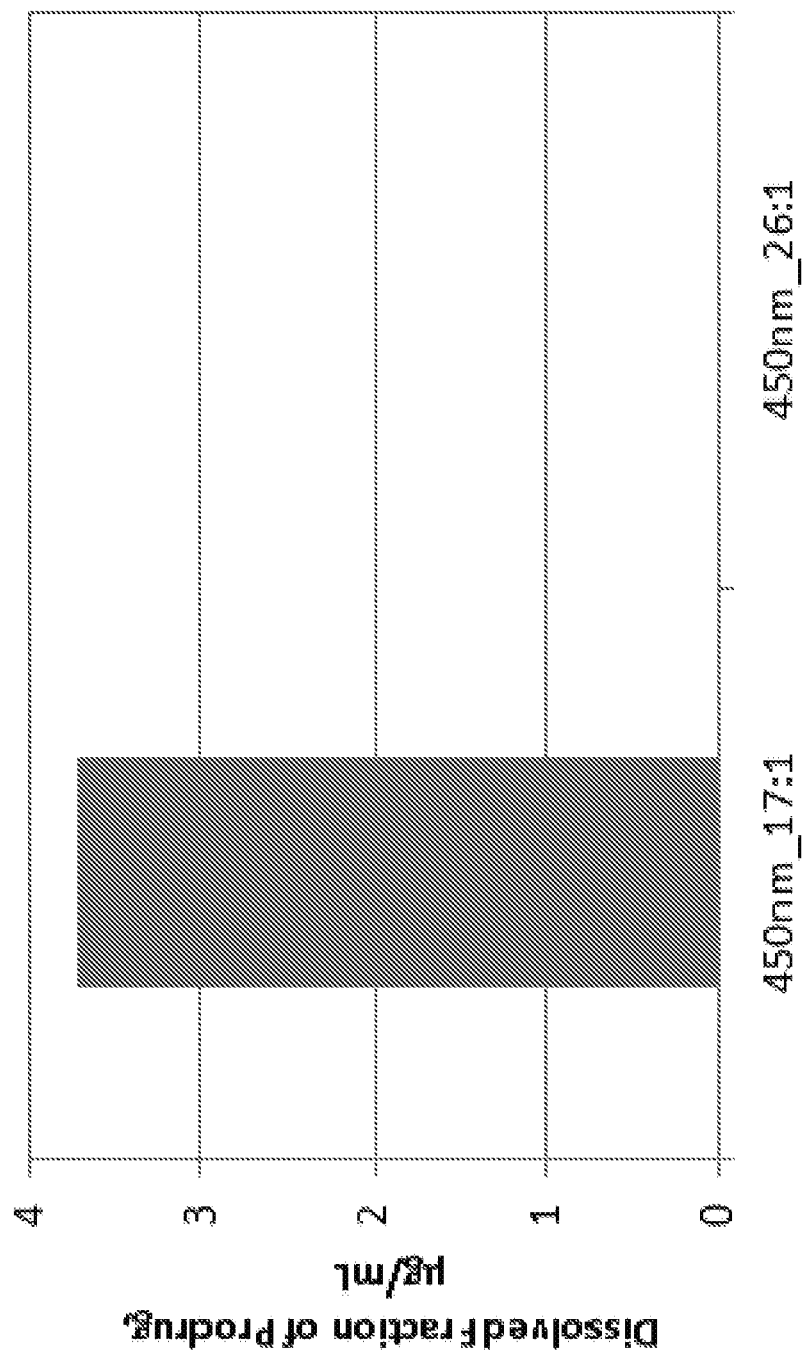

Similar behaviour is also observed for formulations 27 and 30 with larger particle size; i.e. smaller surface area (FIGS. 13, 19A and 20).

Figure 21A:
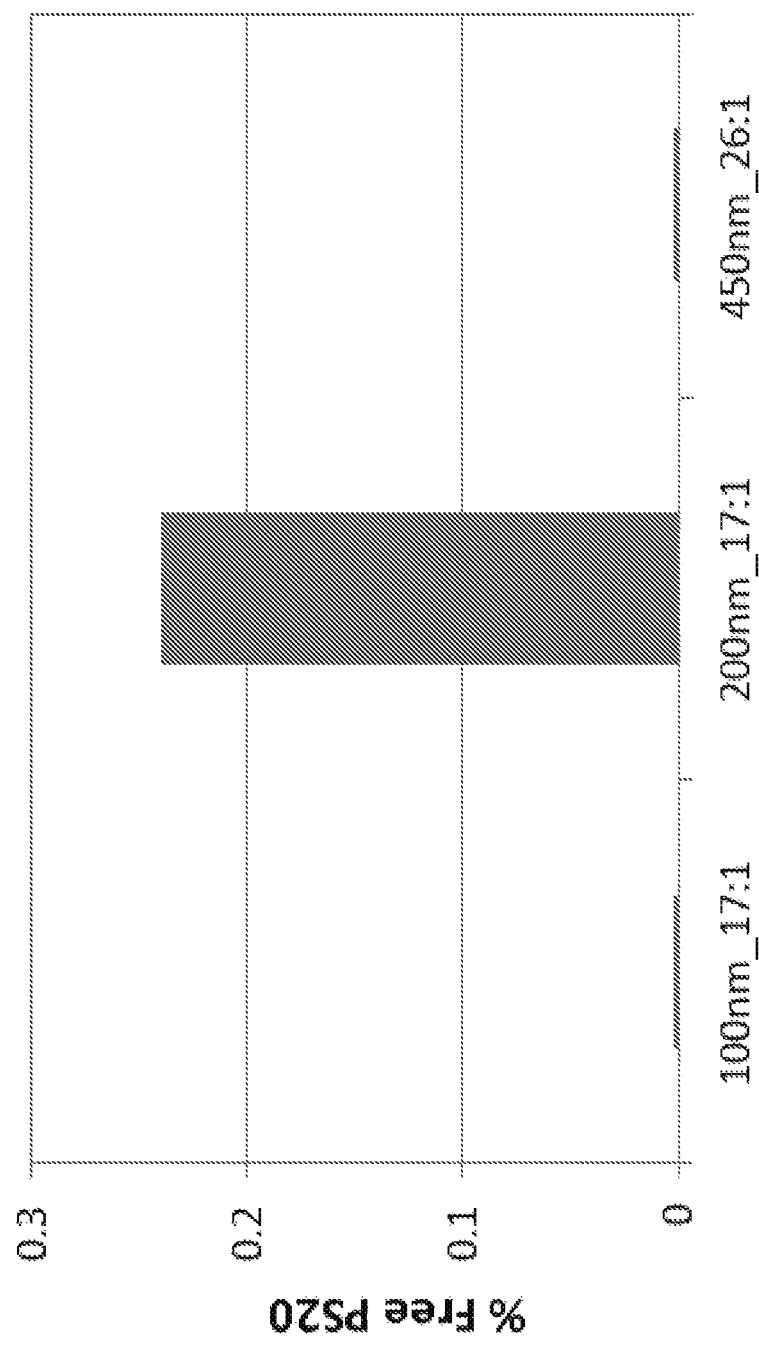
FIG. 21A depicts the amount of free polysorbate 20 for formulations 25, 26 and 30 (formulations at fixed surface area and increasing polysorbate 20 concentration) determined by HPLC.
Figure 21:
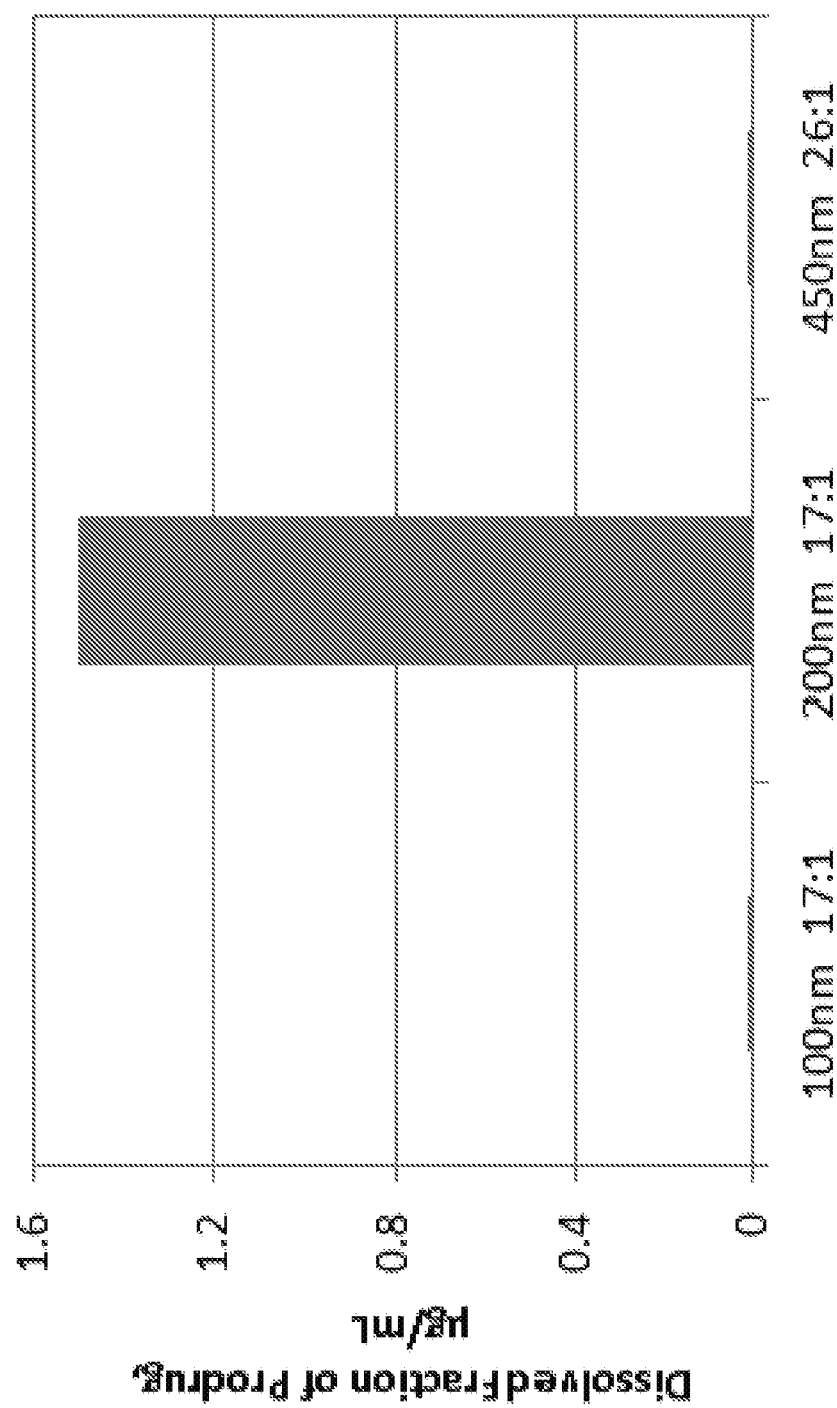
FIG. 21B depicts the amount of dissolved aripiprazole lauroxil for formulations 25, 26 and 30 (formulations at fixed surface area and increasing polysorbate 20 concentration) determined by HPLC.

Despite the fact that Formulations 25 and 30 have different particle size with 100 nm and 450 nm, respectively, the two formulations have no detectable amount of free polysorbate 20 or dissolved aripiprazole lauroxil (FIG. 21). The reason is that the drug to stabilizer ratio is different. Formulation 26 has same drug to stabilizer ratio but with larger particle size (smaller surface area) as formulation 25. As a result, formulation 26 has higher amount of free polysorbate 20 and dissolved aripiprazole lauroxil (FIG. 21).

Figure 22:
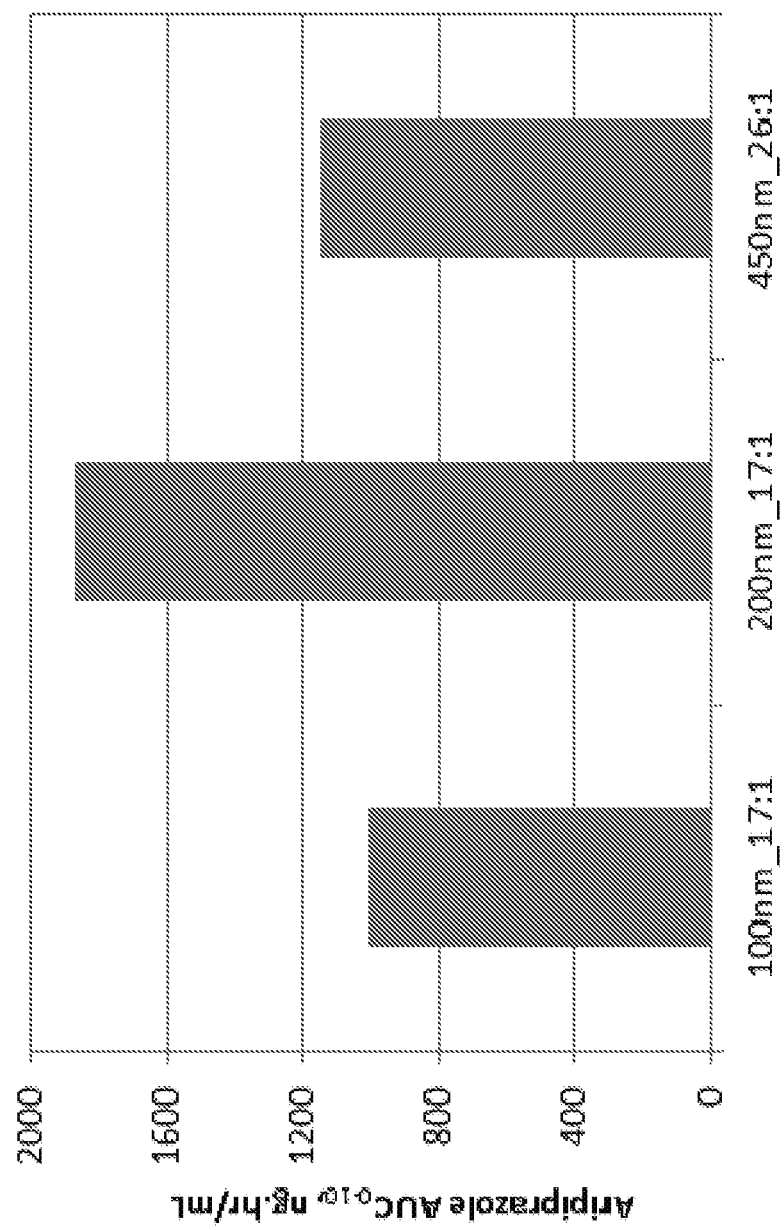
FIG. 22: depicts the AUC of aripiprazole lauroxil and aripiprazole for formulations 25, 26 and 30 (formulations at fixed surface area and increasing polysorbate 20 concentration) from dog study.
Figure 23:
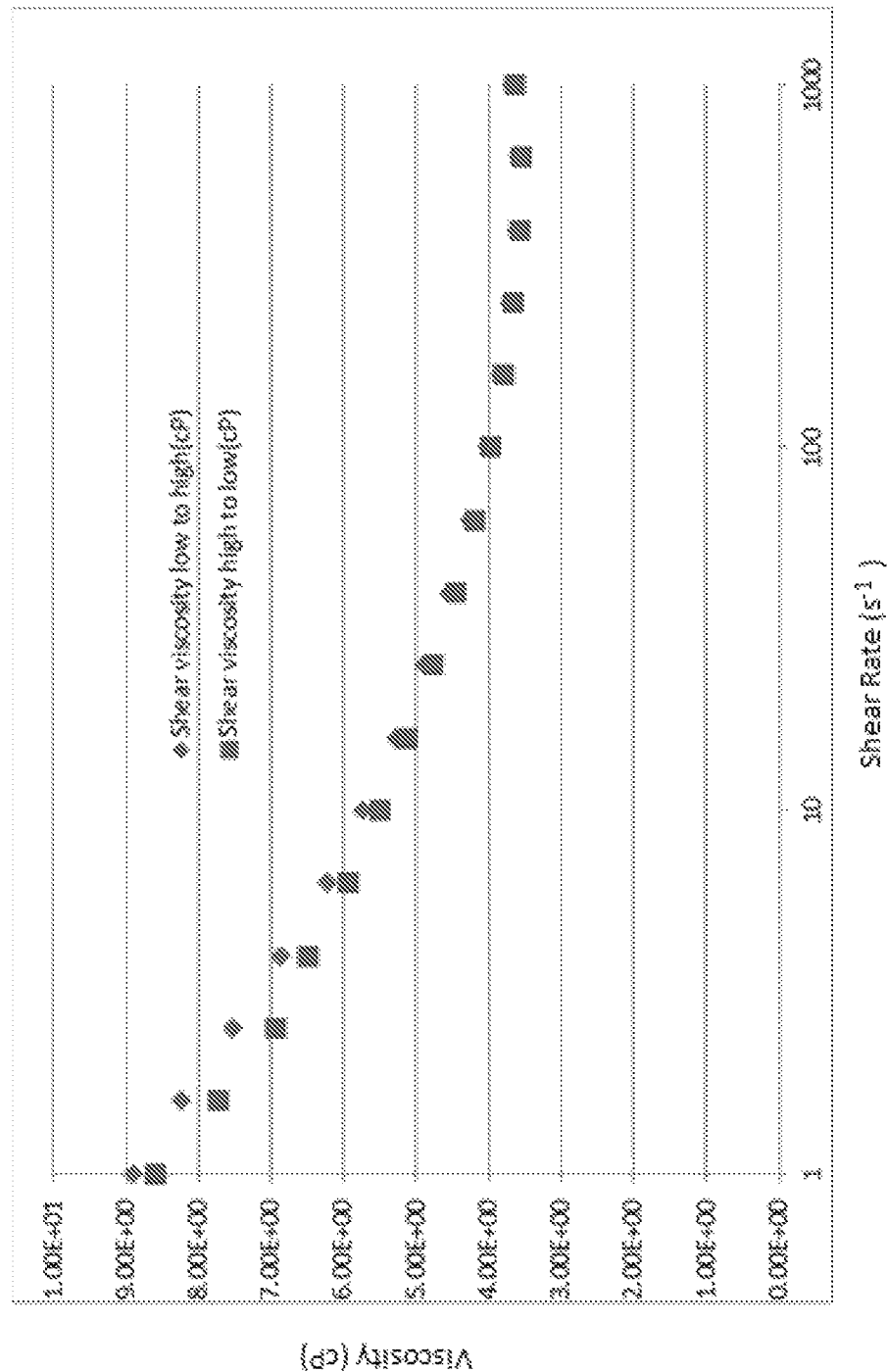
FIG. 23: is a plot of the viscosity verses shear curve as measured for Formulation 31 of Example 9.
Figure 24:
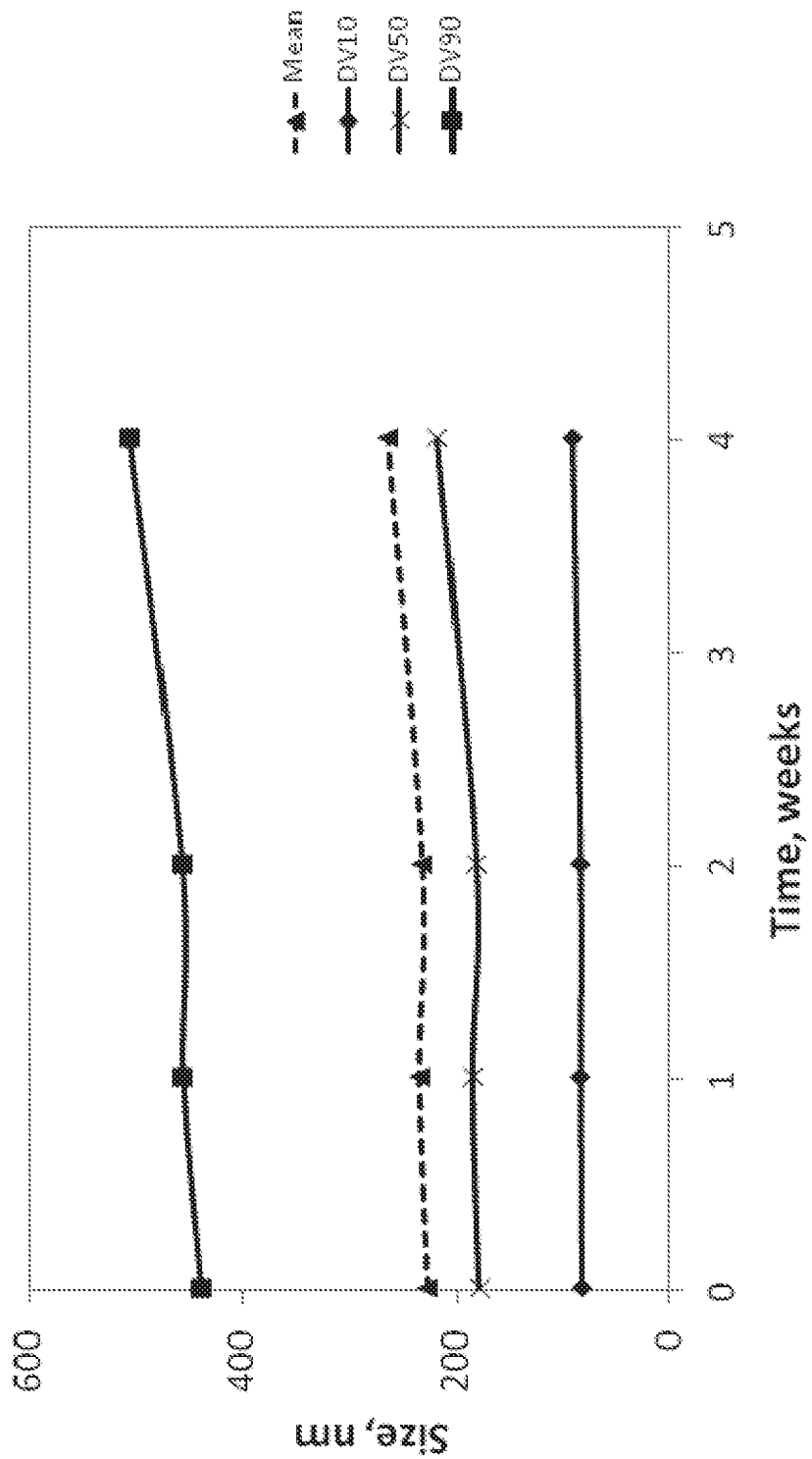
FIG. 24: is a plot of particle size over time as measured for Formulation 31 of Example 9.

FIG. 22 compares the AUC of aripiprazole lauroxil and aripiprazole for formulations 25, 26 and 30. Although formulation 26 has smaller particle size than formulation 25, aripiprazole lauroxil and aripiprazole exposure are higher for formulation 26. This is due to the manipulation in the drug to stabilizer ratio which lead to the difference in the amount of free polysorbate 20 and consequently the amount of dissolved aripiprazole lauroxil in the formulation. Such manipulation did overcome the effect of particle size (surface area) on dissolution where smaller particle sizes dissolve faster.

Figure 14:
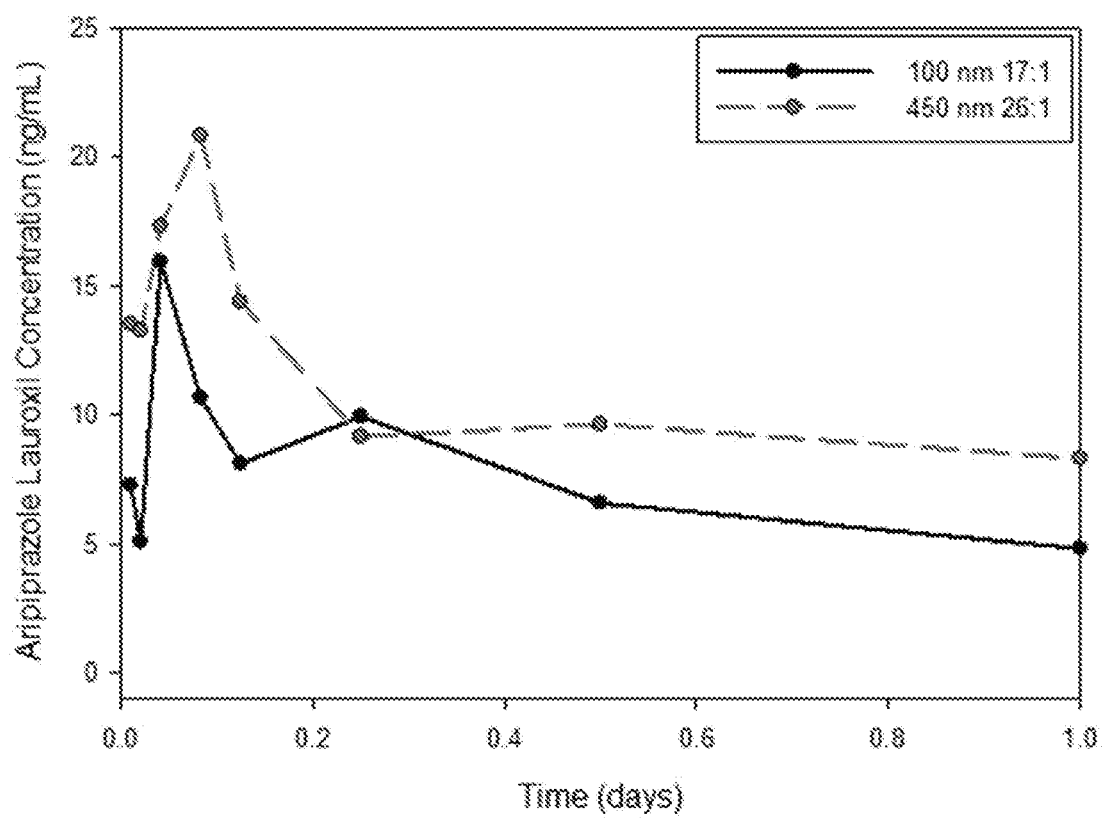
FIG. 14 is a plot of the mean aripiprazole lauroxil concentrations as measured in vivo in dog subjects for Formulations 25 and 30 (illustrating the effect of the active to surface stabilizer ratio on aripiprazole levels), as discussed in Example 8.
Figure 15:
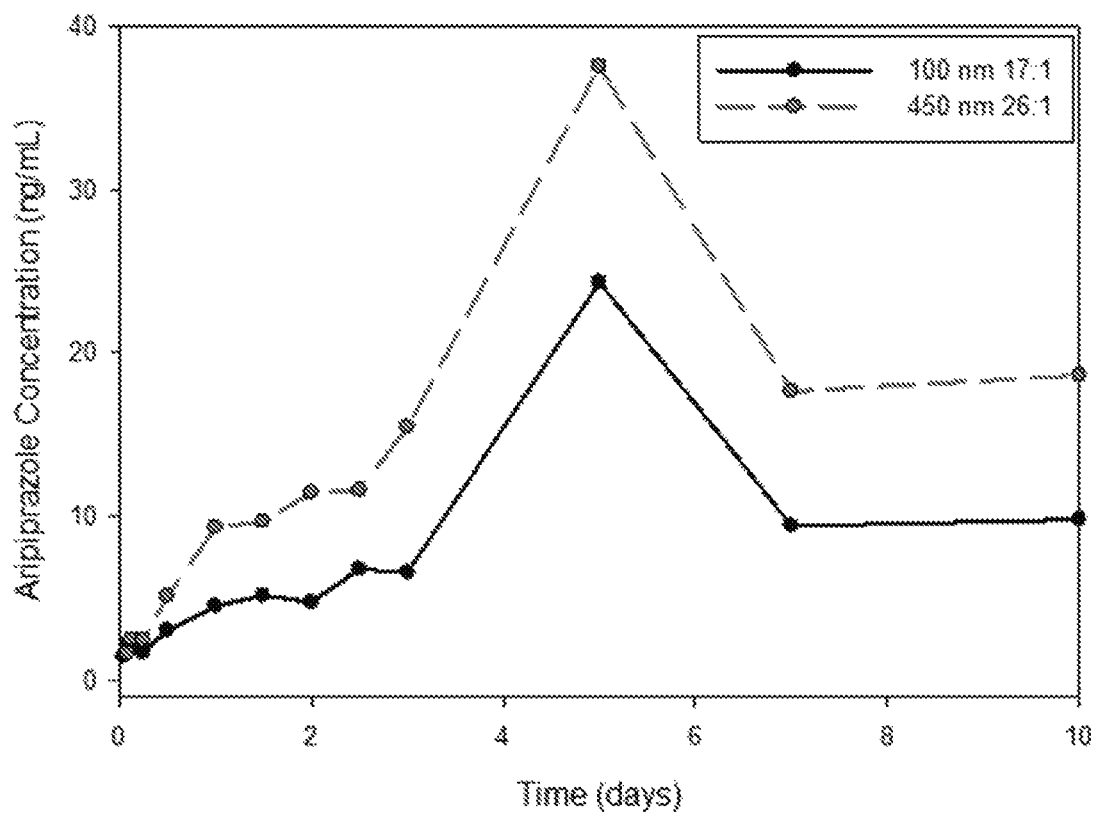
FIG. 15 is a plot of the mean aripiprazole concentrations as measured in vivo in a dog model for Formulations 25 and 30 of Example 8 (illustrating the effect of the active to surface stabilizer ratio on aripiprazole levels).

Similar correlation can be drawn when comparing formulations 25 and 30. Even though, formulations 25 and 30 have very different particle size, the release profiles of the two formulations in dog are similar (FIGS. 14, 15 and 19B).

Figure 9:
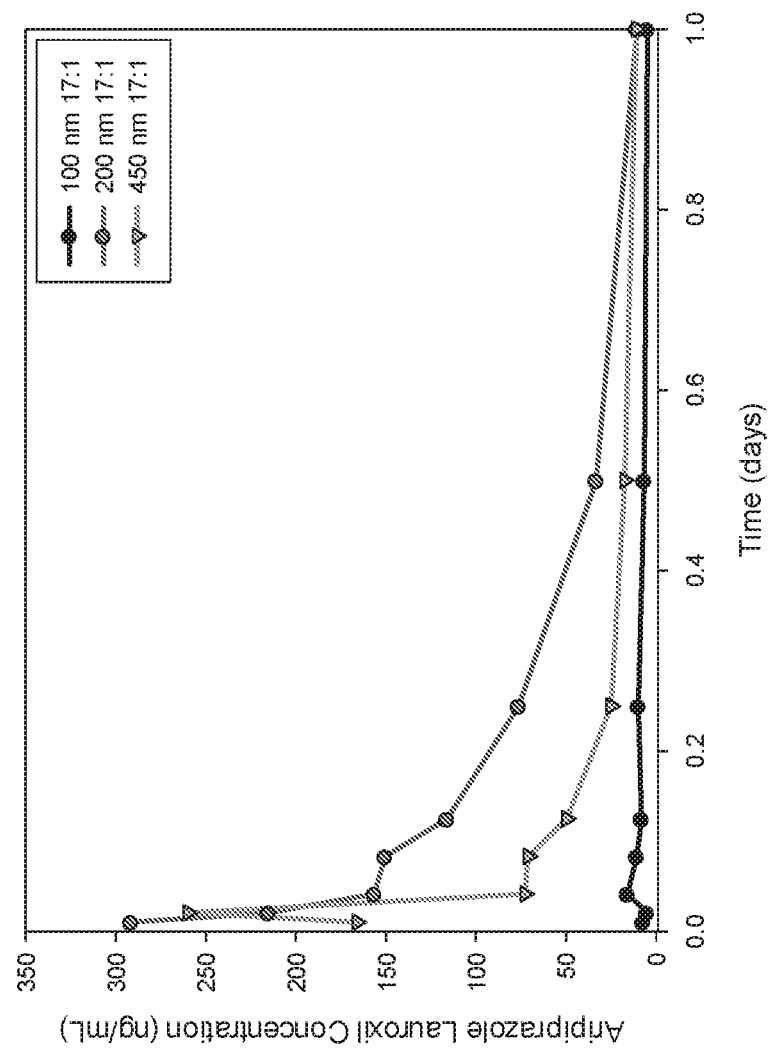
FIG. 9 is a plot of the mean aripiprazole concentrations as measured in vivo in dog subjects for Formulations 25, 26 and 27 of Example 8.
Figure 10:
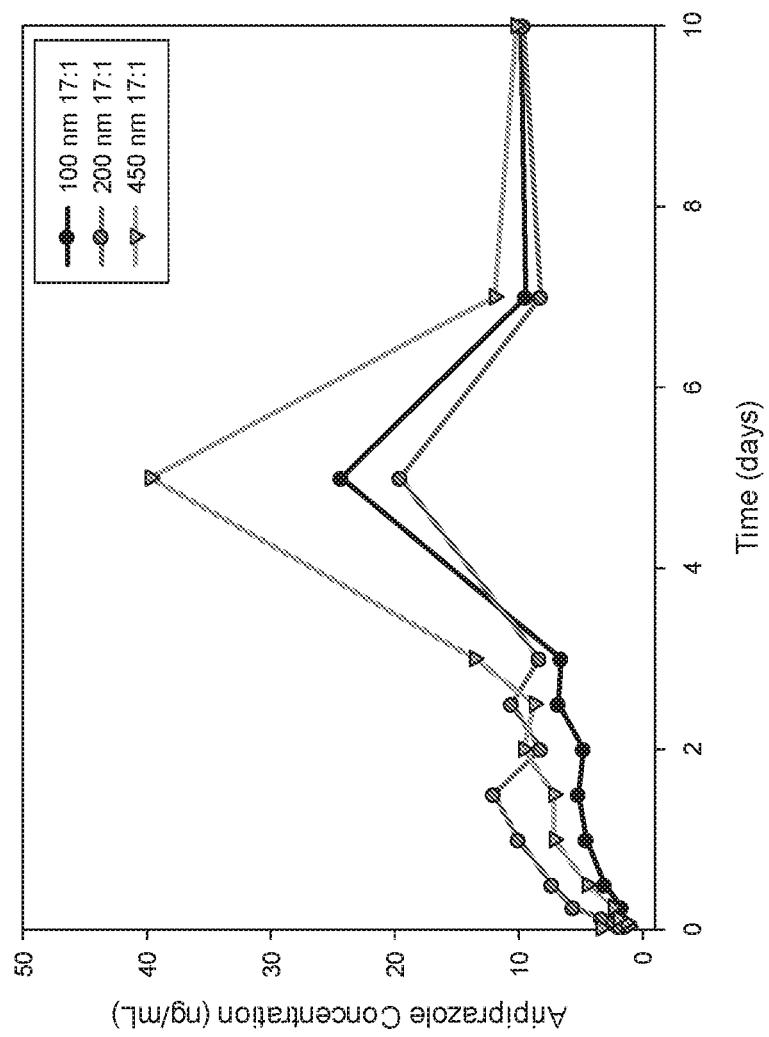
FIG. 10 is a plot of the mean aripiprazole concentrations as measured in vivo in dog subjects for Formulations 25 to 27 of Example 8.

FIG. 9 and FIG. 10 depict the mean aripiprazole lauroxil concentrations as measured in vivo for Formulations 25-27 where the drug to API ratio is fixed and the particle size is varied. Formulation 26 showing that an intermediate particle (200 nm) size in comparison to Formulation 25 (100 nm) and 27 (450 nm) has a higher initial exposure of aripiprazole and aripiprazole lauroxil.

Example 9

In order to demonstrate that the compositions of the present are size stable, a number of studies were conducted, some of which are described below.

Formulation 31 was prepared in order to assess the stability of a composition according to the present invention. A four week stability study was conducted on a formulation comprising 20% aripiprazole lauroxil. The composition had a 14:1 aripiprazole lauroxil to surface stabilizer ratio. In addition, 10 mM Phosphate buffered saline and 26 mM citrate buffered saline were added as buffers. FIG. 17 is a plot of particle size measurements over various timepoints demonstrating the formulation stability for Formulation 31. As evidenced by the data in the plot, the composition was found to exhibit very little particle size growth over the study period.

In addition to producing compositions stability studies were also carried out in relation to a number of other formulations as summarised below in Table 16 below.

TABLE 16

6 month stability analysis of alternative formulations

| Formulation Summary | Temperature (° C.) | T = 0 Mean (nm) | 1 mth Mean (nm) | 3 mth Mean (nm) | 6 mth Mean (nm) |
|---|---|---|---|---|---|
| Aripirazole Lauroxil 200 nm stabilized with PS 20 30% (w/w) API + 2% (w/w) PS20 | 2-8 | 200 | 200 | 210 | 260 |
| Aripirazole Lauroxil 200 nm stabilized with PS 20 | 2-8 | 200 | No data | 220 | 250 |

TABLE 16-continued 6 month stability analysis of alternative formulations

| Formulation Summary | Temperature (° C.) | T = 0 Mean (nm) | 1 mth Mean (nm) | 3 mth Mean (nm) | 6 mth Mean (nm) |
|---|---|---|---|---|---|
| Citrate-Sucrose | 25 | No data | No data | 230 | 280 |
| 27% API + 1.8% PS20 + Citrate Buffered Sucrose | 40 | No data | No data | 250 | 390 |
| Aripiprazole Lauroxil 200 nm stabilized with PS 20 | 2-8 | 200 | No data | 220 | 250 |
| 27% API + 1.8% PS20 + Citrate Buffered Saline | 25 | No data | 230 | 240 | 300 |
| | 40 | No data | 310 | No data | 570 |
| Aripiprazole Lauroxil 500 nm stabilized with PS 20 | 2-8 | 480 | 540 | 570 | 590 |
| 30% API + 2% PS20 Aripiprazole Lauroxil 500 nm stabilized with PS 20 | 2-8 | 530 | No Data | 530 | 530 |
| 27% API + 1.8% PS20 + Citrate Buffered Sucrose | 25 | No Data | 550 | 650 | 360 with Sediment |
| | 40 | No Data | 780 | Aggregate | NA |
| Aripiprazole Lauroxil 500 nm stabilized with PS 20 | 2-8 | 480 | No Data | 610 | 660 |
| 27% API + 1.8% PS20 + Citrate Buffered Saline | 25 | No Data | 580 | 720 | 780 |
| | 40 | No Data | 780 | 760 | 800 |

Example 10

Although polysorbate 20 is a preferred choice of surface stabilizer, the present invention may also be realised using alternative surface stabilizers. To demonstrate this, Formulation 32 was prepared, which comprised aripiprazole cavoxil particles which were stabilized with beta hydroxyl cyclodextrin. The composition as prepared comprised 5% w/w aripiprazole cavoxil and 10% beta hydroxyl cyclodextrin. The final composition had a particle size of approximately 250 nm and was demonstrated to have very little particle size growth over a four week period as outlined in Table 17 below.

TABLE 17

4 week stability analysis for Formulation 32

| Storage Temperature (° C.) | Time (weeks) | Mean (nm) | Dv10 (nm) | Dv50 (nm) | Dv90 (nm) |
|---|---|---|---|---|---|
| 4 | 0 | 269 | 199 | 255 | 362 |
| | 1 | 243 | 172 | 233 | 325 |
| | 4 | 255 | 181 | 245 | 334 |
| 25 | 1 | 266 | 190 | 259 | 348 |
| | 4 | 293 | 195 | 268 | 388 |

Example 11

At the time of writing, Formulations 33-36 discussed below are due to be dosed as part of a human study. Formulations 33, 34 and 35 are largely very similar to Formulations 25, 26 and 30 prepared for the dog study discussed in Example 8 above.

Formulation 33 will be prepared from a crude slurry comprising 26% w/w aripiprazole lauroxil and 1.53% w/w polysorbate 20 as a surface stabilizer (i.e. approximately 17:1 ratio of active to surface stabilizer). To this, 10 mM phosphate buffer (pH 6.8) will be added along with 26 mM of citrate buffered saline. The formulation will be milled in a similar manner to Formulation 30 discussed above in order to produce a final volume based particle size before dosing of about 100 nm (+−50 nm).

Formulation 34 will be prepared from a crude slurry comprising 26% w/w aripiprazole lauroxil and 1.53% w/w polysorbate 20 as a surface stabilizer (i.e. approximately 17:1 ratio of active to surface stabilizer). To this, 10 mM phosphate buffer (pH 6.8) will be added along with 26 mM of citrate buffered saline. The formulation will be milled in a similar manner to Formulation 31 discussed above in order to produce a final volume based particle size before dosing of about 200 nm (+−50 nm).

Formulation 35 will be prepared from a crude slurry comprising 26% w/w aripirazole lauroxil and 1% w/w polysorbate 20 as a surface stabilizer (i.e. approximately 26:1 ratio of active to surface stabilizer). To this, 10 mM phosphate buffer (pH 6.8) will be added along with 26 mM of citrate buffered saline. The formulation will be milled in a similar manner to Formulation 35 discussed above in order to produce a final volume based particle size before dosing of about 450 nm (+−50 nm).

Formulation 36 will be prepared from a crude slurry comprising 26% w/w aripiprazole lauroxil, 1% w/w polysorbate 20 (forming a drug:surface stabilizer ratio of 26:1) in 10 mM phosphate buffer, pH 6.8. 26 mM citrate buffered saline is added as a buffer. The aforementioned composition will be milled such that the final particle size will be approximately 900 nm (+−50 nm). The composition details for Formulation 33-36 are summarised in Table 18 below.

TABLE 18

Details of compositions for human study

| Component | Formulation 33 (w/w %) | Formulation 34 (w/w %) | Formulation 35 (w/w %) | Formulation 36 (w/w %) |
|---|---|---|---|---|
| Aripiprazole Lauroxil | 26 | 26 | 26 | 26 |
| Polysorbate 20 | 1.53 | 1.53 | 1 | 1 |
| Sodium Citrate | 0.76 | 0.76 | 0.76 | 0.76 |
| Sodium chloride | 0.31 | 0.31 | 0.31 | 0.31 |
| Sodium phosphate Buffer | 0.15 | 0.15 | 0.15 | 0.15 |
| Water for Injection | 71.25 | 71.25 | 71.78 | 71.78 |

It is anticipated that each of the aforementioned compositions will exhibit a faster onset and reduced $T_{max}$ in pharmacokinetic properties when dosed in humans, and in particular that the onset time will be greatly improved in comparison to larger particle size formulations, in particular the 20 μm aripiprazole formulation described in the previous examples of the present specification.

Example 12

Effect of Secondary Stabilizer on PK in Rodent Model:

Formulation X was prepared from a crude slurry (total 5.86 g) comprising 15% w/w aripirazole cavoxil and 1.6% w/w polysorbate 20 as a surface stabilizer (i.e. approximately 9:1 ratio of active to surface stabilizer). Polymill milling media having a size of 500 μm was added, the total media load being 69%. The slurry was placed inside a 10 ml chamber of a NanoMill® 0.01 mill having a straight shaft and milled at 1500 rpm for a total of 45 minutes at a temperature of 15° C. A portion of this batch was diluted to 8% aripirazole cavoxil with 1.6% polysorbate 20 in phosphate buffer saline (pH 6.8). The final composition had a mean particle size of 584 nm, the Dv50 was 549 nm, the Dv90 was 961 and the Dv10 was 261.

Formulation Y was prepared by diluting the other portion of the above batch was diluted to 8% aripirazole cavoxil with 1.6% polysorbate 20 in phosphate buffer saline (pH 6.8) and 0.1% pluronic F108 as a secondary stabilizer. The final composition had a mean particle size of 584 nm, the Dv50 was 549 nm, the Dv90 was 961 and the Dv10 was 261.

Formulations X and Y were stored at room temperature prior to dosing. Six rat subjects were used. The compositions were dosed intramuscularly, at a dose strength of approximately 20 mg, active concentration of 65 mg/mL and a dose volume of 0.3 mL.

Figure 25:
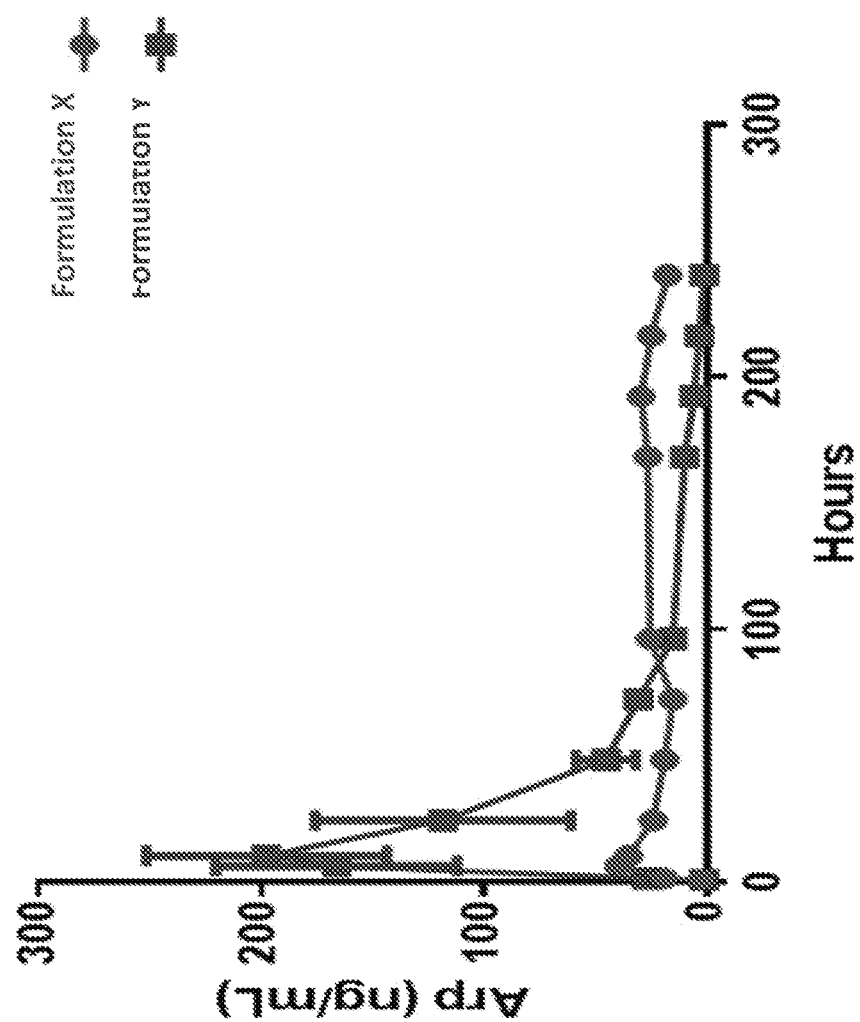
FIG. 25: depicts the mean aripiprazole concentrations as measured in vivo in a rodent model for Formulations X and Y of Example 12.

The mean aripirazole concentration curves for Formulations X and Y are shown in FIG. 25. The study demonstrated that by adding a secondary stabilizer a significant change in the $C_{max}$ was observed in vivo. The aripirazole exposure increase significantly (5 times) in formulation Y compared to X.

Figure 26:
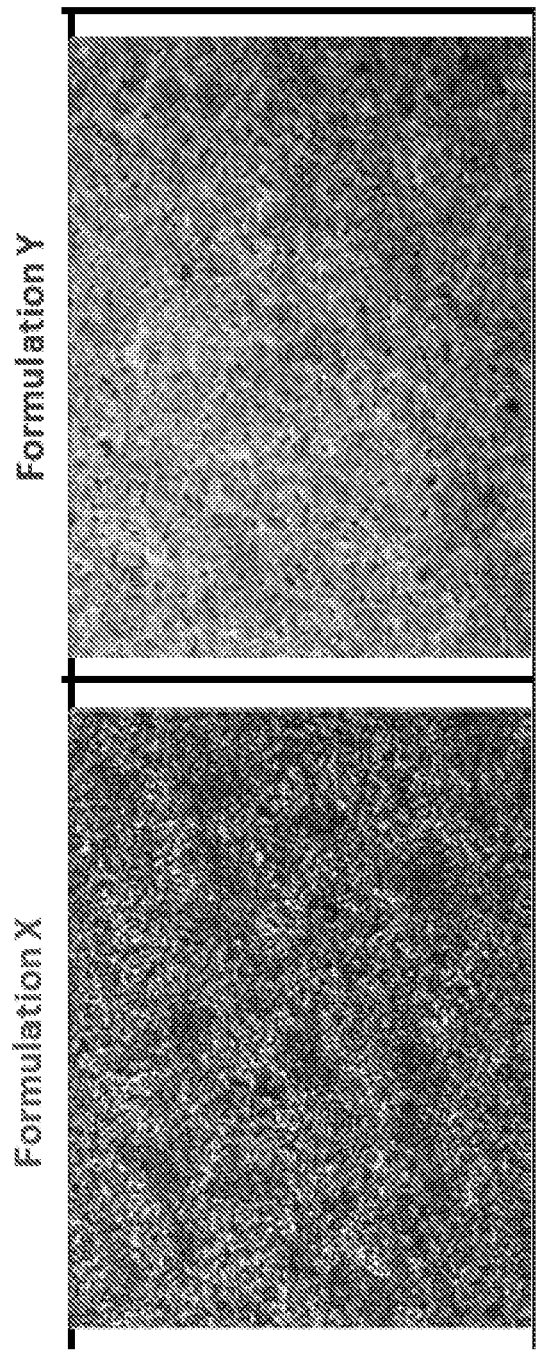
FIG. 26: depicts the microscope images of formulations X and Y diluted in phosphate buffer saline of Example 12.

Observation under the microscope for a drop of formulation X diluted in phosphate buffer saline showed aggregates formation (FIG. 26). On the other hand, when formulation Y was diluted in phosphate buffer saline, the formulation showed no aggregation under the microscope. This might indicate that when injected into the intramuscular space, formulation X might form aggregates which reduce the surface area in contact with the muscle. On the other hand, formulation Y might form an injection depot that is spread between the muscles which increases the surface area contact thus leads to increase in exposure.

While certain of the preferred embodiments of the present invention have been described and specifically exemplified above, it is not intended that the invention be limited to such embodiments. Various modifications may be made thereto without departing from the scope and spirit of the present invention.

The invention claimed is:

1. A composition comprising:
    (a) a population of particles of an aripiprazole prodrug having a volume based particle distribution size (Dv50) of between 50 and 700 nm as determined by light scattering techniques;
    (b) at least one surface stabilizer comprising an adsorbed component which is adsorbed on the surface of the aripiprazole prodrug particles and a free component available for solubilisation of the aripiprazole prodrug; wherein the ratio of aripiprazole prodrug to surface stabilizer is about 17:1;

wherein the aripiprazole prodrug has the formula:

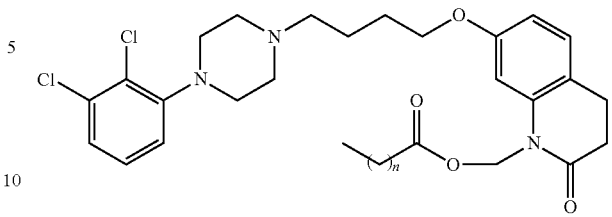

where n is zero or an integer less than 20; and
wherein the at least one surface stabilizer is selected from the group consisting of carboxymethyl cellulose and polyoxyethylene sorbitan fatty acid esters.

2. The composition of claim 1, wherein in the aripiprazole prodrug formula n is equal to 4.

3. The composition of claim 1, wherein in the aripiprazole prodrug formula n is equal to 10.

4. The composition of claim 1, wherein the free component of the at least one surface stabilizer constitutes greater than 0% (w/w) and no more than about 3% (w/w) of the composition.

5. The composition of claim 1, wherein the volume based particle distribution size (Dv50) of the aripiprazole prodrug particles is between 175 nm and 350 nm.

6. The composition of claim 1, wherein the at least one surface stabilizer is a polyoxyethylene sorbitan fatty acid ester.

7. The composition of claim 1, wherein the at least one surface stabilizer is polysorbate 20.

8. The composition of claim 1, wherein the composition comprises a primary surface stabilizer and at least one secondary surface stabilizer.

9. The composition of claim 1, wherein the composition further comprises a dispersion medium in which the population of aripiprazole prodrug particles is dispersed, wherein the free component of the surface stabilizer is dissolved or otherwise dispersed within the dispersion medium.

10. The composition of claim 1, adapted for administration as a depot injection.

11. The composition of claim 1, wherein the composition is provided in an injection device, wherein the injection device is a pre-filled syringe, an auto-injector, a needleless syringe, or a dual chambered syringe.

12. The composition of claim 11, wherein the aripiprazole prodrug composition is provided in one chamber of the dual chambered syringe, and the other chamber of the dual chamber syringe is provided with a second composition.

13. The composition of claim 12, wherein the second composition is an aripiprazole prodrug composition, having a volume based particle distribution size (Dv50) of at least 200 nm, of at least 300 nm, of at least 400 nm, of at least 500 nm, of at least 600 nm, of at least 700 nm, of at least 800 nm, of at least 900 nm, of at least 1000 nm, of at least 1500 nm, of at least 2000 nm, of at least 5000 nm, of at least 10,000 nm greater than the aripiprazole prodrug composition, or the second composition is an atypical antipsychotic other than an aripiprazole prodrug.

14. The composition of claim 1, wherein the composition is formulated as a powder for reconstitution in a liquid medium, wherein the population of aripiprazole prodrug particles redisperse in the liquid medium such that the redispersed aripiprazole prodrug particles have a volume based particle distribution size (Dv50) of less than 1000 nm.

15. The composition of claim 1, further comprising an additional atypical antipsychotic other than the aripiprazole prodrug.

16. The composition of claim 1, wherein the viscosity of the composition is below 10 cP at a shear rate of about 100 $s^{-1}$, when measured at a temperature of about 25° C.

17. The composition of claim 1, wherein the composition comprises a population of particles of the formula:

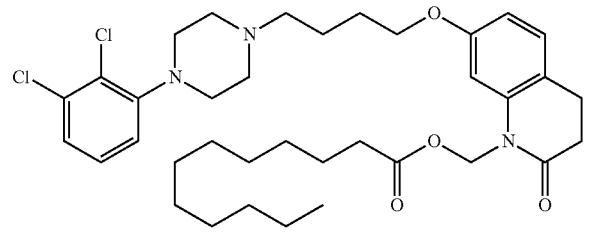 [SMILES: CCCCCCCCCCCC(=O)OCN1C(=O)CCc2ccc(OCCCCN3CCN(c4cccc(Cl)c4Cl)CC3)cc21]

having a volume based particle distribution size (Dv50) of between 350 nm and 175 nm as determined by light scattering techniques, wherein the ratio of said particles to polysorbate 20 is 17:1.

18. The composition of claim 17, wherein the composition further comprises a chelating agent, a tonicity agent, and a buffer.

19. The composition of claim 18, wherein the chelating agent is sodium citrate and the tonicity agent is sodium chloride.

20. The composition of claim 1, wherein the composition consists of:
   a) 26 weight percent of an aripiprazole prodrug of the following formula:

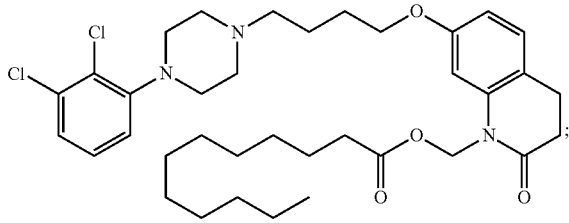 [SMILES: CCCCCCCCCCCC(=O)OCN1C(=O)CCc2ccc(OCCCCN3CCN(c4cccc(Cl)c4Cl)CC3)cc21]

b) 1.53 weight percent polysorbate 20;
   c) 0.76 weight percent sodium citrate;
   d) 0.31 weight percent sodium chloride;
   e) 0.15 weight percent sodium phosphate buffer; and
   f) 71.25 weight percent water for injection;
   wherein the compound is provided as a population of particles having a volume based particle distribution size (Dv50) of 100 nm or 200 nm as determined by light scattering techniques.

21. The composition of claim 1, wherein the composition comprises a population of particles of the formula:

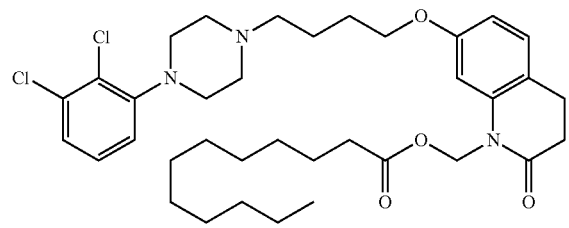 [SMILES: CCCCCCCCCCCC(=O)OCN1C(=O)CCc2ccc(OCCCCN3CCN(c4cccc(Cl)c4Cl)CC3)cc21]

having a volume based particle distribution size (Dv50) of between 350 nm and 175 nm as determined by light scattering techniques, wherein the ratio of said particles to polysorbate 20 is about 17:1.

* * * * *